(12) United States Patent
Still et al.

(10) Patent No.: US 6,797,522 B1
(45) Date of Patent: Sep. 28, 2004

(54) SYNTHETIC RECEPTORS

(75) Inventors: W. Clark Still, New York, NY (US); Ge Li, Plainsboro, NJ (US); Helma Wennemers, New York, NY (US)

(73) Assignee: The Trustees of Columbia University in the City of New York, New York, NY (US)

(*) Notice: Subject to any disclaimer, the term of this patent is extended or adjusted under 35 U.S.C. 154(b) by 617 days.

(21) Appl. No.: 09/041,343

(22) Filed: Mar. 12, 1998

Related U.S. Application Data

(62) Division of application No. 08/676,143, filed on Oct. 24, 1996.

(51) Int. Cl.[7] .................... G01N 33/566; A61K 38/00; C07H 1/00; C07D 291/00
(52) U.S. Cl. .................. 436/518; 436/501; 436/528; 436/529; 436/531; 436/534; 530/334; 536/25.3; 544/1; 544/2; 548/100
(58) Field of Search .................. 435/6, 7.1; 436/501, 436/518, 528, 529, 531, 534; 530/333, 334; 536/1.11, 23.1, 25.3; 544/1, 2; 548/100

(56) References Cited

U.S. PATENT DOCUMENTS

| | | | | |
|---|---|---|---|---|
| 5,369,017 A | * | 11/1994 | Wong et al. | 435/68.1 |
| 5,567,795 A | * | 10/1996 | Vicari et al. | 528/206 |
| 5,646,285 A | * | 7/1997 | Baindur et al. | 546/298 |
| 5,786,156 A | * | 7/1998 | Taddei-Peters et al. | 435/7.9 |
| 5,804,563 A | * | 9/1998 | Still et al. | 514/26 |
| 5,840,485 A | * | 11/1998 | Lebl et al. | 435/6 |

FOREIGN PATENT DOCUMENTS

| | | |
|---|---|---|
| WO | WO9428028 | 12/1994 |
| WO | WO9513538 | 5/1995 |

OTHER PUBLICATIONS

Hirshmann et al ., Tetrahedron., vol. 49., No. 17., pp. 3665–3676., 1993.*
Ohlmeyer et al ., Proc. Natl. Acad. Sci. USA., vol. 90., pp. 10922–10926., Dec. 1993.*
Hans–Jorg Schneider ., Angew. Chem. Int. Ed. Engl., vol. 32., No. 6., pp. 848–850., Jun. 1993.*
Akerfeldt et al ., J. Am. Chem. Soc., vol. 114., pp. 6956–9657., 1992.*
Webb et al., Chem. Soc. Rev., 1993., 393–395.*
Yoon et al ., J. Am. Chem. Soc., 1993., vol. 115., No. 2., pp. 823–824.*
Allen Borchardt et al ., J. Am. Chem. Soc., vol. 116., No. 1., pp. 373–374., 1994.*
Hirschmann et al The first design and synthesis of a steroidal peptidomemetic. The potential value of peptidomimetics in elucidating the bioactive conformation of peptide ligands. Journal of the American Chemical Society 114(24): 9699–9701, 1992.*
Montal et al. "Synporins–synthetic proteins that emulate the pore structure . . . " Proc. Natl. Acad. Sci. USA 87, 6929–6933 (1990).
Grove et al. "Template–Assembled Synthetic Proteins Designed To Adopt a Globular, Four–Helix . . . " J. Am. Chem. Soc. 115, 5919–5924 (1993).

* cited by examiner

Primary Examiner—Padmashri Ponnaluri

(57) ABSTRACT

The invention is directed to synthetic receptor(s) which comprises a polyfunctional organic template covalently linked to two or more oligomers which may independently be the same or different and may independently be straight chain, cyclic or branched. The template may be linked to an identifier which uniquely defines the synthetic receptor. The identifier is a stable chemical molecule or a plurality of stable chemical molecules distinguishable and detectable to picomolar levels or may be an oligonucleotide. In a preferred embodiment, the template is covalently linked to a solid support which is linked to an identifier. In addition, the invention includes methods of preparing synthetic receptors and synthetic receptor libraries. The synthetic library may be linked with identifiers such that the library comprises a plurality of different synthetic receptor members. The invention also provides methods for assaying a synthetic receptor library to determine suitable synthetic receptor(s) which (a) bind an acceptor molecule; (b) exhibit biological activity; (c) which catalyze a reaction or inhibit a catalyzed reaction; and (d) separate compounds in chromatography.

14 Claims, 6 Drawing Sheets

A TYPICAL DECODING GAS CHROMATOGRAPHY SPECTRUM OF A SINGLE BEAD.

SYNTHETIC RECEPTORS

This application is a divisional of U.S. Ser. No. 08/676,143, filed Oct. 24, 1996, which was a national stage filing under 35 USC §371 of international application PCT/US95/00572, filed Jan. 13, 1995, which was, in effect, a continuation-in-part and claimed the priority of U.S. Ser. No. 08/181,628 filed Jan. 13, 1994, the contents of which are incorporated by reference to the subject application.

The invention was made in part with government funds under Grant CHE92-08254 from the National Science Foundation. Therefore, the U.S. Government has certain rights in the invention.

Throughout this application, various references are referred to within parentheses. Disclosure of these publications in their entireties are hereby incorporated by reference into this application to more fully describe the state of the art to which this invention pertains.

BACKGROUND OF THE INVENTION

Receptors are molecules which selectively interact with other molecules. Receptor molecules perform a variety of tasks from selective binding of substrates to catalyzing chemical reactions. One example of a multifunctional receptor molecule is monoclonal antibodies. Monoclonal antibodies bind to other molecules (antigens) with very high selectivity, while in other cases they catalyze chemical reactions by selectively binding the transition states of those chemical reactions. Monoclonal antibodies are used as medicinal and diagnostic agents. Other receptor molecules are used as drug targeting molecules and are sometimes referred to as "magic bullets". In all cases, the receptor molecules effectiveness is dependent upon its ability to bind molecular species (substrates) with high discrimination and selectivity, i.e. not bind other often closely related molecular species.

Antibodies are proteins produced in response to the presence of a foreign substrate (Stryer, L. Biochemistry, 3rd Edition, W. H. Freeman and Company, New York, 1988 and Schultz, P. G. *Acc. Chem. Res.*, 1989, 22, 287). A foreign substrate capable of eliciting antibody formation is called an antigen. Each antibody has a highly specific affinity for the antigen which stimulated its synthesis. The free energy for an antibody binding its antigen is normally from 6–15 kcal/mol. Structure analysis of antibodies have indicated that most have an immunoglobulin structure. Immunoglobulins are flexible Y-Shape molecules and consists of two kinds of polypeptide chains named as light and heavy chains molecular weight (FIG. 1).

While other workers have used combinatorial methods to prepare peptide and oligomer libraries, applicants are the first to apply combinatorial techniques to generate receptor libraries and to methods to identify receptors for specific biological targets.

SUMMARY OF THE INVENTION

The invention is directed to synthetic receptor(s) which comprises a polyfunctional organic template covalently linked to two or more oligomers which may independently be the same or different and may independently be straight chain, cyclic or branched. The template may be linked to an identifier which uniquely defines the synthetic receptor. The identifier is a stable chemical molecule or a plurality of stable chemical molecules distinguishable and detectable to picomolar levels or may be an oligonucleotide. In an preferred embodiment, the template is covalently linked to a solid support which is linked to an identifier.

In addition, the invention includes methods of preparing synthetic receptors and synthetic receptor libraries. The synthetic library may be linked with identifiers such that the library comprises a plurality of different synthetic receptor members. The invention also provides methods for assaying a synthetic receptor library to determine suitable synthetic receptor(s) which (a) bind an acceptor molecule; (b) exhibit biological activity; (c) which catalyze a reaction or inhibit a catalyzed reaction; and (D) separate compounds in chromatography.

BRIEF DESCRIPTION OF THE DRAWINGS

FIG. 1 illustrates an IgG molecule. Both L (light) and H (heavy) chains consist of a variable (V) and constant (C) region. The variable regions of light chain ($V_L$) and heavy chain ($V_H$) are similar in the length and sequence. Immunoglobulin G can be cleaved into three fragments. Two of these fragments bind antigen. They are named as $F_{ab}$ (ab stands for antigen-binding, F for fragments). Each $F_{ab}$ contains one combining site (or antigen-binding site) for antigen, and it has the same binding affinity for antigen as does the whole molecule. The other fragment, called Fc because it crystallizes readily, does not bind an antigen. As indicated in FIG. 1, $F_{ab}$ contains four subunits $V_L$, $V_H$, $C_L$ and $C_{H1}$.

FIG. 2 illustrates the combinatorial method of split-synthesis used to generate 27 tripeptides on a solid support.

FIG. 3 illustrates the process used to monitor reactions on solid supports.

FIG. 4 illustrates the color screening assay using Disperse Red to detect the members of receptor library on beads that bind a substrate. 1 shows the beads before treatment with a colored substrate; 2 represents the color substrate in an organic solvent which is added to the beads and 3 shows the result after one day in a sealed vial to allow for equilibration to occur.

FIG. 5 illustrates the reading of the molecular bar code from a single synthesis bead.

FIG. 6 illustrates a typical gas chromatography spectrum for a single decoded bead. (The binary encoding system with molecular tags was used).

DETAILED DESCRIPTION OF THE INVENTION

Figure 1:
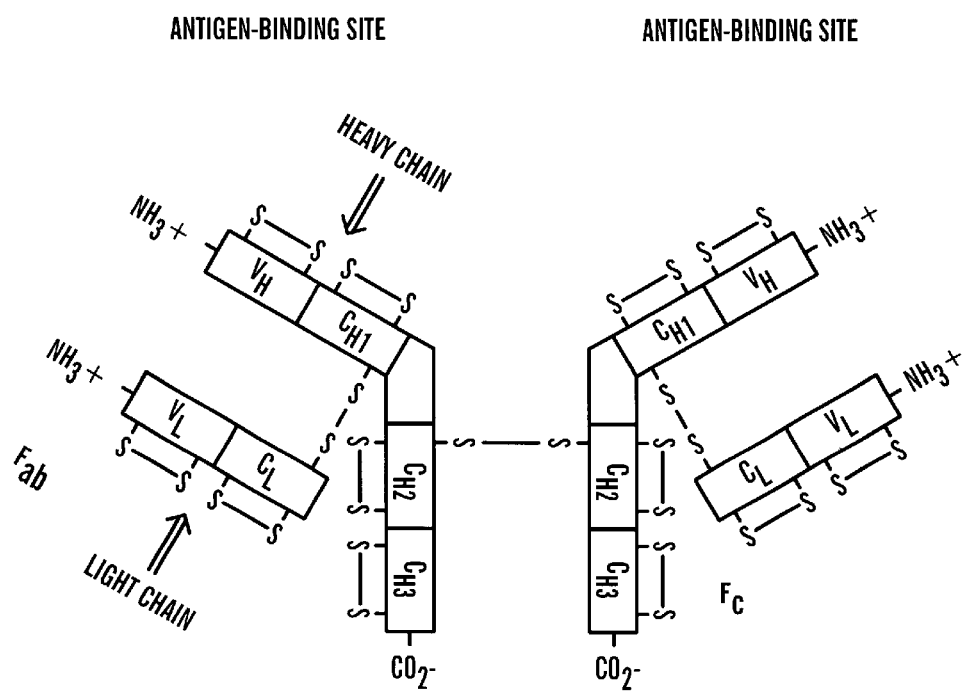
FIG. 1.

As used herein, a polyfunctional organic template may be (a) a monocyclic aliphatic hydrocarbon, (b) a polycyclic aliphatic hydrocarbon, (c) a monocyclic aromatic hydrocarbon, (d) a polycyclic aromatic hydrocarbon, (e) a monocyclic heterocycle, (f) a polycyclic heterocycle, or (g) a macrocycle.

The following fused polycyclic hydrocarbons may be used as templates: pentalene, indene, naphthalene, azulene, heptalene, biphenylene, asym-indacene, sym-indacene, acenaphthylene, fluorene, phenalene, phenanthrene, anthracene, fluoranthene, acephananthrylene, aceanthrylene, triphenylene, pyrene, chrysene and naphthacene (Dean, J. A., ed., Lange's Handbook of Chemistry, Thirteen, Edition, (1985), pages 7–9 and 7–10, MacGraw-Hill, Inc., New York).

The following heterocyclic systems may be used as templates: thiophene, thianthrene, furan, pyran, isobenzofuran, chromene, anthene, phenoxanthiin, 2-H-pyrrole, pyrrole, imidazole, pyrazole, isothiazole, isoxazole, pyridine, pyrazine, pyrimidine, pyridazine, indolizine, isoindole, 3-H-indole, indole, iH-Indazole, purine, 4-H-quinolizine, isoquinoline, quinoline, phthalazine, naphthyridine, quinoxaline, quinazoline, cinnoline, pteridine, 4aH-carbazole, carbazole, β-carboline, phenanthridine, acridine, perimidine, phenanthroline, phenazine and phenarsazine (Dean, J. A., ed., Lange's Handbook of Chemistry, Thirteenth Edition, (1985), pages 7-15–7-17, MacGraw-Hill, Inc., New York).

The following heterocyclic systems may be used as templates: isochroman, chroman, pyrrolidine, pyrazolidine, pyrroline, imidazolidine, imidazoline, pyrazolidine, pyrazoline, piperidine, piperazine, indoline, isoindoline, quinuclidine and morpholine (Dean, J. A., ed., Lange's Handbook of Chemistry, Thirteenth Edition, (1985), pages 7-17–7-18, MacGraw-Hill, Inc., New York).

The following steroid hormones may be used as templates: hydrocortisone, cortisone, corticosterone, aldosterone, deoxycorticosterone, 9αfluorohydrocortisone, prednisolone, methyl prednisolone, dexamethasone, triamcinolone, estradiol 17β, estrone, estriol, progesterone, pregnanediol and testosterone (Dean, J. A., ed., Lange's Handbook of Chemistry, Thirteenth Edition, (1985), pages 7-116–7-19, MacGraw-Hill, Inc., New York).

The following compounds may be used as templates: ferrocenecarboxylic acid and 1,1'-ferrocenedimethanol (Aldrich Catalog/Handbook of Fine Chemicals 1994–1995, Aldrich Chemical Company, Inc., Milwaukee, Wis., page 697).

As used herein, an oligomer includes acyclic or cyclic homomers, heteromers and acyclic or cyclic oligomers include an oligoamide, an oligoester, an oligourea, an oligourethane, an oligoamine, an oligoether, an oligosulfonamide, an oligophosphonamide, an oligophosphonate, an oligophosphate, an oligonucleotide, an oligosaccharide, a peptide oligomer, a cyclophane or a mixture of monomers thereof. An oligomer or portions thereof may also be prepared prior to attachment to the polyfunctional organic template. In addition, the monomers may be coupled together to form units of two or more monomers which are then further joined the polyfunctional organic template.

As used herein, covalently linked is a linkage such as an ester bond, an amide bond, an amine bond, an ether bond, or a linkage through a sulfur, silicon, nitrogen, oxygen, carbon atom, or a covalent bond to any suitable atom.

This invention is directed to a synthetic receptor comprising a polyfunctional organic template covalently linked to two or more oligomer arms which are macrocyclic, acyclic, branched acyclic, cyclic or branched cyclic, or polycyclic which may independently be the same or different and may independently be straight chain, cyclic or branched or combinations thereof. The polyfunctional organic template may be an acyclic, a carbocyclic, a heterocycle, a polycarbocycle, a polycycle hydrocarbon, a polyheterocycle, a macrocyclic polyether, a macrocyclic polyamine, a macrocyclic polyamide, macrocyclic polyester, a macrobicycle, a macrotricycle, a macrotetracycle, a podand, a steroid or

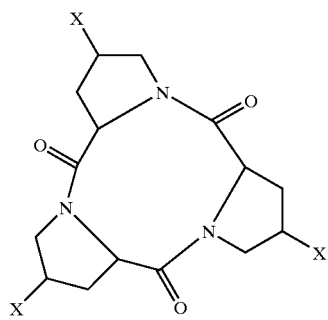

where X=OH, SH or NH$_2$,

Other polyfunctional organic templates include porphyrin rings, cyclodextrins, oligoprolines, calixeranes and macrocycles of the type shown below

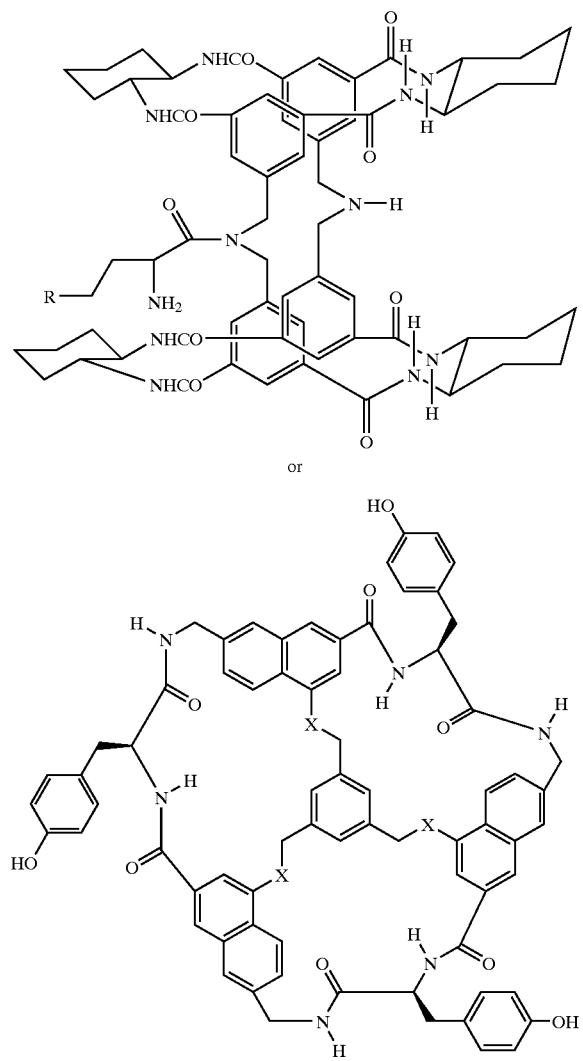

where X=O or S,

In addition the following are also suitable polyfunctional organic templates,

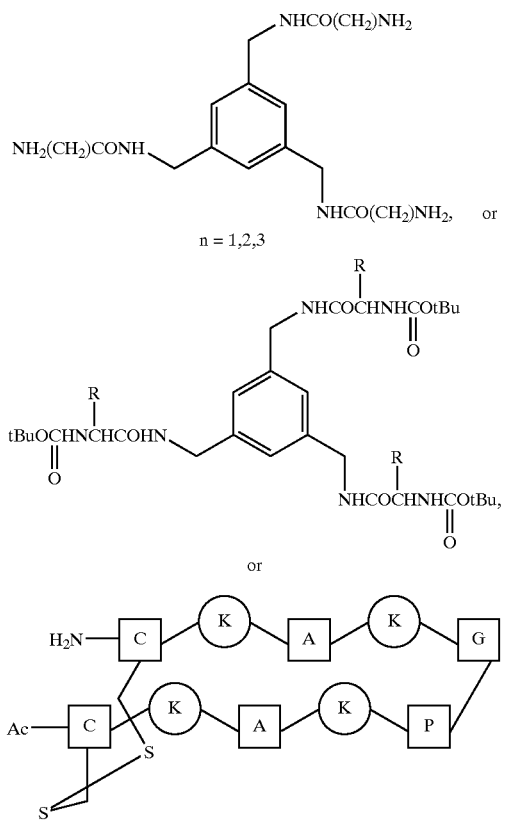

where K=lysine or

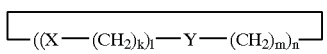

where X, Y=O, S, NH; k, m=2–6; l=0–5; and n=1–6.

The cyclic heterocycle may be a cyclic polypeptide such as cyclosporin

where n=3–20.

The oligomer may be an oligoamide, an oligoester, an oligourea, an oligourethane, an oligoamine, an oligoether, an oligosulfonamide, an oligophosphonamide, an oligophosphonate, an oligophosphate, an oligonucleotide, an oligosaccharide, a peptide oligomer, a cyclophane or a mixture of monomers thereof. Preferably, the oligomers are polypeptides or oligonucleotides. In one preferred embodiment of the invention each oligomer contains less than ten monomers. The oligomers of the synthetic receptor may be the same or different. In another preferred embodiment at least one of the oligomers is a combination of two or more distinct classes of oligomers selected from the group consisting of the above mentioned oligomers. The oligomer may be a heteromer or a homomer. The oligomer may be a cyclic or acyclic.

In one embodiment of the invention the synthetic receptor may be a polyfunctional steroid template covalently linked to two or more peptide oligomers which may independently be the same or different and which may independently be straight chain, cyclic or branched.

The polyfunctional steroid template may be ursodeoxycholic acid, hyodeoxycholic acid, alpha-apocholic acid,

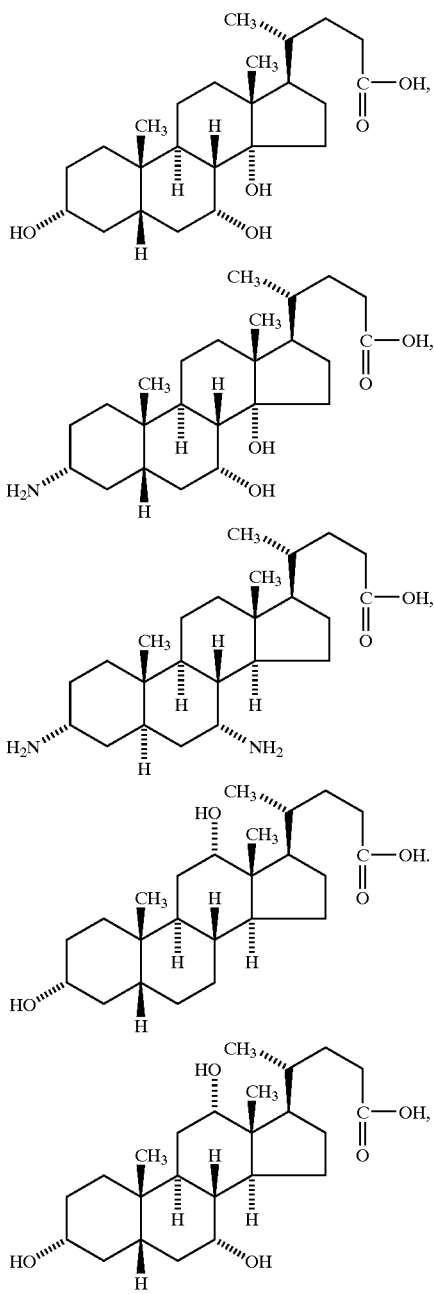

In the preferred embodiment where the synthetic receptor comprises a polyfunctional steroid template the oligomer may be a peptide oligomer comprising at least two amino acids. The template may be further linked to a dye, a fluorescent label or a radioactive label. In addition, the polyfunctional organic template may further be linked to an identifier which uniquely defines the synthetic receptor. The identifier uniquely defines the synthesis and molecular structure of the oligomers of the synthetic receptor. The identifier is a stable chemical molecule or a plurality of stable chemical molecules distinguishable and detectable to picomolar levels or may be an oligonucleotide.

In a preferred embodiment, the synthetic receptor may be a polyfunctional organic template covalently linked to a solid support and to two or more oligomers which may independently be the same or different and which may independently be straight chain, cyclic or branched. The solid support is preferably a particle composed of cellulose, controlled-pore glass, silica gel, polystyrene, PEG-polystyrene, polystyrene optionally cross-linked with divinylbenzene, grafted co-poly, poly-acrylamide, latex, polydimethylacrylamide optionally cross-linked with N,N'-bis-acryloyl ethylene diamine, glass coated with a polymer, or low molecular weight non-cross-linked polystyrene and the particle is a spheroid, a capillary, a hollow fiber, a needle, or a solid fiber.

In the case where the polyfunctional organic template is a steroid, the template is covalently linked to polystyrene, polydimethylacrylamide or PEG-polystyrene particles. The solid support is further linked to an identifier which uniquely identifies the synthetic receptor covalently linked to the solid support.

The invention provides methods to prepare libraries comprising a plurality of distinct synthetic receptors, where the libraries comprise at least 100 distinct synthetic receptors. The libraries comprise at least $10^3$ distinct synthetic receptors and preferably as many as $10^6$ or $10^9$ distinct synthetic receptor members. Preferably, the receptor library contains at least $10^6$ members. The libraries may have synthetic receptors where the polyfunctional organic template is an acyclic hydrocarbon, a monocyclic aliphatic hydrocarbon, a polycyclic aliphatic hydrocarbon, a monocyclic aromatic hydrocarbon, a polycyclic aromatic hydrocarbon, a monocyclic heterocycle, a polycyclic heterocycle, a macrocycle or a steroid. In one embodiment the synthetic receptors of the libraries are covalently linked to a solid support. The libraries may have at least 100 unique solid supports. The solid support is linked to an identifier or identifiers which uniquely define the synthetic receptors. In other preferred embodiments, the polyfunctional organic template is further linked to an identifier or identifiers.

In addition, the invention provides a method of preparing a synthetic receptor library with identifiers comprising a plurality of different synthetic receptor members. Each synthetic receptor library member may be a solid support having a single type of synthetic receptor attached. The method having the following steps: a) reacting the solid supports in a reaction vessel with a polyfunctional organic template; b) apportioning the solid supports with the attached polyfunctional organic template among a plurality of reaction vessels; c) reacting the polyfunctional organic template on a solid support in each reaction vessel with a first oligomer monomer; d) reacting the solid supports in each reaction vessel with a first identifier; e) pooling the solid supports; f) apportioning the pooled supports among a plurality of reaction vessels; g) reacting the polyfunctional organic template on solid support in each reaction vessel with a second oligomer monomer; h) reacting the pooled solid supports in each reaction vessel with a second identifier; and i) repeating steps (e) through (h) from at least one to twenty times for each oligomer of the synthetic receptor. The identifier molecules or combinations thereof used for the methods described herein are preferably different for each iteration.

The invention also provides a method comprising the steps of: a) preparing a bifunctional solid support containing a first type of active site blocked with a first type of protecting group and a second type of active site blocked with a second type of protecting group; b) reacting the solid support with an activator to remove the first type of protecting group thereby exposing the first type of active site; c) coupling a protected polyfunctional organic template to the first type of active site; d) reacting the protected polyfunctional organic template with an activator to remove the first type of protecting group thereby exposing the first type of active site; e) coupling a protected oligomer monomer to the deprotected polyfunctional organic template; f) reacting the solid support with an activator to remove the second type of protecting group thereby exposing the second type of active site; g) coupling a protected identifier to the second type of active site; and h) repeating steps (d) through (g) from one to twenty times for each oligomer of the synthetic receptor.

The invention also provides the method comprising the steps of: a) coupling a protected polyfunctional organic template to a solid support; b) reacting the protected polyfunctional organic template with an activator to remove the protecting group thereby exposing the active site; c) coupling a protected oligomer monomer to the deprotected polyfunctional organic template; d) coupling an identifier to the solid support; and e) repeating steps (b) through (d) from one to twenty times for each oligomer of the synthetic receptor. In the method above steps (c) and (d) may be further combined with pooling and apportioning steps so as to practice split synthesis as outlined in FIG. 2.

Another embodiment of the invention is a method of preparing a synthetic receptor with one or more identifiers which comprises a polyfunctional organic template covalently linked to two or more oligomers which may independently be the same or different and which may independently be straight chain, cyclic or branched and one or more identifiers attached to the solid support which define the molecular structure of the oligomers of the synthetic receptor, the method comprising the steps of: a) coupling a protected polyfunctional organic template to a solid support; b) reacting the protected polyfunctional organic template with an activator to remove the protecting group thereby exposing the active site; c) coupling a protected oligomer monomer to the deprotected polyfunctional organic template; d) coupling an identifier to the solid support; and e) repeating steps (b) through (d) from one to twenty times for each oligomer of the synthetic receptor.

The invention also provides a method of preparing a synthetic receptor library with identifiers comprises a plurality of different synthetic receptor members, wherein each synthetic receptor library member comprising a solid support having attached thereto a single type of synthetic receptor which comprises a polyfunctional organic template covalently linked to two or more oligomers which may be independently the same or different and which may independently be straight chain, cyclic or branched and one or more identifiers which define the synthetic receptor, the method comprising the steps of: a) apportioning the solid supports among a plurality of reaction vessels; b) reacting the solid supports in each reaction vessel with a first oligomer monomer; c) reacting the solid supports in each reaction vessel with a first identifier; d) pooling the solid supports; e) apportioning the pooled supports among a plurality of reaction vessels; f) reacting solid supports in each reaction vessel with a second oligomer monomer; g) reacting the pooled solid supports in each reaction vessel with a second identifier; h) repeating steps (d) through (g) from at least one to twenty times for each oligomer; and i) reacting the solid supports in each reaction vessel with a polyfunctional organic template. A method of preparing a synthetic receptor with one or more identifiers which comprises a polyfunctional organic template covalently linked to two or more oligomers which may independently be the same or different and which may independently be straight chain, cyclic or branched and one or more identifiers attached to the solid support which define the molecular structure of the oligomers of the synthetic receptor, the method comprising the steps of: a) prepare a multifunctional solid support containing a active sites blocked with protecting groups; b) reacting the solid support with an activator to remove a first type of protecting group thereby exposing a first type of active site; c) coupling a protected oligomer monomer to the first type of active site of the solid support; d) react the solid support with an activator to remove a second type of protecting group thereby exposing a second type of active site; e) coupling a protected identifier to the second type of active site; and f) repeating steps (b) through (e) from one to twenty times for each oligomer; g) reacting the protected oligomer on the solid support with an activator to remove the protecting group thereby exposing an active site; h) coupling a polyfunctional organic template to the active site.

In the methods described above the identifier is a stable chemical molecule or a plurality of stable chemical molecules distinguishable and detectable to picomolar levels or an oligonucleotide. The solid supports coupled to the polyfunctional organic templates in each reaction vessel may first be reacted with an identifier and then the polyfunctional organic templates on the solid supports may be reacted with an oligomer monomer.

The invention also provides a method for assaying a synthetic receptor library to determine a suitable synthetic receptor for an acceptor molecule of interest, the method comprising the steps: a) generating a synthetic receptor library; b) contacting the synthetic receptor library with the acceptor molecule of interest under conditions such that the acceptor molecule interacts and binds to one or more suitable synthetic receptors of the synthetic receptor library; c) isolating the suitable synthetic receptor(s) that exhibit binding to the acceptor molecule; and d) determining the molecular structure of the suitable synthetic receptor(s).

The acceptor molecule introduced for the assay may be linked to a label. The label attached to the acceptor molecule introduced identifies the suitable synthetic receptor(s) interacting with the acceptor molecule. The label may be a dye, a fluorescent label or a radioactive label. The suitable synthetic receptor(s) identified in the assay may be used as a chromatographic separation agent.

The acceptor molecule of interest may be selected from the following, an antibody, a peptide, a protein, a carbohydrate, a nucleic acid, a lipid, a drug, a metal or a small molecule. In the case of a peptide acceptor, the peptide may be an adrenocorticotropic hormone and fragments, angiotensin, atrial natriuretic, bradykinin, chemotatic, dynorphin, endorphins and beta-lipotropin fragments, enkephalin, enzyme inhibitors, fibronectin fragments, gastrointestinal, growth hormone releasing peptides, luteinizing hormone releasing peptide, melanocyte stimulating hormone, neurotensin, opioid, oxytocin, vasopressin, vasotocin, parathyroid hormone and fragments, protein kinase, somatostatin, substance P. In the case where the protein acceptor molecule is a growth hormone it may be selected from the group comprising human, bovine, porcine, avian, ovine, piscine, or equine growth hormone, and polypeptide analogs thereof having the biological activity of the corresponding naturally occurring growth hormone. In addition, the protein which is a growth factor may be IL-1, IL-2, IL-3, IL-4, IL-5, IL-6, IL-7, IL-8, IL-9, IL-10, IL-11, IL-12, IL-13, IL-14, EGF, aFGF, bFGF, TGF-beta1, TGF-beta2, TGF-beta3, G-CSF, GM-CSF, M-CSF, EGF, IGF-I, IFN, IL, LIF, KGF, OSM, PLSF, TNF, cytokines, kit ligand, EPO, transforming growth factor, nerve growth factor, brain derived growth factor, neurotrophin-3, neurotrophin-4, heptaocyte growth factor. The protein may also be a receptor for any of the above peptides, or growth factors. The acceptor molecule may also be present on whole cells, viruses or bacteria. Other acceptor molecules include molecules on a cancer cell associated with the following cancers, melanoma, lip, tongue, mouth, pharynx, esophagus, stomach, small intestine, colon, rectal, liver, pancreas, larynx, lung, bone, connective tissue, skin, breast, uterus, ovary, prostate, testis, bladder, kidney, eye, brain, central nervous system, endocrine glands, blood and lymph tissues or leukemia. The invention is also directed to a synthetic receptor selectively binding an acceptor molecule in the presence of other different acceptor molecules.

The invention further provides a method for assaying a synthetic receptor library for suitable synthetic receptor(s) that exhibit biological activity, the method comprising the steps of: a) generating a synthetic receptor library; b) detecting the biological activity of suitable synthetic receptors of the synthetic receptor library in situ; c) isolating the suitable synthetic receptor(s) that exhibit the biological activity; and d) determining the molecular structure of the suitable synthetic receptor(s) isolated in step (c).

The biological activity of interest is, e.g. cytotoxicity, antitumor activity, antibacterial activity, antiviral activity, antifungal activity, anti-parasite activity, growth factor activity, growth inhibitory activity, hormone activity, neurotransmitter activity, immunomodulator activity, regulatory activity or enzymatic activity. In the assays described above the activity of interest is determined at nanomolar concentrations and the synthetic receptor(s) detected may be of use as a therapeutic agents or as a diagnostic agents. Furthermore, a suitable synthetic receptor may selectively bind to a transition state analogue.

Another embodiment of the invention includes a method for assaying a synthetic receptor library for a suitable synthetic receptor(s) which catalyzes a reaction, the method comprising the steps of: a) generating a synthetic receptor library; b) introducing to the synthetic receptor library a substrate such that a catalyzed reaction product is determined; c) isolating the suitable synthetic receptor(s) that exhibits catalytic activity; and d) determining the molecular structure the suitable synthetic receptor(s) isolated in step (c).

In addition, the invention provides a method for assaying a synthetic receptor library for a suitable synthetic receptor (s) which inhibits an enzyme-catalyzed reaction, the method comprising the steps of: a) generating a synthetic receptor library; b) introducing to the synthetic receptor library an enzyme that catalyzes a reaction of interest in situ; c) detecting inhibition by a suitable synthetic receptor(s) of the enzyme-catalyzed reaction of interest in situ; d) isolating the suitable synthetic receptor(s) that exhibits inhibition of enzyme catalyzed reaction of interest in situ; and e) determining the molecular structure the suitable synthetic receptor(s) isolated in step (c).

This invention will also be directed to the use of the receptors to detect a drug and in the detection of an illicit drug, i.e., a narcotic, an anabolic steroid.

This invention includes a method for creating new synthetic receptors and libraries of synthetic receptors which can mimic monoclonal antibodies has been developed.

The synthetic receptor molecules herein, may selectively bind almost any desired substrate. Using combinatorial synthesis large libraries of synthetic receptors can be generated. Once prepared the libraries of synthetic receptors can be used to screen for synthetic receptor members that have a desired characteristic. A library of synthetic receptors is synthesized using combinatorial techniques. The synthetic receptor library may be prepared by any of the known methods for combinatorial synthesis (G. Jung and A. G. Beck-Sickinger, *Angew. Chem. Int. Ed. Engl.* 1992, 367–383, 31; M. R. Pavia, T. K. Sawyer and W. H. Moos, *Bioorg. Med. Chem. Lett.*, 1993, 387–396, 3).

The synthetic receptor may have one of the following structures, where the polyfunctional organic template is be prepared, such detectable substrates are referred to as labeled substrates.

The synthetic receptor library is then assayed to find those members of the library which have the desired interaction with the labeled substrate. In the case where the desired interaction is binding to the substrate, the synthetic receptor library is mixed with a solution of the labeled substrate and

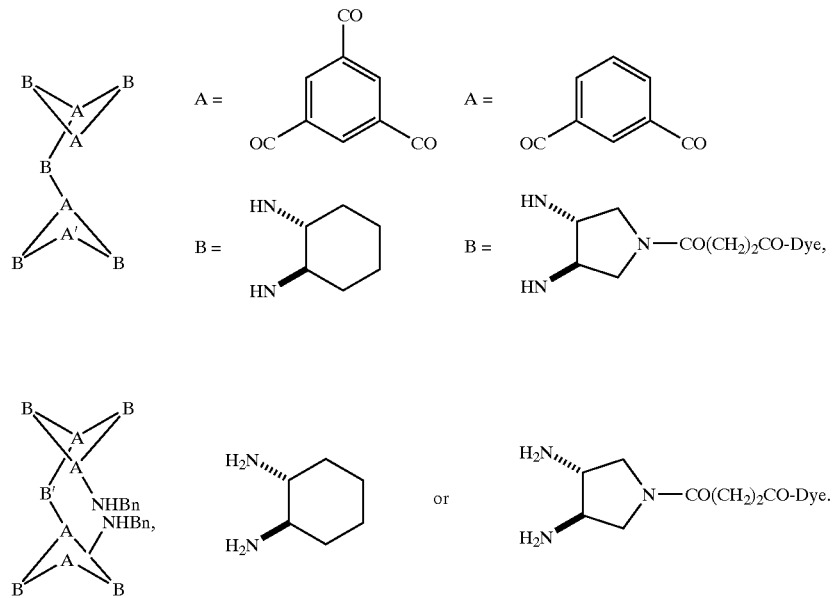

The synthetic receptors members have the following general formula (Scheme 1):

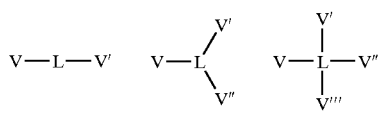

Scheme 1. General formula for synthetic receptor members. where L is a polyfunctional organic template which is chemically bonded to V, V', etc. which are oligomers.

Scheme 1 is a subset of the general formula L-$(-V^N)_M$. A synthetic receptor library will consist of a collection of such synthetic receptor molecules (i.e. a library) is having a variety of different oligomers V, V', etc. groups. In some cases it will be desirable to attach the polyfunctional organic template to a solid support particle (P) as diagrammed below such that any given solid support particle has only one type of synthetic receptor (i.e. one type of synthetic receptor member of the library) bound to it.

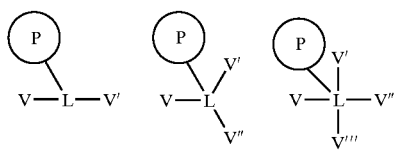

Scheme 2. Solid support particle attached to a synthetic receptor molecule.

A substrate of interest, detectable at nanomolar levels by way of its color, its fluorescence, its radioactivity, etc., may those library members that bind to the labeled substrate are selected. This procedure is particularly simple when the synthetic receptor library members are bound to a solid support as shown in Scheme 2. In that case, solid support particles having receptors which bind the labeled substrate accumulate color or fluorescence or radioactivity (depending on the nature of the label used). Depending on the concentration of the labeled substrate used, the assay can be adjusted to detect binding of any desired strength: for example, if the amount of labeled substrate in the presence of the receptor library is adjusted to give a 100 µM concentration of free (unbound) labeled substrate, then assay will only detect template-substrate binding with association constants (k) of $(100\ \mu M)^{-1}$ or greater.

In the case where the desired interaction is catalysis of a chemical reaction, the synthetic receptor library is mixed with a solution of the labeled substrate and those library members are selected which catalyze the conversion of the substrate to a reaction product. Detection of reaction products for synthetic receptor library members having catalytic activity may be determined for example by HPLC (high performance liquid chromatography) analysis. The synthetic receptors showing catalytic activity are then isolated from the library.

Once the desired synthetic receptor library member(s) is selected using the assay as described above, then the structure of the synthetic receptor(s) is determined. The selected synthetic receptor(s) can be used in affinity chromatography (Eveleigh, J. W. & Levy, D. E. Immunochemical characteristics and preparative application of agarose-based immunosorbents. J. Solid Biochem. (2) 45–78, 1977). The following coupling gels may be used in affinity chromatography: NHS-activated SUPEROSE 12™, Activated CH SEPHAROSE 4B™, CNBr-activated SEPHAROSE 4B™, ECH SEPHAROSE 4B™, Epoxy-activated SEPHAROSE 6B™, EAH SEPHAROSE 4B™, AGAROSE™ Adipic Acid Hydrazide, Thiopropyl SEPHAROSE 6B™ and Activated Thiol SEPHAROSE™ 4B (Pharmacia LKB Biotechnology Products Catalog 1991, Pharmacia LKB Biotechnology, Piscataway, N.J., pages 7–8). Additional coupling gels such as HITRAP™ NHS-activated, CNBr-activated SEPHAROSE 4B™, Expoxy-activated SEPHAROSE 6B™, EAH SEPHAROSE 4B™, AGAROSE™ Adipic Acid Hydrazide and Thiopropyl SEPHAROSE 6B™ may be used in affinity chromatography (Atlas of Practical Purification: Chromatography Media to Meet Your Needs, Pharmacia Biotech, pages 24–25, 31).

The templates (L) will desirably have limited conformational mobility and functionality oriented in such a way that the variable oligomeric chains are directed toward nearby regions of space. Some selected examples of such suitable templates include polyfunctional steroids such as steroidal diols, triols and amines. The oligomeric chains are indicated by V or V'. In these figures, R represents any stable organic functionality (and is unimportant to the properties of the template) in the case of the free template library while R represents a functional group with a connection to a solid support (e.g. —(CH$_2$)$_2$CONH-polymer) in the case of the solid phase supported library.

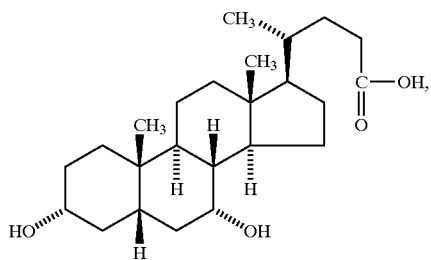

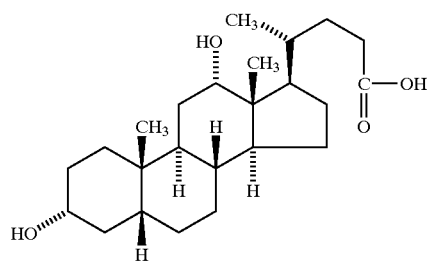

Steroidal diol templates

Steroidal diol templates

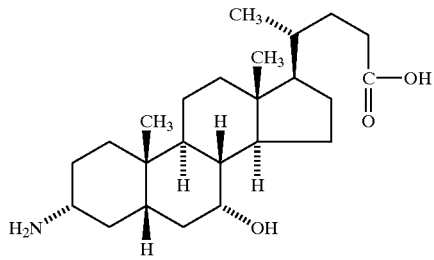

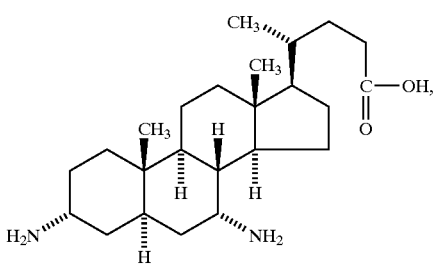

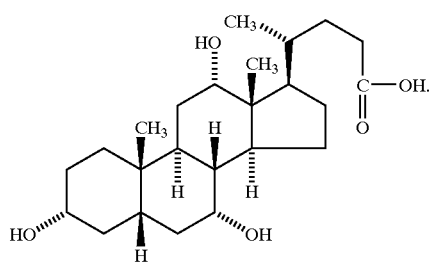

Cholic acid template (a steroidal triol).

Cholic acid could form the basis for a triple chained template (this is an example of the LVV'V'' described above). In the cholic acid-based templates described above, the D-ring side chain served as a convenient appendage with which to bind the template to a solid support. With other templates, such an appendage may be absent but may be inserted by adding a trifunctional material to one of the template functional groups. This material would provide two remaining groups which could be used for attaching the solid support (R) and the variable oligomer (V, V', etc).

The effect of having a rigid polyfunctional organic template is well illustrated by the binding observed for Leu Enkephalin shown below. This peptidosteroidal receptor library has an estimated 300 sequences binding Leu Enkaphalin, with a $K_{D-Max}$=75–85 $\mu$M

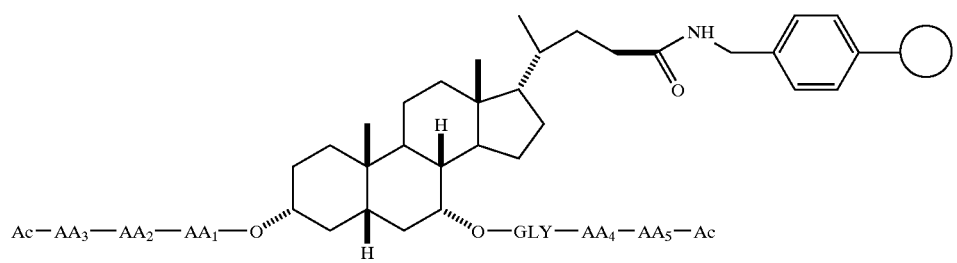

However, the less rigid example shown below, has a estimated 2000 sequences bind Leu Enkaphalin, $K_{D-Max}=$ 200 μM.

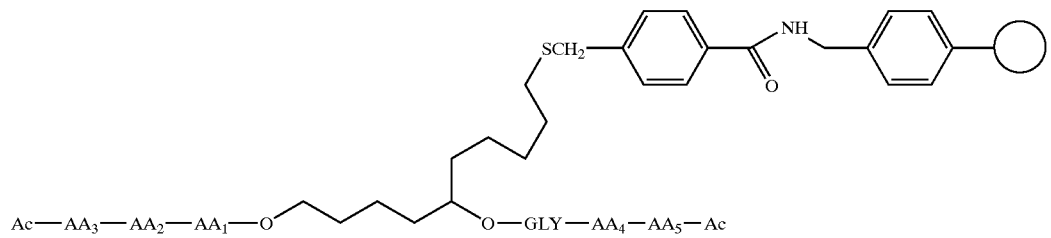

A variety of nonsteroidal templates could also be used to produce synthetic receptor libraries based, for example, on macrocyclic cores. This structure is generally based on a known template (Yoon and Still, *J. Am. Chem. Soc.*, 115, 823, 1993). In general, templates can include any di-, tri- or tetra-, etc. functionalized organic structure where the functionality allows attachment of the variable oligomeric chains (V, V', etc).

For the variable oligomeric chains (V, V', etc), any oligomer can be used. Thus V, V', etc can consist of oligoamides, oligoesters, oligoureas, oligourethanes, oligoamines, oligoethers, oligosulfonamides, oligophosphonamides, oligophosphonates, oligophosphates, etc. as well as mixed oligomers composed of mixtures of the foregoing functionalities. The chain can be either linear, cyclic or branched and can incorporate both cyclic and acyclic segments. Branched oligomers will be utilized to generate larger binding sites which should give tighter and more selective substrate binding. Oligomers composed of conformationally rigid fragments or segments are of interest because they help preorganize the template and therefore increase its selectivity. In a preferred embodiment the oligomers are polypeptides, cyclophanes or a mixture thereof.

As discussed, combinatorial synthesis is a convenient method to generate a receptor library containing a diverse and numerous number of molecules. These combinatorial synthetic techniques include, multi-pin method (Geysen, H. M.; Meloen, R. and Barteling, S. *Proc. Natl. Acad. Sci. USA*, 1984, 81, 3998; Geysen et al., *Proc. Natl. Acad. Sci. U.S.A.*, 1985, 82, 178; WO 84/03564; WO 86/06487; PCT/AU85/ 00165 (WO 86/00991), U.S. Pat. No. 5,133,866), tea-bag method (U.S. Pat. No. 4,631,211; Houghton et al., *Int. J. Peptide Protein Res.*, 1986, 27, 673; Houghton et al., *Biotechniques*, 1986, 4, 6, 522; Houghten, R. A. *Proc. Natl. Acad. Sci. USA*, 1985, 82, 5131; WO 92/09300; WO 92/09300), cellulose-paper method (Frank, R. and Doering, R. *Tetrahedron Lett.* 1988, 44, 6031), light-directed method (also termed as VLSIPS method, Fodor, S. P. A.; Read, J. L.; Pirrung, M. C.; Stryer, L.; Lu, A. T. and Soias, D. *Science* 1991, 251, 767,; U.S. Pat. No. 5,143,854; WO 90/15070; WO 92/10092) and the split-synthesis method (Lam, K.; Salvon, S.; Hersh, E.; Hruby, V.; Kazmierski, W. and Knapp, R. *Nature*, 1991, 354, 82; WO 92/00091, WO 93/06121). However, the split-synthesis method is superior to the other methods as it offers a procedure involving the systematic synthesis and screening of oligomer libraries of defined structure.

Figure 2:
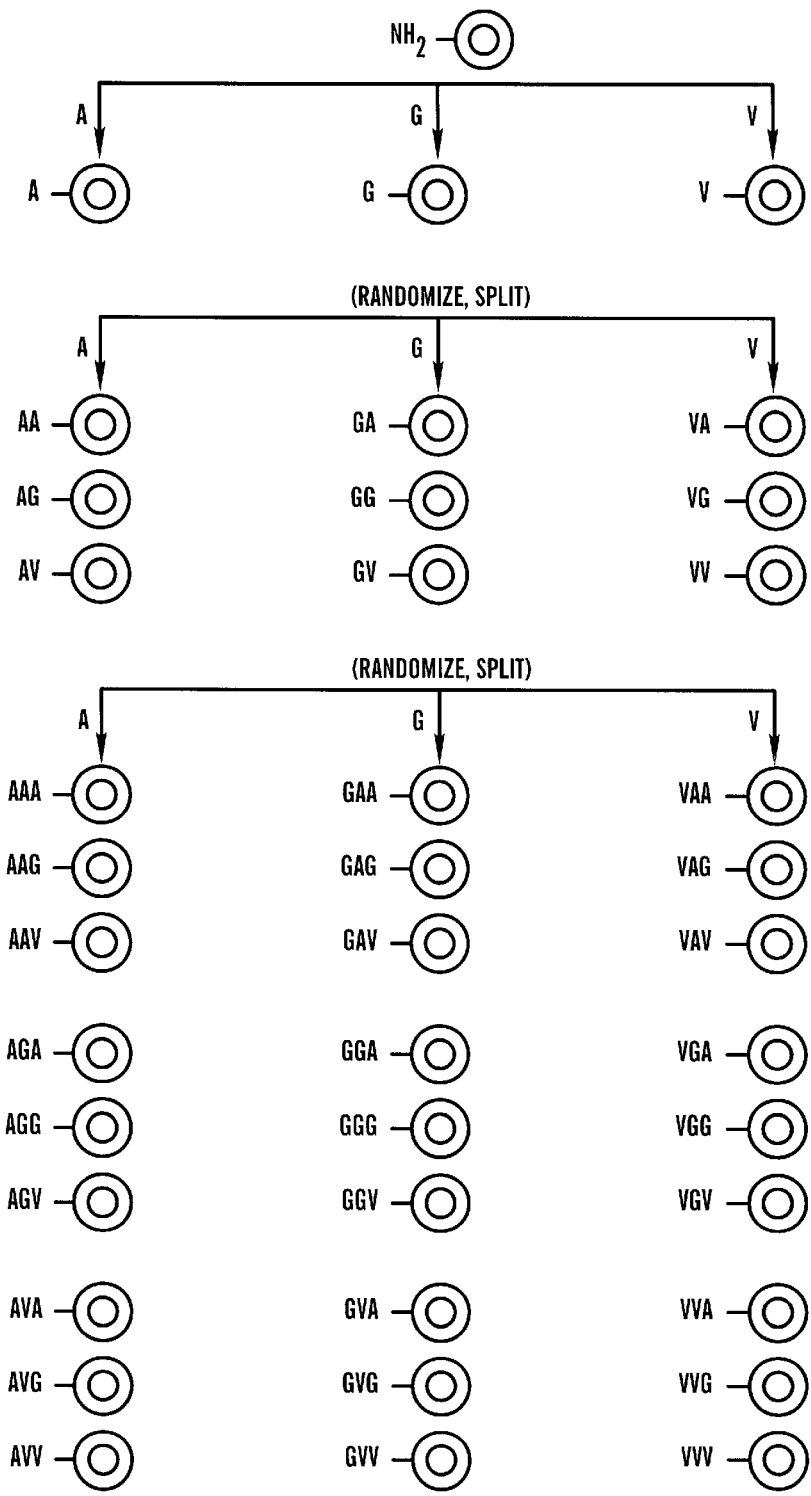
FIG. 2.

The procedure for split synthesis involves creating a large oligomer library consisting of thousands to billions of different molecules. The molecules may be attached to particles such as beads, with each bead containing a single oligomer sequence and with the collection representing numerous combinations of possible random oligomer sequences. The "one-bead, one-oligomer sequence" concept can be achieved easily by separating and mixing beads during the synthesis. FIG. 2 demonstrates the synthesis of 27 tripeptides comprising alanine (A), glycine (G) and valine (V) by the split-synthesis method. At the end of the synthesis, each bead has only one product from a specific reaction sequence.

Since the amount of products on each bead is normally 50–200 pmol, the structure elucidation of such small amount of products restricts the split-synthesis method to the synthesis of nucleotides or peptides composed of natural amino acids. The split-synthesis method alone fails to provide access to other libraries comprising unnatural monomers.

In order to solve the structure elucidation problem, readable tags (oligonucleotide tag or peptide tag) are cosynthesized to encode the series of steps and reagents used in the synthesis of each library element (Brenner, S. and Lerner, R. A. *Proc. Natl. Acad. Sci, USA*, 1992, 89, 5381; Kerr, J. M.; Banville, S. C. and Zuckermann, R. N. *J.Am. Chem. Soc.* 1993, 115, 2529). Once a library element is selected by certain assay, its structure can be identified by sequencing its peptide tag or oligonucleotide tag after PCR amplification. The main problem with the above encoding methods is the at the tagging structures are chemically liable and destroyed by many of the reagents and conditions normally associated with the synthetic organic chemistry. Furthermore, the oligonucleotide or peptide tags may themselves associate with biological receptors and confuse binding or enzymatic assays. Recently, an alternative encoding method was developed using molecular tags (M. J. H. Ohlmeyer, R. N. Swanson, L. W. Dillard, J. C. Reader, G. Asouline, R. Kobayashi, M. Wigler and W. C. Still, (1993) *Proc. Natl. Acad. Sci. USA*, 90, 10922–10926; WO 94/08051). This technique makes use of highly sensitive, chemically inert molecular tags and a binary encoding scheme. This method provides a practical solution for the construction of large, chemically diverse libraries.

The binary encoding scheme allows the encoding of the maximum amount of information by using the minimum number of tag molecules. For example, a simple combinatorial synthesis using any of 7 different reagents in each step is carried out. These seven different reagents can be designated by three tag molecules through the binary encoding scheme as tag 1 for reagent, tag 2 for reagent 2, tag 1 and tag 2 for reagent 3, . . . , tag 1, tag 2 and tag 3 for reagent 7. This letter description can be simply translated into binary numerical description as 001 (reagent 1), 010 (reagent 2), 011 (reagent 3), . . . , 111 (reagent 7). The binary encoding scheme only requires 3N tag molecules to encode $7^N$ different final products in the library, where N is the number of chemical steps for synthesis of the library.

The tag molecules used are shown below.

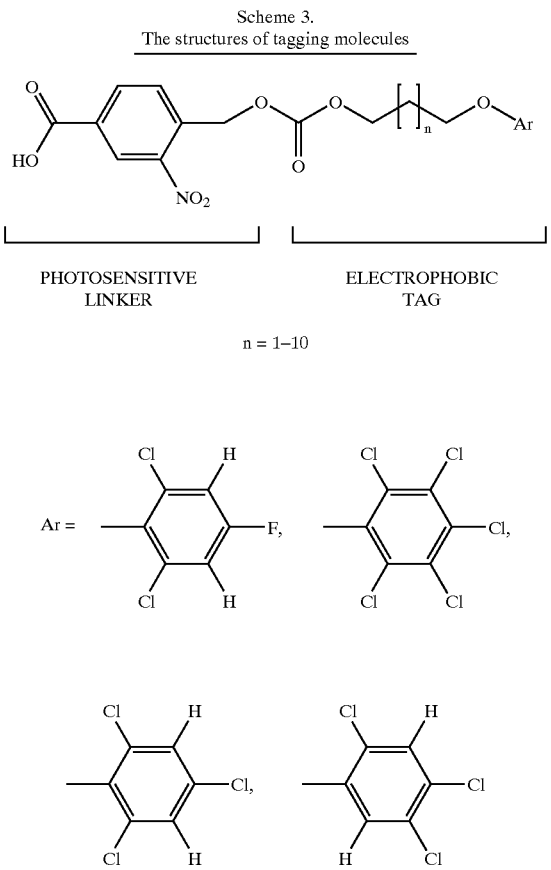

The molecular tags are varied by different lengths of the hydrocarbon (n=0–10) and three different electrophores (Ar). With a photocleavable linker (Patchornik, A.; Amit, B. and Woodward, R. B. *J. Am. Chem. Soc.* 1970, 92, 6333), the electrophoric tags can be easily liberated from solid-supports by irradiation with light of wavelength longer than 320 nm. The liberated alcohols are then silylated by N,O-bis (trimethylsilyl) acetamide in N,N-Dimethylformamide. The resulting silyl ethers are well separated by capillary GC and selectively detected by EC electron capture) at levels <1 pmol. More than 20 tagging molecules were prepared which allow encoding of up to $2^{20}$ different synthesis. Using the above binary encoding scheme and tagging molecules, two different receptor libraries composed of 10,000–20,000 receptor members have been prepared. Through color screening with a labeled substrate (vide infra), it was possible to select several synthetic receptor molecules from the libraries as the mimics of the antibody against Enkephalin i.e., "synthetic antibodies", which is conceptually represented below.

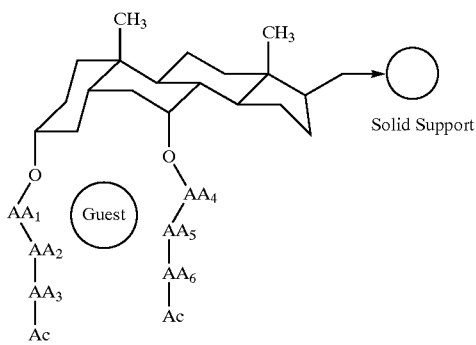

A binding constant with free energy of formation ΔG to the acceptor of 5 Kcal/mol to 12 Kcal/mol is desirable, in some cases the preferred free energy of formation ΔG may be 9 Kcal/mol to 12 Kcal/mol and in other cases a ΔG of 8 Kcal/mol to 15 Kcal/mol is desirable.

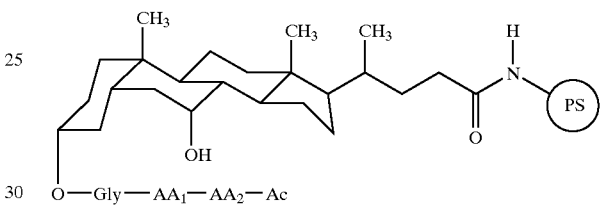

As part of the synthesis of double-armed peptidosteroidal receptor library (Boyce, Li, Nestler, Suenaga and Still, *J. Am. Chem. Soc.*, 1994, 116, 7955, the single-armed peptidosteroidal receptor library was prepared as shown above. Ten different amino acids at $AA_1$ and $AA_2$ were used resulting in 100 different receptors. When the library was treated with Disperse Red-dyed Leu Enkephalin no binding was found.

The following experimental details are set forth to aid in an understanding of the invention, and are not intended, and should not be construed, to limit in any way the invention set forth in the claims which follow thereafter.

EXAMPLE 1

General Procedures

All the reactions on solid support were carried out in Merrifield reaction vessels. The reaction vessels were silylated by the treatment of 10% trimethylsilylchloride in toluene at room temperature for 1 hour followed by washing and drying prior to use. A Burrell Wrist Action Shaker was used to shake reaction vessels. Anhydrous solvents were used for reaction, which were either distilled or purchased from Aldrich Inc. Solvents used for washing beads were reagent grade. Photolysis of beads was carried out in MeOH or N,N-Dimethylformamide by irradiating beads under UV light with a Model UVL-56 (UVP, Inc., San Gabriel, Calif.) Ultraviolet lamp at 366 nm. Aminomethyl resin was purchased from Balchem, Inc. (200–400 mesh, 0.6 mmol/g) or Sigma, Inc. (100–200 mesh, 1.1 mmol/g[18]).

The tag molecules used for encoding the synthesis of the libraries are shown in Scheme 3. They are simply named as $C_n$, 2,4,5 $Cl_3$; $C_n$, 2,4,6 $Cl_3$ and $C_n$, $Cl_5$ stand for 2,4,5 trichloro phenyl, 2,4,6, trichloro phenyl and pentachloro phenyl groups respectively.

Amino acids used for the synthesis of the following libraries were Alanine, Valine, Leucine, Phenylalanine, Proline, Serine, Threonine, Lysine, Aspartic acid and Glutamic acid. Alanine, Valine, Leucine, Phenylalanine and Proline are 9-Fluorenylmethyloxycarbonyl for α-amino group and t-butyl for side-chain protection. Lysine is protected by 9-Fluorenylmethyloxycarbonyl for α-amino group and tert-Butyloxycarbonyl for ξ-amino group.

Figure 3:
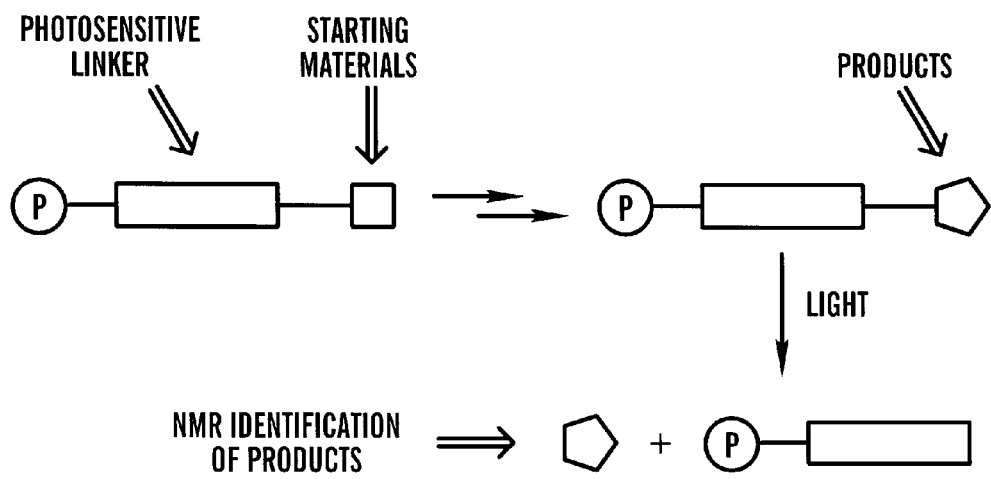
FIG. 3.

During the solution synthesis, the progress of reactions can be easily monitored by checking TLC of reaction mixtures. However, almost no reactions except peptide formation can be monitored during the solid-phase synthesis. Solid-phase synthesis normally requires the use of a large excess of reactants and multiple couplings to convert starting materials to products. It is therefore much more difficult to do selective functionalization on a solid-phase support than in solution due to the lack of detecting tools for monitoring reactions and the necessity of using large excess reactants during the synthesis. In order to monitor the reactions other than peptide formation on solid supports, a "detectable solid phase synthesis" method was developed which is shown in FIG. 3.

By introducing a photosensitive linker between the template and solid support, reactions can be monitored by nuclear magnetic resonance (spectroscopy) of the free products liberated from beads by photolysis, the synthesis of detectable beads is described below.

The Gly-library was constructed on aminomethyl resin (200–400 mesh, 0.6 mmol/g) which was purchased from Bachem, Inc.

The Pro-library was constructed on aminomethyl resin (100–200 mesh, 0.9 mmol/g) which was purchased from Sigma, Inc.

LIST OF ABBREVIATIONS

| | |
|---|---|
| AA | Amino Acid |
| Ac | Acetyl |
| $Ac_2O$ | Acetic anhydride |
| Ala | Alanine |
| aq. | Aqueous |
| Asp | Aspartic acid |
| atm. | Atmosphere |
| 9-BBN | 9-Borabicyclo[3.3.1]nonane |
| Boc | tert-Butyloxycarbonyl |
| n-Bu | n-Butyl |
| t-Bu | tert-Butyl |
| cat. | Catalytic amount |
| CSA | Camphorsulfonic acid |
| DCC | Dicyclohexylcarbodiimide |
| DET | Diethyl tartrate |
| DIAD | Diisopropyl azodicarboxylate |
| DIBAH | Diisobutylaluminum hydride |
| DIPEA | Diisopropylethyl amine |
| DIPT | Diisopropyl tartrate |
| DMAP | 4-Dimethylaminopyridine |
| DMF | N,N-Dimethylformamide |
| DMSO | Dimethyl sulfoxide |
| EC | Electron capture (detector) |

-continued

LIST OF ABBREVIATIONS

| | |
|---|---|
| EDC | $N$-Ethyl-$N^1$-(3-dimethylaminopropyl)carbodiimide |
| ee | Enantiomeric excess |
| eq. | Equivalent |
| Et | Ethyl |
| EtOAc | Ethyl acetate |
| EtOH | Ethanol |
| FMOC | 9-Fluorenylmethyloxycarbonyl |
| GC | Gas Chromatography |
| Glu | Glutamic acid |
| h | Hour or hours |
| HOAc | Acetic acid |
| HOBT | 1-hydroxybenzotriazole |
| HMPA | Hexamethylphosphoric triamide |
| hv | Light |
| i-Pr | Isopropyl |
| i-PrOH | 2-Propanol |
| LAH | Lithium aluminum hydride |
| LDA | Lithium diisopropylamide |
| Leu | Leucine |
| Lys | Lysine |
| MCPBA | m-Chloroperoxybenzoic acid |
| Me | Methyl |
| MeOH | Methanol |
| MeCN | Acetonitrile |
| mol | MOLE |
| mp | Melting Point |
| Ms | Mesyl (methanesulfonyl) |
| NMO | N-Methylmorpholine N-oxide |
| NMR | Nuclear magnetic resonance (spectroscopy) |
| --P | Amino methyl resin support |
| Ph | Phenyl |
| Phe | Phenylalanine |
| Pro | Proline |
| Py | Pyridine |
| r.t. | Room temperature |
| TBDMS | tert-Butyldimethylsilyl |
| TEA | Triethyl amine |
| TFA | Trifluoroacetic acid |
| THF | Tetrahydrofuran |
| THP | Tetrahydropyran |
| Thr | Threonine |
| TLC | Thin layer chromatography |
| TMS | Trimethylsilyl |
| Ser | Serine |
| Val | Valine |
| uv | Ultraviolet (spectroscopy) |

The Synthesis of Detectable Beads

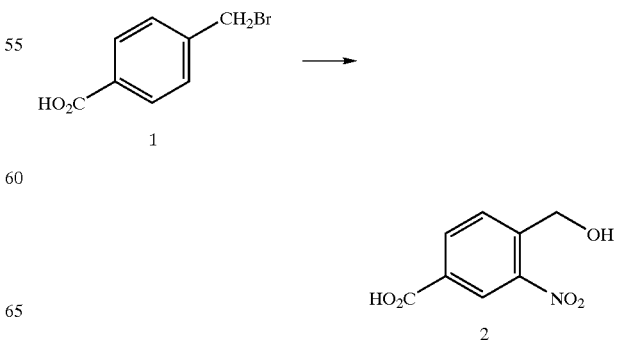

α-Bromo-p-toluic acid (21.5 g, 100 mmol) was added in five equal portions to 90% HNO₃ (250 mL) at −10° C. The reaction mixtures were stirred at −10° C. for 3 h and poured into ice-water. After stirring at room temperature for 3 h, the white precipitate was filtered, collected and dried by air overnight to give ortho-nitro α-bromo-p-toluic acid (22.2 g, 85%) as slightly yellow solid.

To the potassium carbonate aqueous solution (35.0 g, 200 ML H₂O) was added ortho-nitro α-bromo p-toluic acid (13.1 g, 50 mmol). The homogenous solution was stirred at room temperature overnight and then cooled at 0° C. Concentrated HCl was added until PH=1. The resulting white precipitate was filtered, collected and dried in air to afford 2 as white solid (8.9 g, 95% mmol). The filtrate was extracted with ethyl acetate three times. The combined extracts were washed with brine, dried over MgSO₄, filtered and concentrated to give another portion of 2 as slightly yellow solid (1.0 g, 5%).

¹H NMR (CD₃OD) 4.98 (s, 2H), 7.96 (d, 1H, J=8.12 Hz), 8.25 (dd, 1H, J=1.72, 8.16 Hz), 8.56 (d, 1H, J=1.64 Hz). ¹³C NMR (CD₃OD) 61.85, 126.56, 129.70, 131.96, 135.11, 143.94, 148.29, 167.39.

IR (KBr) 3450, 2953, 1726, 1152, 1080 cm⁻¹.

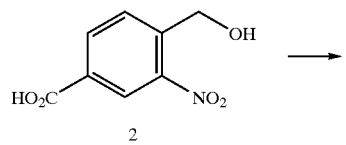

2

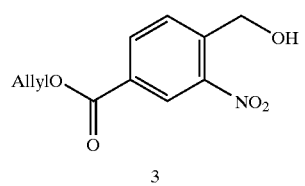

3

To the ortho nitro α-hydroxy p-toluic acid (9.9 g, 50 mmol) in allyl alcohol (200 mL) was added p-TsOH H₂O (850 mg, 5 mmol). The mixtures were under flux for 24 h and concentrated to dryness. The resulting residue was then dissolved in 500 mL ethyl acetate, washed with saturated sodium bicarbonate solution and dried over MgSO₄. Removal of ethyl acetate and recrystalization from MeOH to give the allyl ester 3 as a slightly yellow solid (9.3 g, 95%).

¹H NMR (CDCl₃) 2.61 (bs. 1H), 4.86 (dt, 2H, J=5.84, 1.40 Hz), 5.07 (s, 2H), 5.33 (dd, 1H, J=10.4, 1.28 Hz), 5.43 (dd, 1H, J=17.24, 1.48 Hz), 6.21 (ddt, 1H, J=5.76, 10.44, 17.24 Hz), 7.92 (d, 1H. J=8.08 Hz), 8.31 (dd, 1H, J=1.64, 8.08 Hz), 8.72 (d, 1H, J=1.60 Hz).

¹³C NMR (CDCl₃) 61.94, 66.30, 118.99, 125.89, 129.49, 130.67, 131.58, 134.27, 141.54, 147.66, 164.04.

IR (KBr) 3500, 3089, 2946, 1726, 1649, 1622, 1537, 1492, 1406, 1281, 1253, 1189, 1151, 1125, 1080, 1049, 974, 853, 832, 774 cm⁻¹.

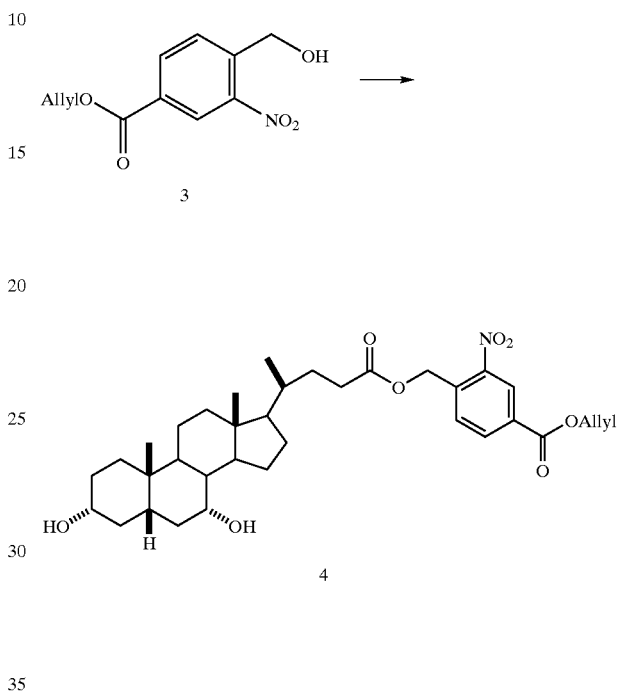

To a solution of chenodeoxycholic acid (3.94 g, 10 mmol) and ortho nitro α-hydroxy p-toluic acid (2.4 g, 10 mmol) in CH₂Cl₂ (50 ml) was added N-Ethyl-N'-(3-dimethylaminopropyl)carbodiimide (2.9 g, 15 mmol) and 4-dimethylaminopyridine (120 mg, 1 mmol). The reaction mixture was stirred at room temperature for 2 hours. After which time the reaction mixture was diluted with 200 mL ethyl acetate, washed with 1N HCl twice and brine once, dried over MgSO₄ and concentrated in vacuo. The crude product was subjected to flash chromatography to yield the desired product 4 as a white foam solid (5.3 g, 87%, R_f=0.75, 25% hexanes in EtOAc)

¹H NMR (CDCl₃ 0.65 (s, 3H), 0.89 (s, 3H), 0.94 (d, 3H, J=6.24 Hz), 0.96–2.05 (m, 25H), 2.19 (dt. 1H, J=12.8, 12.8 Hz), 2.35 (m, 1H), 2.47 (m, 1H), 3.45 (m, 1H), 3.84 (m, 1H), 4.86 (d, 2H, J=5.76 Hz), 5.33 (d, 1H, J=10.36 Hz), 5.42 (dd, 1H, J=17.16, 1.28 Hz), 5.55 (s, 2H), 6.03 (ddt, 1H, J=5.76, 10.52, 17.12 Hz), 7.69 (d, 1H, J=8.12 Hz), 8.30 (dd, 1H, J=1.6, 8.12 Hz), 8.74 (d, 1H, J=1.6 Hz).

¹³C NMR (CDCl₃) 11.77, 18.27, 20.62, 2.74, 23.67. 28.09, 30.75, 30.94, 31.02, 32.94, 34.76, 35.07, 35.29, 35.40, 39.53, 39.71, 39.96, 41.60, 42.73, 50.50, 55.86, 62.38, 66.35, 68.43, 71.95, 119.07, 126.01, 129.20, 131.19, 131.56, 134.01, 136.83, 147.84, 163.80, 173.22.

IR (KBr) 3500, 3089, 2945, 1726, 1649, 1622, 1537, 1492, 1406, 1348, 1151, 1080, 1049, 974, 743 cm⁻¹

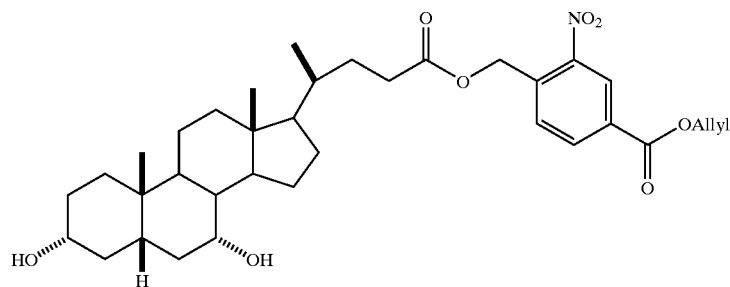

4

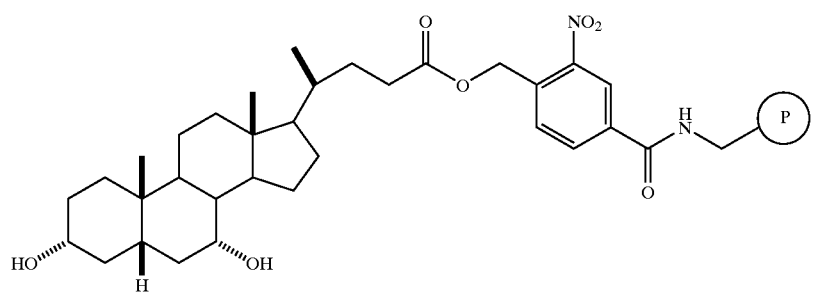

5

The allyl ester 4 (3.0 g, 4.9 mmol) and Pd(PPh₃)₄ (115 mg. 0.1 mmol) in 15 mL CH₂Cl₂ was cooled to 0° C. Pyrrolidine (840 μL, 10 mmol) in 2 mL CH₂Cl₂ was added dropwise. The reaction mixtures were stirred at 0° C. for 45 min, and then EtOAc (200 mL) and 1N HCl (50 mL) were added. The organic layer was washed with brine, dried over MgSO₄, filtered and concentrated to afford the free acid as a slightly yellow solid.

To the pre-swelled aminomethyl resin (3.0 g, 0.6 mmol/g) in a 50 mL reaction vessel were added the above free acid 1-hydroxybenzotriazole (675 mg, 5 mmol) and DIC (660 μL, 4.5 mmol) in 30 mL DMF. The reaction mixtures were shaken at room temperature for 6–8 h until the Kaiser is test indicated the completion of the reaction. The reagents were filtered, and beads were washed with 3×N,N-dimethylformamide, 3×i-PrOH and 5×CH₂Cl₂, and then dried to give the detectable beads 5 (4.0 g).

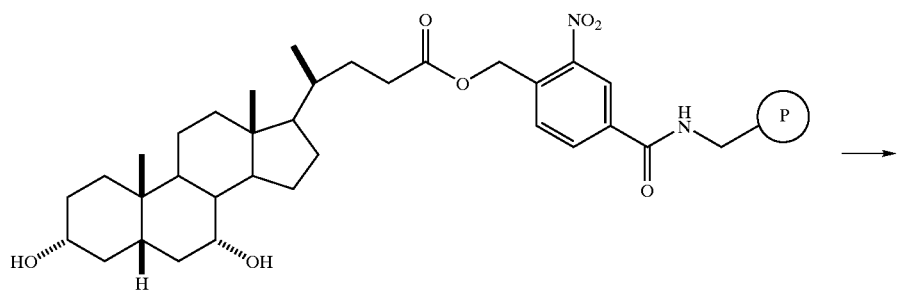

5

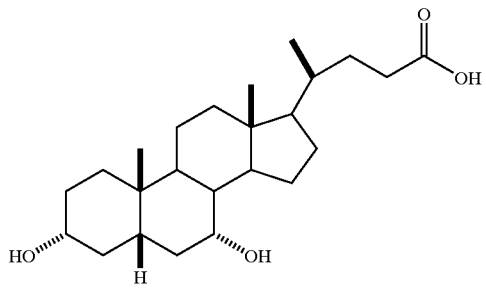

The above beads (5) (40 mg) and 500 µL CH$_3$OH in a capped 1 mL test tube under Ultraviolet light for 12 hours at room temperature. The beads were filtered, and the filtrate was concentrated to give a white solid whose NMR spectrum indicated that only chenodeoxycholic acid was formed.

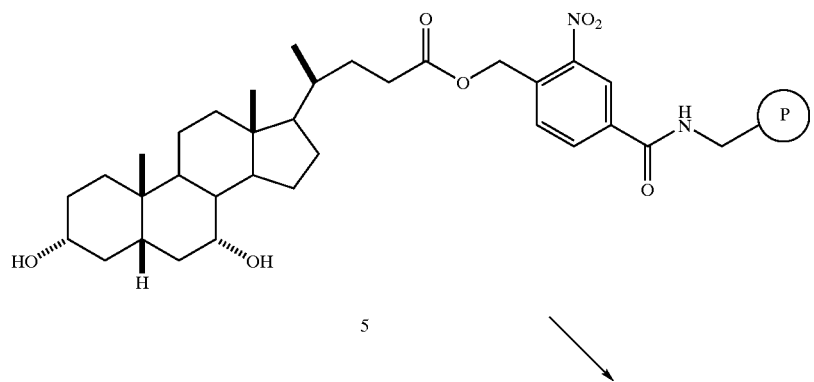

5 then washed with 3×N,N-dimethylformamide to give C$_3$—OGly-9-fluorenylmethyloxycarbonyl, C$_7$—OH beads.

To the above beads was added 1:1 N,N-dimethylformamide/piperidine (5 mL). The reaction vessel was shaken at room temperature for 30 min, and then the

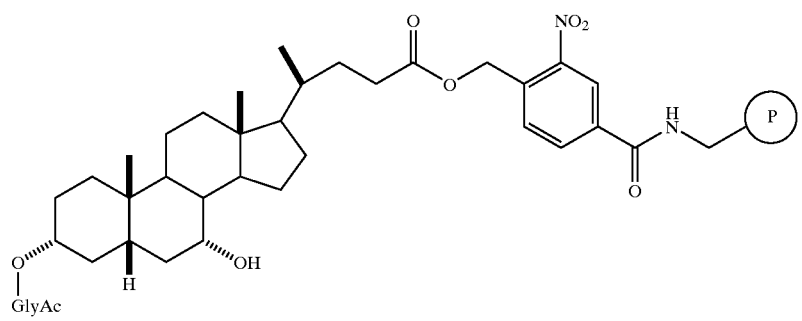

9

To the detectable beads 5 (200 mg, 0.9 mmol) was added diisopropylethyl amine (110 µL, 0.6 mmol) in 1 mL N,N-dimethylformamide followed by the addition of 9-fluorenylmethyloxycarbonyl-GlyF (135 mg, 0.45 mmol) in 1 mL N,N-dimethylformamide. After shaking at room temperature for 3 hours, reagents were filtered and the beads were washed with N,N-dimethylformamide (5 mL) once. The resulting beads were retreated with diisopropylethyl amine and 9-fluorenylmethyloxycarbonyl-GlyF in N,N-dimethylformamide twice under the same conditions and beads were washed with 4×N,N-dimethylformamide followed by the treatment of HOAc (27 µL, 0.45 mmol), 1-hydroxybenzotriazole (68 mg, 0.5 mmol) and DIC (70 µL, 0.45 mmol) in 2 mL N,N-dimethylformamide. The reaction mixtures were under shaking for 2 hours until the Kaiser test indicated the completion of the reaction. The beads were then thoroughly washed with 2×N,N-dimethylformamide (5 mL, 2 min each), 3×i-PrOH (5 mL, 2 min each) and 5×CH$_2$Cl$_2$ (5 mL, 2 min each), and then dried on pump to afford beads 9.

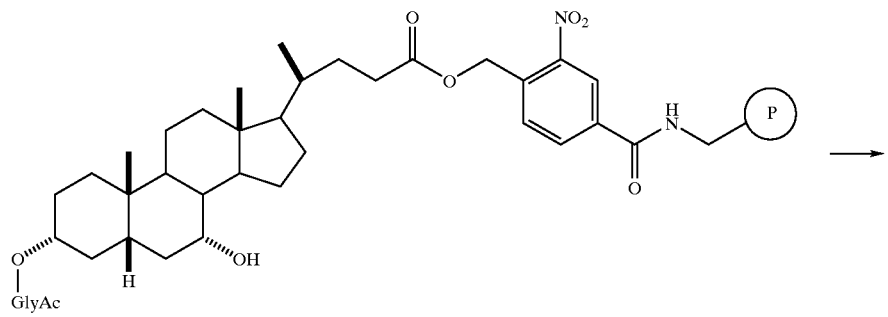
9
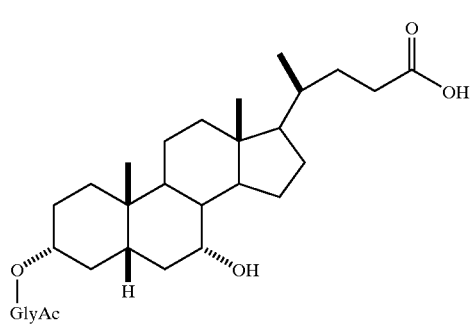
10
The resulting beads 9 (40~50 mg) and 500 μL N,N-dimethylformamide in a capped 1 mL test tube were under Ultraviolet light for 12 hours. The beads were filtered, and the filtrate was concentrated to give 10 as a white solid. The NMR spectrum of 10 indicates that the selectivity for esterification of $C_3$—OH and $C_7$—OH is 19:1.
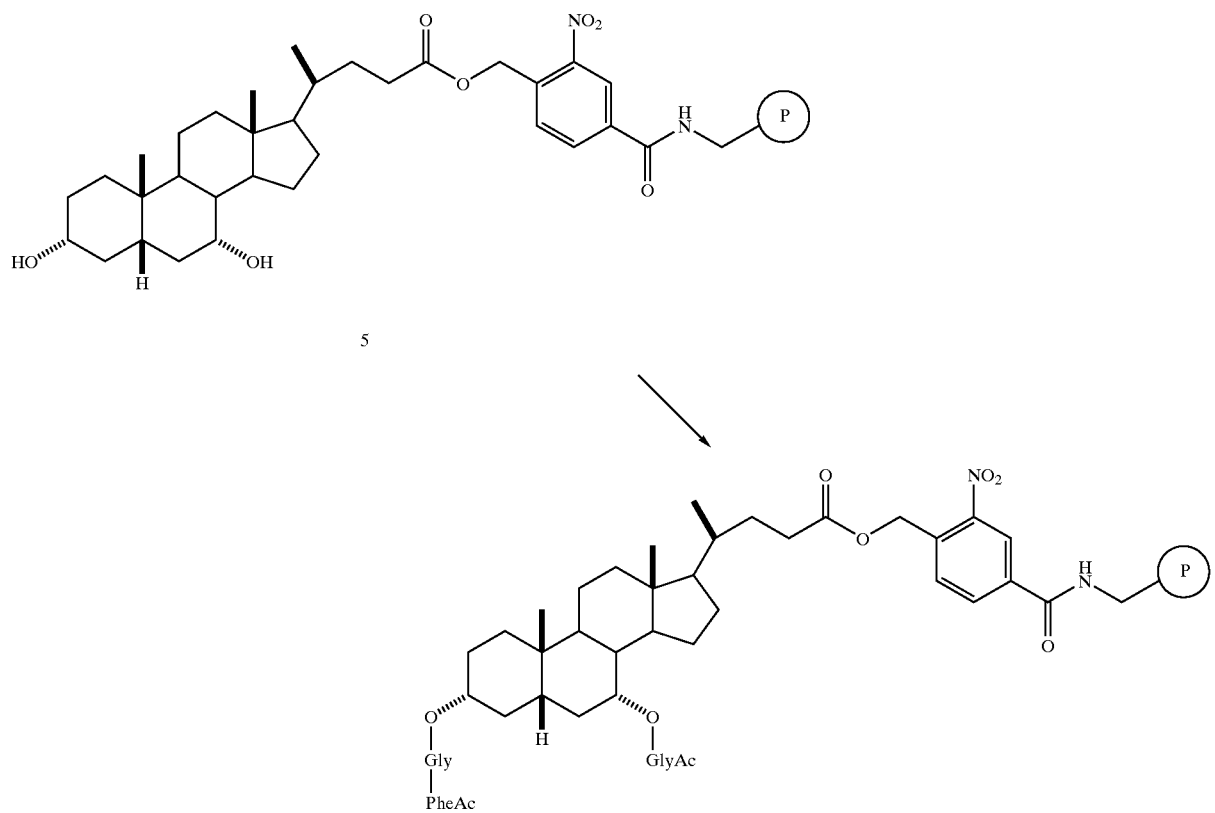

To the detachable beads 5 (200 mg, 0.09 mmol) was added diisopropylethyl amine (110 μL, 0.6 mmol) in 1 mL N,N-dimethylformamide followed by the addition of 9-fluorenylmethyloxycarbonyl-GlyF (135 mg, 0.45 mmol) in 1 mL N,N-dimethylformamide. After shaking at room temperature for 3 hours, reagents were filtered and the beads were washed with N,N-dimethylformamide (5 mL) once. The resulting beads were retreated with diisopropylethyl amine and 9-fluroenylmethyloxycarbonyl-GlyF in N,N-dimethylformamide twice under the same conditions and then washed with 3×N,N-dimethylformamide to give $C_3$—OGly-9-fluorenylmethyloxycarbonyl, $C_7$—OH beads.

The above beads were again treated with 1:1 N,N-dimethylformamide/piperidine (5 mL) to remove the 9-Fluorenylmethyloxycarbonyl-protecting group. The reaction vessel was shaken at room temperature for 30 min, and the beads were washed with 4×N,N-dimethylformamide, and the treated with 9-Fluorenylmethyloxycarbonyl-Phenylalanine (97 mg, 0.25 mmol), 1-hydroxybenzotriazole (35 mg, 0.25 mmol) and DIC (40 μl, 0.25 mmol) in 2 mL N,N-dimethylformamide. The reaction mixtures were under shaking for 3 hours until the Kaiser test indicated the completion of the reaction. The beads were then thoroughly washed with 2×N,N-dimethylformamide (5 mL, 2 min each) and 5×$CH_2Cl_2$ (5 mL, 2 min each) to give the $C_3$—OGlyPhenylalanine-9-Fluorenylmethyloxycarbonyl, $C_7$—OH beads.

To the above beads was added 1:1 N,N-dimethylformamide/piperidine (5 mL). After under shaking at room temperature for 30 min, the beads were washed with 4×N,N-dimethylformamide and treated with HOAc (27 μL, 0.45 mmol), 1-hydroxybenzotriazole (35 mg, 0.25 mmol) and DIC (70 μL, 0.45 mmol) in 2 mL N,N-dimethylformamide. The reaction mixtures were under shaking for 2 h until the Kaiser test indicated the completion of the reaction. The beads were then thoroughly washed with 2×N,N-dimethylformamide (5 mL, 2 min each) and 5×$CH_2Cl_2$ (5 mL, 2 min each) to give the $C_3$—OGlyPhenylalanineAc, $C_7$—OH beads.

To the above beads were added diisopropylethyl amine (110 μL, 0.6 mmol) and 4-Dimethylaminopyridine (11 mg, 0.09 mmol) in 1 mL N,N-dimethylformamide followed by the addition of 9-Fluorenylmethyloxycarbonyl-GlyF (135 mg, 0.45 mmol) in 1 mL N,N-dimethylformamide. After shaking at room temperature for 1 h, reagents were filtered and the beads were washed with N,N-dimethylformamide (5 mL) once. The resulting beads were retreated with diisopropylethyl amine, 4-Dimethylaminopyridine and 9-Fluorenylmethyloxycarbonyl-GlyF in N,N-dimethylformamide twice under the same conditions and then washed with 3×N,N-dimethylformamide (5 mL, 2 min each), 3×i-PrOH (5 mL, 2 min each) and 5 $CH_2Cl_2$ (5 mL, 2 min each), and then dried on pump to afford beads 11.

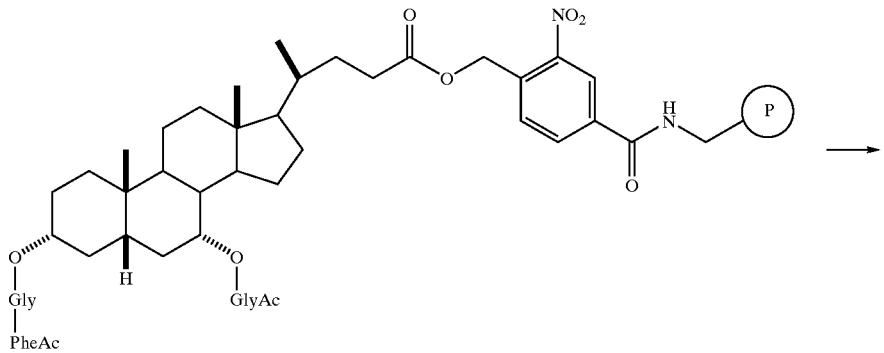

11

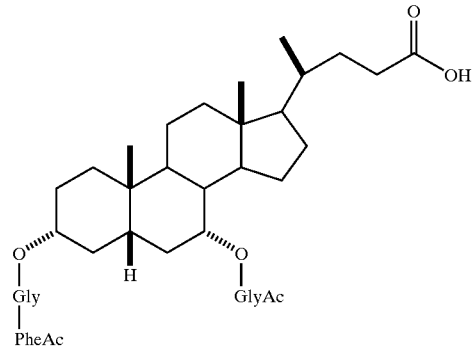

12

The above beads 11 (40~50 mg) and 500 μL N,N-dimethylformamide in a capped 1 mL test tube were under Ultraviolet light for 12 hours. The beads were filtered, and the filtrate was concentrated to give 12 as a waxy solid. The NMR spectrum of 12 indicates that the acylation of $C_7$—OH is complete.

The Synthesis of a Gly-library

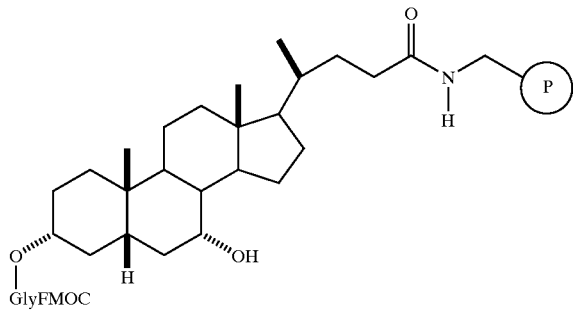

GlyFMOC

To a 50 mL reaction vessel containing 3 g aminomethyl resin (1.8 mmol, 0.6 mmol/g) were added 1-hydroxybenzotriazole (675 mg, 5.0 mmol), DIC (660 µL, 4.5 mmol) and chenodeoxycholic acid (1.8 g, 4.5 mmol) in 30 mL N,N-dimethylformamide. The reaction mixtures were shaken at room temperature for 6–8 hours. When the Kaiser test indicated the completion of the coupling reaction, the beads in the reaction vessel were washed twice with N,N-dimethylformamide (30 mL each), three times with $CH_2Cl_2$ (30 mL each) and dried.

To the above chenodeoxycholic acid beads was added diisopropylethyl amine (2.1 mL, 12 mmol) in N,N-dimethylformamide (20 mL) followed by the addition of 9-Fluorenylmethyloxycarbonyl-GlyF (2.7 g, 9 mmol) in 10 mL N,N-dimethylformamide. After shaking at room temperature for 3 hours, solvents and reagents were filtered and the beads were washed with N,N-dimethylformamide once. The resulting beads were retreated with diisopropylethyl amine and 9-Fluorenylmethyloxycarbonyl twice under the same conditions, and then washed with 3×N,N-dimethylformamide, 2×i-PrOH, 5×$CH_2Cl_2$, and dried on pump to give the $C_3$—OGly9-Fluorenylmethyloxycarbonyl, $C_7$—OH beads (4.2 g, slightly yellow beads).

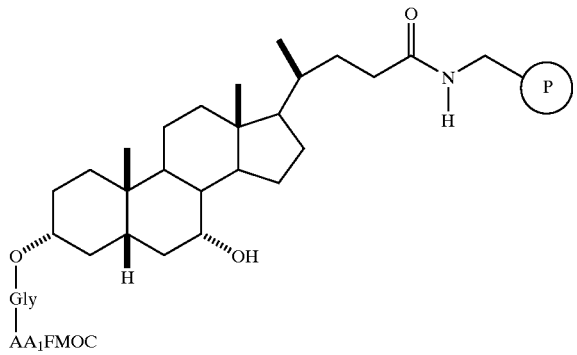

Gly
|
$AA_1$FMOC

Ten equal portions (400 mg~0.18 mmol) of the above resin were placed into ten reaction vessels which were labeled as 1,2,3, . . . ,10. Each portion of the beads was treated with 1:1 N,N-dimethylformamide/piperidine (10 mL) at room temperature for 30 min to remove 9-Fluorenylmethyloxycarbonyl protecting group. After washing the beads with 4×N,N-dimethylformamide, the tag molecules ($1.8×10^{-3}$ mmol), 1-hydroxybenzotriazole (13 mg, 0.09 mmol, 50 eq.) and DIC (14 µL, 0.09 mmol, 50 eq.) in 4 mL N,N-dimethylformamide were added to each reaction vessel as the following manner:

| Tag molecules | Amount of Tags | Reaction vessel |
|---|---|---|
| $T_1$, $C_3$, 2, 4, 5 $Cl_3$ | 0.9 mg | 1 |
| $T_2$, $C_3$, 2, 4, 6 $Cl_3$ | 0.9 mg | 2 |
| $T_3$, $C_4$, 2, 4, 5 $Cl_3$ | 0.9 mg | 3 |
| $T_4$, $C_5$, 2, 4, 6 $Cl_3$ | 0.9 mg | 4 |
| $T_1$, $T_2$ | $T_1$, 0.9 mg; $T_2$, 0.9 mg | 5 |
| $T_1$, $T_3$ | $T_1$, 0.9 mg; $T_3$, 0.9 mg | 6 |
| $T_1$, $T_4$ | $T_1$, 0.9 mg; $T_4$, 0.9 mg | 7 |
| $T_2$, $T_3$ | $T_1$, 0.9 mg; $T_3$, 0.9 mg | 8 |
| $T_2$, $T_4$ | $T_1$, 0.9 mg; $T_4$, 0.9 mg | 9 |
| $T_3$, $T_4$ | $T_1$, 0.9 mg; $T_4$, 0.9 mg | 10 |

After shaking 12 hours in the dark at room temperature, the beads in each reaction vessel were washed with 4×$CH_2Cl_2$ (10 mL each). 9-Fluorenylmethyloxycarbonyl-Amino acid (0.5 mmol), 1-hydroxybenzotriazole (70 mg, 0.5 mmol) and DIC (80 µL, 0.5 mmol) in 4 mL N,N-dimethylformamide were added to each reaction vessels as:

| Amino Acids | Amount of Amino Acids | Reaction Vessel |
|---|---|---|
| Ala | 156 mg | 1 |
| Val | 170 mg | 2 |
| Leu | 177 mg | 3 |
| Phe | 194 mg | 4 |
| Pro | 170 mg | 5 |
| Ser | 192 mg | 6 |
| Thr | 199 mg | 7 |
| Lys | 235 mg | 8 |
| Glu | 213 mg | 9 |
| Asp | 206 mg | 10 |

When the resin in each reaction vessel gave a negative Kaiser test, normally 3 h at room temperature. Then the beads in ten reaction vessels were combined in a 50 mL reaction vessel and washed with 2×N,N-dimethylformamide (30 mL, 2 min each), 3×i-PrOH (30 mL, 2 min each) and 5×$CH_2Cl_2$ (30 mL, 2 min each), and dried to afford $C_3$—OGly$AA_1$-9-Fluorenylmethyloxycarbonyl, $C_7$—OH beads.

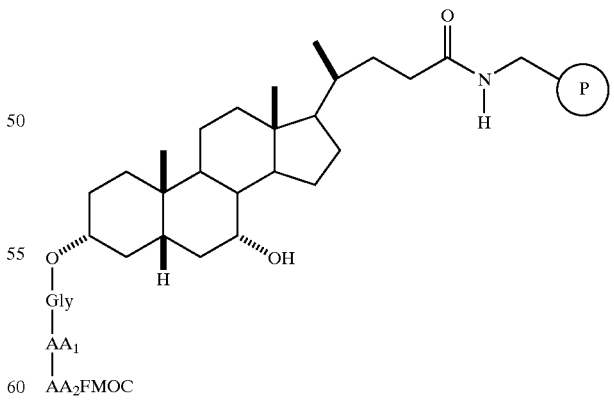

Gly
|
$AA_1$
|
$AA_2$FMOC

The second step $AA_2$ was initiated by the division of the above $C_3$—OGly$AA_1$FMOC, $C_7$—OH beads into ten equal portions. The labelling and coupling conditions were exactly same as the first $AA_1$. The tag molecules used to encode the second step synthesis are listed below:

| Tag molecules | Amount of Tags | Reaction vessel |
| --- | --- | --- |
| $T_5$, $C_6$, 2, 4, 5 $Cl_3$ | 1.0 mg | 1 |
| $T_6$, $C_6$, 2, 4, 6 $Cl_3$ | 1.0 mg | 2 |
| $T_7$, $C_7$, 2, 4, 5 $Cl_3$ | 1.0 mg | 3 |
| $T_8$, $C_7$, 2, 4, 6 $Cl_3$ | 1.0 mg | 4 |
| $T_5$, $T_6$ | $T_5$, 1.0 mg; $T_6$, 1.0 mg | 5 |
| $T_5$, $T_7$ | $T_5$, 1.0 mg; $T_7$, 1.0 mg | 6 |
| $T_5$, $T_8$ | $T_5$, 1.0 mg; $T_8$, 1.0 mg | 7 |
| $T_6$, $T_7$ | $T_6$, 1.0 mg; $T_7$, 1.0 mg | 8 |
| $T_6$, $T_8$ | $T_6$, 1.0 mg; $T_8$, 1.0 mg | 9 |
| $T_7$, $T_8$ | $T_7$, 1.0 mg; $T_8$, 1.0 mg | 10 |

After labelling, coupling and washing cycle, the $C_3$—OGlyAA$_1$AA$_2$FMOC, $C_7$—OH beads were obtained.

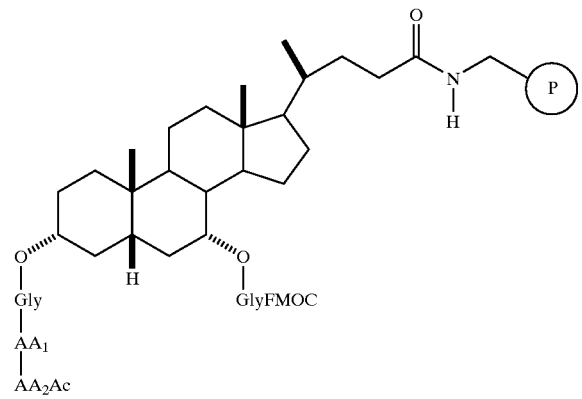

The above $C_3$—OGlyAA$_1$AA$_2$FMOC, $C_7$—OH beads were treated with 1:1 DMF/Piperidine (30 mL) to remove the FMOC-group. After under shaking at room temperature for 30 min, the beads were washed with 4×DMF and treated with HOAc (530 μL, 9 mmol), HOBT (1.35 g, 10 mmol) and DIC (1.4 mL, 9 mmol) in 35 mL DMF. The reaction mixtures were shaken for 2 h until the Kaiser test indicated the completion of the reaction. The beads were then thoroughly washed with 2×DMF (30 mL, 2 min each), 3×i-PrOH (30 mL, 2 min each) and 5×CH$_2$Cl$_2$ (30 mL, 2 min each), and then dried to give the $C_3$—OGlyAA$_1$AA$_2$Ac, $C_7$—OH beads.

To the above beads were added DIPEA (2.1 mL, 12 mmol) and DMAP (220 mg, 1.8 mmol) in 20 mL DMF followed by the addition of FMOC-GlyF (2.7 g, 9 mmol) in 15 mL DMF. After shaking at room temperature for 1 h, reagents were filtered and the beads were washed with DMF (30 mL) once. The resulting beads were retreated with DIPEA, DMAP and FMOC-GlyF in DMF twice under the same conditions and then washed with 3×DMF, 3×i-PrOH and 5×CH$_2$Cl$_2$, and then dried to give $C_3$—OGlyAA$_1$AA$_2$Ac, $C_7$—OGlyFMOC beads.

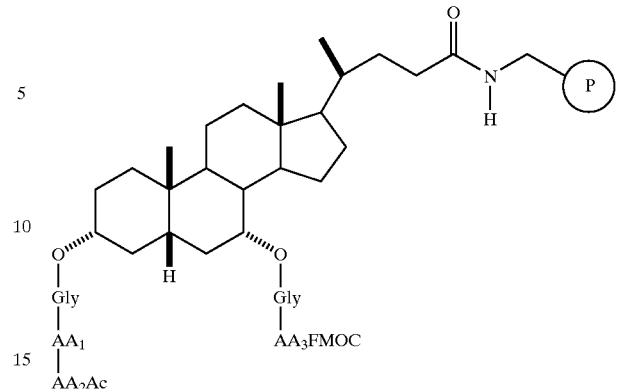

The third step AA$_3$ was also initiated by the division of the above $C_3$—OGlyAA$_1$AA$_2$Ac, $C_7$—OGlyFMOC beads into ten equal portions. The labelling and coupling conditions were exactly the same as the first steps. The tag molecule used to encode the third step synthesis are listed below:

| Tag Molecules | Amount of Tags | Reaction vessel |
| --- | --- | --- |
| $T_9$, $C_8$, 2, 4, 5 $Cl_3$ | 1.0 mg | 1 |
| $T_{10}$, $C_8$, 2, 4, 6 $Cl_3$ | 1.0 mg | 2 |
| $T_{11}$, $C_9$, 2, 4, 5 $Cl_3$ | 1.1 mg | 3 |
| $T_{12}$, $C_9$, 2, 4, 6 $Cl_3$ | 1.1 mg | 4 |
| $T_9$, $T_{10}$ | $T_9$, 1.0 mg; $T_{10}$, 1.0 mg | 5 |
| $T_9$, $T_{11}$ | $T_9$, 1.0 mg; $T_{11}$, 1.1 mg | 6 |
| $T_9$, $T_{12}$ | $T_9$, 1.0 mg; $T_{12}$, 1.1 mg | 7 |
| $T_{10}$, $T_{11}$ | $T_{10}$, 1.0 mg; $T_{11}$, 1.1 mg | 8 |
| $T_{10}$, $T_{12}$ | $T_{10}$, 1.0 mg; $T_{12}$, 1.1 mg | 9 |
| $T_{11}$, $T_{12}$ | $T_{11}$, 1.1 mg; $T_{12}$, 1.1 mg | 10 |

After labelling, coupling and washing cycle, the $C_3$—OGlyAA$_1$AA$_2$Ac, $C_7$—OGlyAA$_3$FMOC beads were obtained.

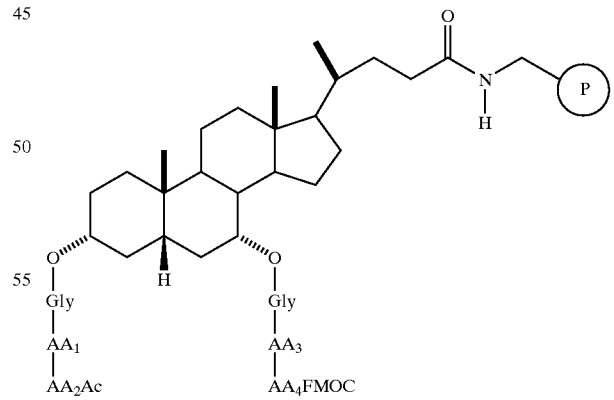

The labelling and coupling conditions of the fourth step AA$_4$ were exactly the same as that of the previous steps. At the end of the synthesis, the $C_3$—OGlyAA$_1$AA$_2$Ac, $C_7$OGlyAA$_3$AA$_4$FMOC were obtained. The tag molecules used for this step are listed below:

| Tag molecules | Amount of Tags | Reaction vessels |
| --- | --- | --- |
| $T_{13}$, $C_{10}$, 2, 4, 5 $Cl_3$ | 1.1 mg | 1 |
| $T_{14}$, $C_{10}$, 2, 4, 6 $Cl_3$ | 1.1 mg | 2 |
| $T_{15}$, $C_{11}$, 2, 4, 5 $Cl_3$ | 1.1 mg | 3 |
| $T_{16}$, $C_{11}$, 2, 4, 6 $Cl_3$ | 1.1 mg | 4 |
| $T_{13}$, $T_{14}$ | $T_{13}$, 1.1 mg; $T_{14}$, 1.1 mg | 5 |
| $T_{13}$, $T_{15}$ | $T_{13}$, 1.1 mg; $T_{15}$, 1.1 mg | 6 |
| $T_{13}$, $T_{16}$ | $T_{13}$, 1.1 mg; $T_{16}$, 1.1 mg | 7 |
| $T_{14}$, $T_{15}$ | $T_{14}$, 1.1 mg; $T_{15}$, 1.1 mg | 8 |
| $T_{14}$, $T_{16}$ | $T_{14}$, 1.1 mg; $T_{16}$, 1.1 mg | 9 |
| $T_{15}$, $T_{16}$ | $T_{15}$, 1.1 mg; $T_{16}$, 1.1 mg | 10 |

To the above $C_3$—OGlyAA$_1$AA$_2$Ac, $C_7$—OGlyAA$_3$AA$_4$FMOC beads was added 1:1 DMF/Piperidine (30 mL) to remove the FMOC-group. The reaction mixtures were shaken at room temperature for 30 min. and then the beads were washed with 4×DMF and treated with HOAc (530 μL, 9 mmol), HOBT (1.35 g, 10 mmol) and DIC (1,4 mL, 9 mmol) in 35 mL DMF. The reaction mixtures were shaken for 2 h until the Kaiser test indicated the completion of the reaction. The beads were then thoroughly washed with 2×DMF (30 mL, 2 min each), 3×i-PrOH (30 mL, 2 min each) and 5×CH$_2$Cl$_2$ (30 mL, 2 min each), and then dried to give the protected Gly-library.

The Deprotected Gly-Library

To the resulting $C_3$—OGly AA$_1$AA$_2$Ac, C7—OGlyAA$_3$AA$_4$Ac beads (1.0 g) was added 25% TFA/CH$_2$Cl$_2$ solution (20 mL). The reaction vessel was shaken at room temperature for 1 h, and the beads were washed with 4×CH$_2$Cl$_2$, 3×i-PrOH and 5×CH$_2$Cl$_2$, and dried to afford the deprotected Gly-library.

The Synthesis of Pro-Library

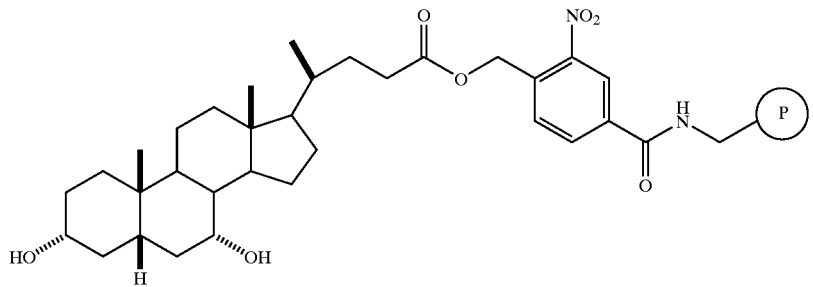

5

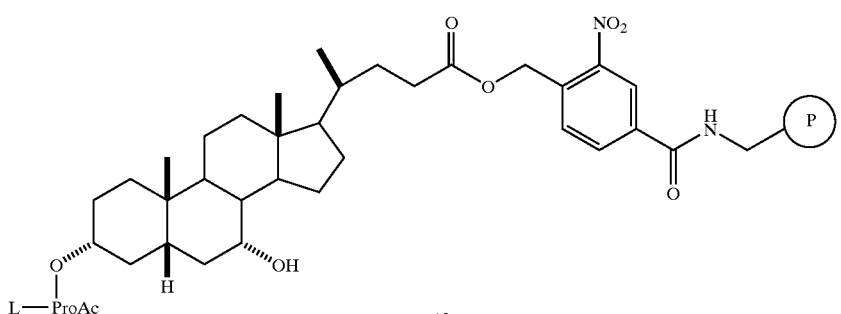

13

To the detectable beads 5 (220 mg, 0.13 mmol) were added DIPEA (350 μL, 2.0 mmol) and tetrazole (140 mg, 2.0 mmol) in 3 μL CH$_2$Cl$_2$ followed by the addition of L-ProCl (360 mg, 1.0 mmol) in 1 mL CH$_2$Cl$_2$. After shaking at room temperature for 12 h. reagents were filtered and the beads were washed with 4×CH$_2$Cl$_2$ (5 mL, 2 min each), and then dried.

To the above beads was added 1:1 DMF/piperidine (5 mL). The reaction vessel was shaken at room temperature for 30 min. and then the beads were washed with 4×DMF and treated with HOAc (39 μL, 0.65 mmol), HOBT (88 mg, 0.65 mmol) and DIC (100 μl, 0.65 mmol) in 4 mL DMF. The reaction mixtures were shaken for 2 h until the Kaiser test indicated the completion of the reaction. The beads were then thoroughly washed with 2×DMF (5 mL, 2 min each), 3×i-PrOH (5 mL, 2 min each) and 5×CH$_2$Cl$_2$ (5 mL, 2 min each), and then dried on pump to afford beads 13.

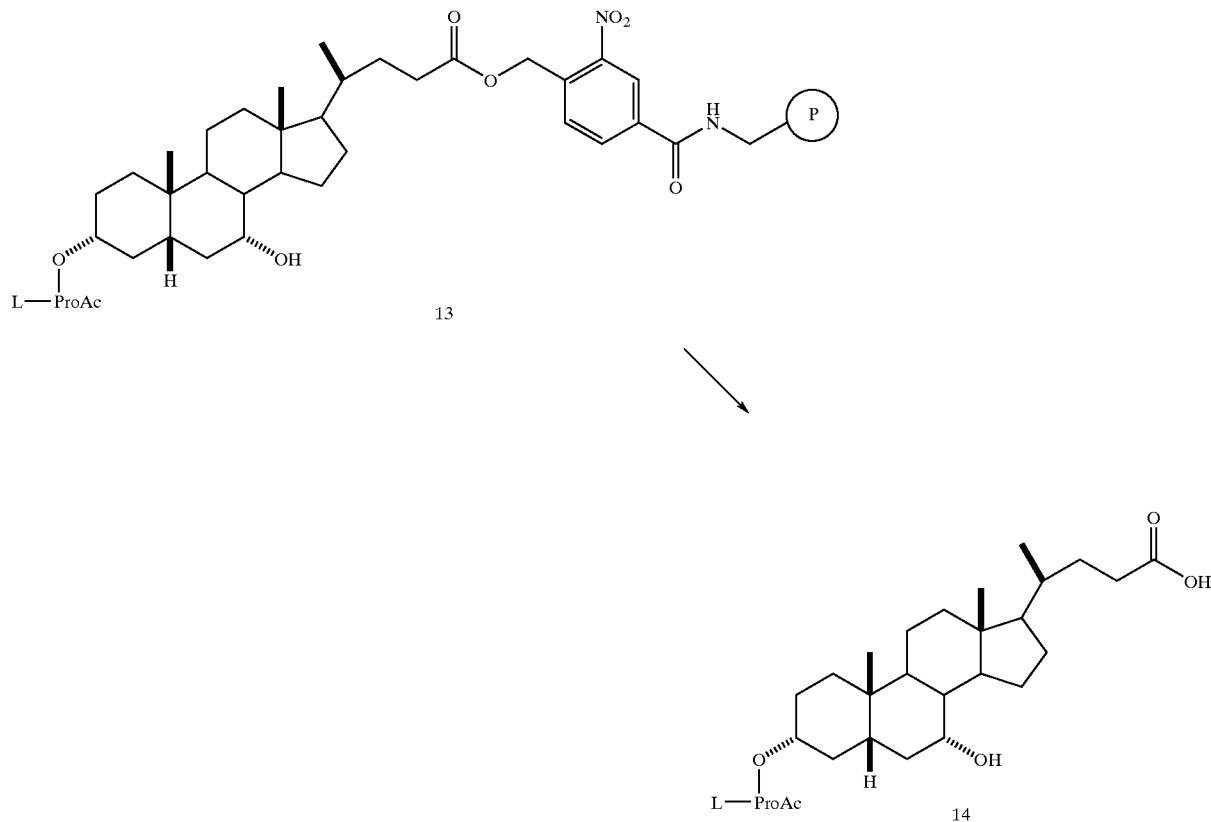

The beads 13 (25 mg) and 500 μL CH$_3$OH in a capped 1 mL test tube were under UV light for 12 h. The beads were filtered and the filtrate was concentrated to give 14 as a white solid. The NMR spectrum of 14 indicates that the selectivity for esterification of C$_3$—OH and C$_3$—OH is 25:1.

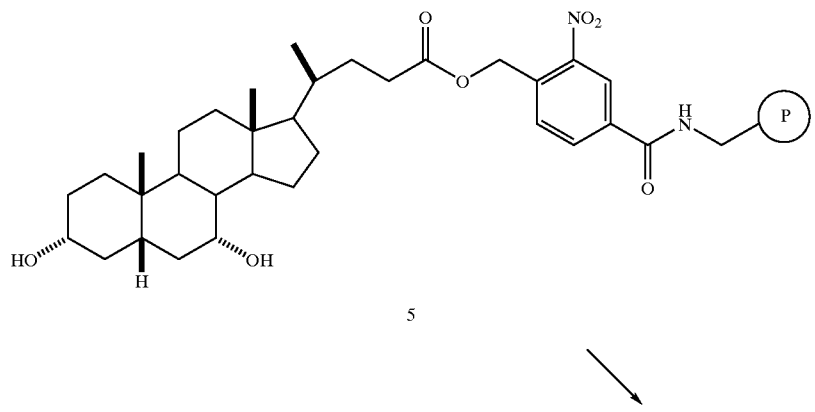

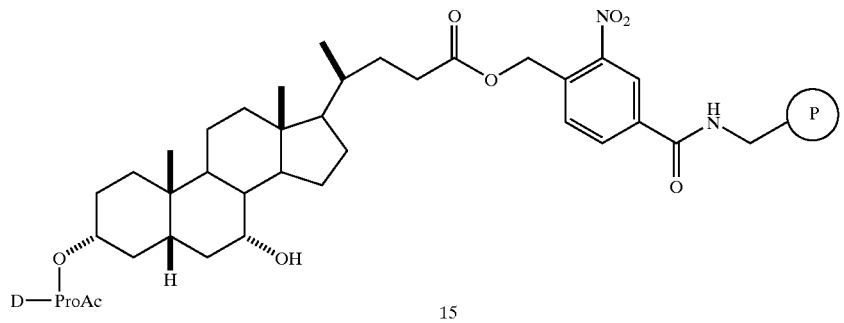

15

To the detectable beads 5 (220 mg, 0.13 mmol) were added DIPEA (350 μL, 2.0 mmol) and tetrazole (140 mg, 2.0 mmol) in 3 mL Ch₂Cl₂ followed by the addition of D-ProCl (360 mg, 1.0 mmol) in 1 mL CH₂Cl₂. After shaking at room temperature for 6 h, reagents were filtered and the beads were washed with 4×CH₂Cl₂ (5 mL, 2 min each), 2×CH₃OH (5 mL, 2 min each) and 4×CH₂Cl₂ (5 mL, 2 min each), and then dried.

To the above beads was added 1:1 DMF/piperidine (5 mL). The reaction vessel was shaken at room temperature for 30 min. and then the beads were washed with 4×DMF and treated with HOAc (39 μL, 0.65 mmol), HOBT (88 mg, 0.65 mmol) and DIC (100 μl, 0.65 mmol) in 4 mL DMF. The reaction mixtures were shaken for 2 h until the Kaiser test indicated the completion of the reaction. The beads were then thoroughly washed with 2×DMF (5 mL, 2 min each), 3×i-PrOH (5 mL, 2 min each) and 5×CH₂Cl₂ (5 mL, 2 min each), and then dried on pump to afford beads 15.

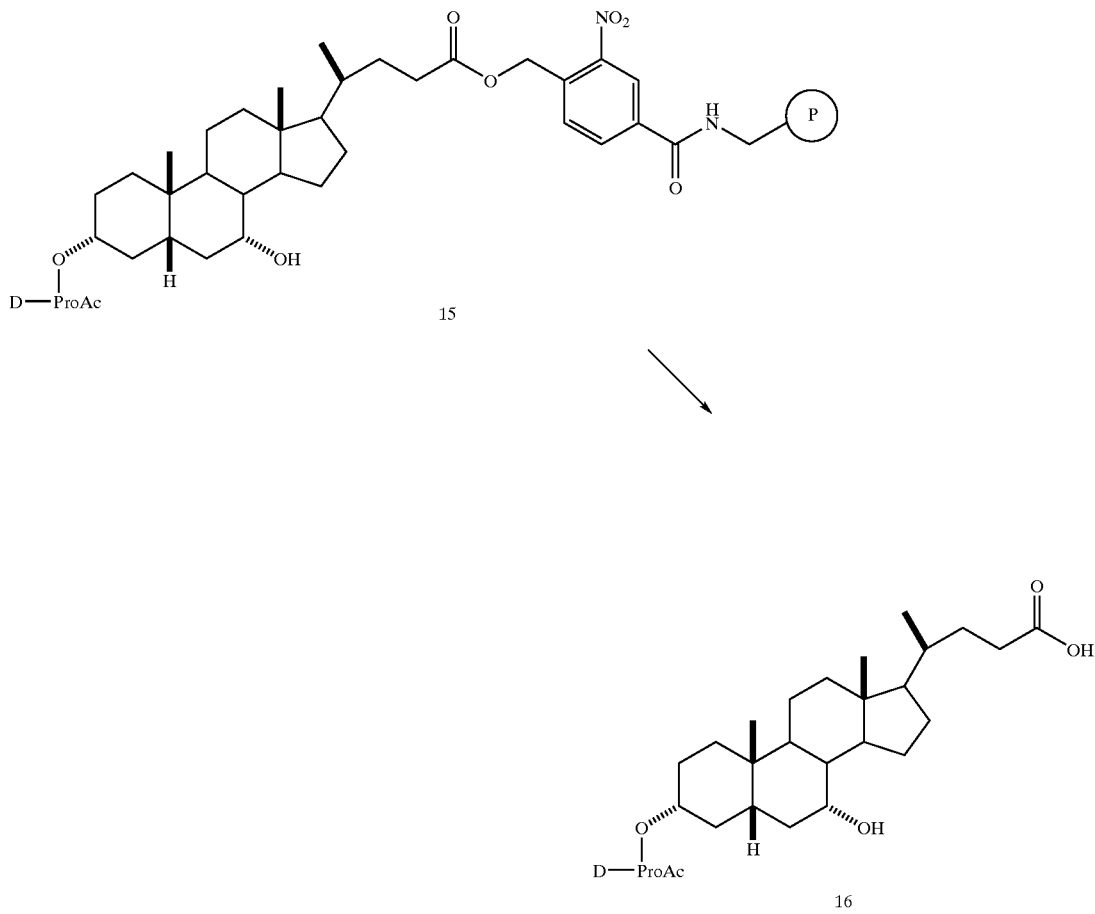

The beads 15 (25 mg) and 500 μL CH$_3$OH in a capped 1 mL test tube were under UV light for 12 h. The beads were filtered, and the filtrate was concentrated to give 16 as a white solid. The NMR spectrum of 16 indicates that the selectivity for esterification of C$_3$—OH and C$_7$—OH is 20:1.

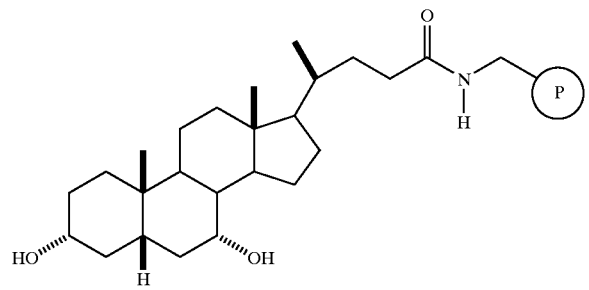

To a 50 mL reaction vessel containing 2 g aminomethyl resin (1.8 mmol, 0.9 mmol/g) were added HOBT (675 mg, 5.0 mmol), DIC (660 μL, 4.5 mmol) and chenodeoxycholic acid (1.8 g, 4.5 mmol) in 30 mL DMF. The reaction mixtures were shaken at room temperature for 6.8 h. When the Kaiser test indicated the completion of the coupling reaction, the beads in the reaction vessel were washed with 2×DMF (30 mL, 2 min each), 3×i-PrOH (30 mL, 2 min each), 5×CH$_2$Cl$_2$ (30 mL, 2 min each) and dried to give the chenodeoxycholic acid beads (2.7 g).

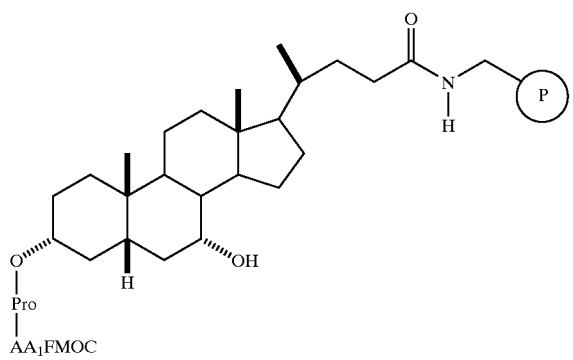

Two equal portions (1.3 g, 0.9 mmol) of the above resin were placed into two reaction vessels which were labeled as A and B.

Beads in the reaction vessel A were treated with DIPEA (2.4 mL, 14 mmol) and tetrazole (980 mg, 14 mmol) in 20 mL CH$_2$Cl$_2$ followed by the addition of L-ProCl (2.4 g, 7 mmol) in 10 mL CH$_2$Cl$_2$. After under shaking at room temperature for 12 h, the beads were thoroughly washed with 3×CH$_2$Cl$_2$, 2×i-PrOH and 4×CH$_2$Cl$_2$ and dried. The resulting beads were divided into ten equal portions (150 mg, ~0.09 mmol) and placed into tan reaction vessels. The reaction vessels were labeled as 1,2, ... , 10. Each portion of the beads was treated with 1:1 DMF/piperidine (10 mL) at room temperature for 30 min to remove FMOC-protecting group. After washing the beads with 4×DMF, the tag molecules (0.9×10$^{-3}$ mmol), HOBT (9.5 mg, 0.07 mmol, 75 eq.) and DIC (11 μL, 0.07 mmol, 75 eq.) in 4 mL DMF were added to each reaction vessel in the following manner:

| Tag molecules | Amount of Tags | Reaction vessel |
|---|---|---|
| T$_1$, T$_3$ | T$_1$, 0.7 mg; T$_3$, 0.6 mg | 1 |
| T$_1$, T$_4$ | T$_1$, 0.7 mg; T$_4$, 0.6 mg | 2 |
| T$_1$, T$_5$ | T$_1$, 0.7 mg; T$_5$, 0.6 mg | 3 |
| T$_1$, T$_6$ | T$_1$, 0.7 mg; T$_6$, 0.6 mg | 4 |
| T$_1$, T$_3$, T$_4$ | T$_1$, 0.7 mg; T$_3$, 0.6 mg; T$_4$, 0.6 mg | 5 |
| T$_1$, T$_3$, T$_5$ | T$_1$, 0.7 mg; T$_3$, 0.6 mg; T$_5$, 0.6 mg | 6 |
| T$_1$, T$_3$, T$_6$ | T$_1$, 0.7 mg; T$_4$, 0.6 mg; T$_6$, 0.6 mg | 7 |
| T$_1$, T$_3$, T$_5$ | T$_1$, 0.7 mg; T$_4$, 0.6 mg; T$_5$, 0.6 mg | 8 |
| T$_1$, T$_3$, T$_6$ | T$_1$, 0.7 mg; T$_4$, 0.6 mg; T$_6$, 0.6 mg | 9 |
| T$_1$, T$_5$, T$_6$ | T$_1$, 0.7 mg; T$_5$, 0.6 mg; T$_6$, 0.6 mg | 10 |

After shaking for 12 h in the dark at room temperature, the beads in each reaction vessel were washed with 4×CH$_2$Cl$_2$ (10 mL each) FMOC-AA (0.25 mmol), OBT 35 mg, 0.25 mmol, and DIC (40 μL, 0.25 mmol) in 4 mL DMF were added to each reaction vessels as follows:

| Amino Acids | Amount of Amino Acids | Reaction vessel |
|---|---|---|
| Ala | 78 mg | 1 |
| Val | 85 mg | 2 |
| Leu | 89 mg | 3 |
| Phe | 97 mg | 4 |
| Pro | 85 mg | 5 |
| Ser | 96 mg | 6 |
| Thr | 100 mg | 7 |
| Lys | 120 mg | 8 |
| Glu | 105 mg | 9 |
| Asp | 103 mg | 10 |

When the resin in each reaction vessel gave a negative Kaiser test, normally 3 h at room temperature. Then the beads in ten reaction vessels were combined in a 50 mL reaction vessel and washed with 2×DMF (30 mL, 2 in each), 3×i-PrOH (30 mL, 2 min each) and 5×CH$_2$Cl$_2$ (30 mL, 2 min each), and dried to afford C$_3$—O-L-ProAA$_1$FMOC, C$_7$—OH beads.

Beads in the reaction vessel B were treated with DIPEA (2.4 mL, 14 mmol) and tetrazole (980 mg, 14 mmol) in 20 mL CH$_2$Cl$_2$. After shaking at room temperature for 6 h, the beads were thoroughly washed with 3×CH$_2$Cl$_2$, 2×i-PrOH an d4×CH$_2$Cl$_2$ and dried. The resulting beads were divided into ten equal portions (150 mg, ~0.09 mmol) and placed into ten reaction vessels. The reaction vessels wee labeled as 1,2, ... , 10. Each portion of the beads was treated with 1:1 DMF/piperidine (10 mL) at room temperature for 30 min to remove FMOC-protecting group. After washing the beads with 4×DMF, the tag molecules 10.9×10$^{-3}$ mmol), HOBT (9.5 mg, 0.07 mmol, 75 eq.) and DIC (11 μL, 0.07 mmol, 75 eq.) in 4 mL DMF were added to each reaction vessel in the following manner:

| Tag molecules | Amount of Tags | Reaction vessel |
|---|---|---|
| T$_2$, T$_3$ | T$_2$, 0.7 mg; T$_3$, 0.6 mg | 1 |
| T$_2$, T$_4$ | T$_2$, 0.7 mg; T$_4$, 0.6 mg | 2 |
| T$_2$, T$_5$ | T$_2$, 0.7 mg; T$_5$, 0.6 mg | 3 |
| T$_2$, T$_6$ | T$_2$, 0.7 mg; T$_6$, 0.6 mg | 4 |
| T$_2$, T$_3$, T$_4$ | T$_2$, 0.7 mg; T$_3$, 0.6 mg; T$_4$, 0.6 mg | 5 |
| T$_2$, T$_3$, T$_5$ | T$_2$, 0.7 mg; T$_3$, 0.6 mg; T$_5$, 0.6 mg | 6 |
| T$_2$, T$_3$, T$_6$ | T$_2$, 0.7 mg; T$_3$, 0.6 mg; T$_6$, 0.6 mg | 7 |

-continued

| Tag molecules | Amount of Tags | Reaction vessel |
|---|---|---|
| $T_2, T_4, T_5$ | $T_2$, 0.7 mg; $T_4$, 0.6 mg; $T_5$, 0.6 mg | 8 |
| $T_2, T_4, T_6$ | $T_2$, 0.7 mg; $T_4$, 0.6 mg; $T_6$, 0.6 mg | 9 |
| $T_2, T_5, T_6$ | $T_2$, 0.7 mg; $T_5$, 0.6 mg; $T_6$, 0.6 mg | 10 |

After shaking 12 h in the dark at room temperature, the beads in each reaction vessel were washed with $4 \times CH_2Cl_2$ (10 mL each). FMOC-AA (0.25 mmol), HOBT (35 mg, 0.25 mmol) and DIC (40 μL, 0.25 mmol) in 4 mL DMF were added to each reaction vessels as:

| Amino Acids | Amount of Amino Acids | Reaction vessel |
|---|---|---|
| Alan | 78 mg | 1 |
| Val | 85 mg | 2 |
| Leu | 89 mg | 3 |
| Phe | 97 mg | 4 |
| Pro | 85 mg | 5 |
| Ser | 96 mg | 6 |
| Thr | 100 mg | 7 |
| Lys | 120 mg | 8 |
| Glu | 105 mg | 9 |
| Asp | 103 mg | 10 |

When the resin in each vessel gave a negative Kaiser test, normally 3 hours at room temperature. Then the beads in ten reaction vessels were combined in a 50 mL reaction vessel and washed with $2 \times DMF$ (30 mL, 2 min each), $3 \times i\text{-PrOH}$ (30 mL, 2 min each) and $5 \times CH_2Cl_2$ (30 mL, 2 min each), and dried to afford $C_3$—O-D-ProAA$_1$FMOC, $C_7$—OH beads.

The above D and L Pro beads were then combined in a single reaction vessel. The combined beads suspended in 30 μL $CH_2Cl_2$ were shaken at room temperature for 30 min. The solvent was filtered and the beads were dried to give $C_3$—O-DL-ProAA$_1$FMOC, $C_7$—OH beads.

The tag molecules used for this step synthesis are:

| | | |
|---|---|---|
| $T_1$, $C_{12}$, $Cl_5$ | $T_2$, $C_{11}$, $Cl_5$ | $T_3$, $C_{11}$, 2, 4, 5, $Cl_3$ |
| $T_4$, $C_{11}$, 2, 4, 6, $Cl_3$ | $T_5$, $C_{12}$, 2, 4, 5, $Cl_3$ | $T_6$, $C_{12}$, 2, 4, 6, $Cl_3$ |

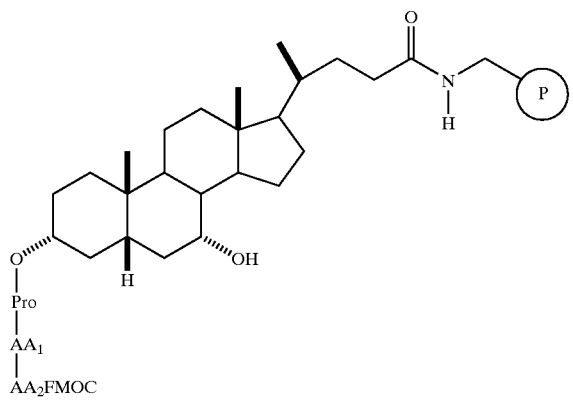

The second step $AA_2$ was initiated by the division of the above $C_3$—O-DL-PrOAA$_1$FMOC, $C_7$—OH beads into ten equal portions. Each portion of the beads was treated with 1:1 DMF/piperidine (10 mL) at room temperature for 30 min to remove FMOC protecting group. After washing the beads with $4 \times DMF$, the tag molecules ($1.8 \times 10^{-3}$ mmol), HOBT (13 mg, 0.09 mmol, 50 El.) and DIC (14 μL, 0.09 mmol, 50 eq.) in 4 mL DMF were added to each reaction vessel in the following manner:

| Tag Molecules | Amount of Tags | Reaction vessel |
|---|---|---|
| $T_7$, $C_9$, 2, 4, 5 $Cl_3$ | 1.0 mg | 1 |
| $T_8$, $C_9$, 2, 4, 6 $Cl_3$ | 1.0 mg | 2 |
| $T_9$, $C_{10}$, 2, 4, 5 $Cl_3$ | 1.0 mg | 3 |
| $T_{10}$, $C_{10}$, 2, 4, 6 $Cl_3$ | 1.0 mg | 4 |
| $T_7$, $T_8$ | $T_7$, 0.9 mg; $T_8$, 0.9 mg | 5 |
| $T_7$, $T_9$ | $T_7$, 0.9 mg; $T_9$, 0.9 mg | 6 |
| $T_7$, $T_{10}$ | $T_7$, 0.9 mg; $T_{10}$, 0.9 mg | 7 |
| $T_8$, $T_9$ | $T_8$, 0.9 mg; $T_9$, 0.9 mg | 8 |
| $T_8$, $T_{10}$ | $T_8$, 0.9 mg; $T_{10}$, 0.9 mg | 9 |
| $T_9$, $T_{10}$ | $T_9$, 0.9 mg; $T_{10}$, 0.9 mg | 10 |

After shaking 12 h in the dark at room temperature, the beads in each reaction vessel were washed with $4 \times CH_2Cl_2$ (10 mL each). FMOC-AA (0.5 mmol), HOBT (70 mg, 0.5 mmol) and DIC (80 μL, 0.5 mmol) in 4 mL DMF were added to each reaction vessels as:

| Amino Acids | Amount of Amino Acids | Reaction vessel |
|---|---|---|
| Ala | 156 mg | 1 |
| Val | 170 mg | 2 |
| Leu | 177 mg | 3 |
| Phe | 194 mg | 4 |
| Pro | 170 mg | 5 |
| Ser | 192 mg | 6 |
| Thr | 199 mg | 7 |
| Lys | 235 mg | 8 |
| Glu | 213 mg | 9 |
| Asp | 206 mg | 10 |

When the resin in each reaction vessel gave a negative Kaiser test, normally 3 h at room temperature. Then the beads in ten reaction vessels were combined in a 50 mL reaction vessel and washed with $2 \times DMF$ (30 mL, 2 min each), $3 \times i\text{-PrOH}$ (30 mL, 2 min each) and $5 \times CH_2Cl_2$ (30 mL, 2 min each), and dried to afford $C_3$—OProAA$_1$AA$_2$FMOC, $C_7$—OH beads.

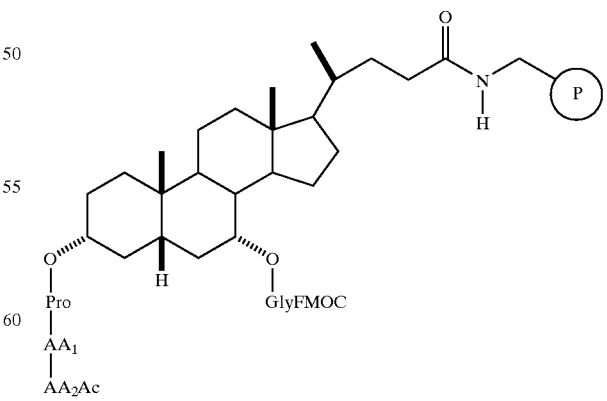

The above $C_3$—OProAA$_1$AA$_2$FMOC, $C_7$—OH beads were treated with 1:1 DMF/Piperidine (30 mL) to remove the FMOC-group. After under shaking at room temperature for 30 min. the beads were washed with 4×DMF and treated with HOAc (530 μL, 9 mmol), HOBT (1.35 g, 10 mmol) and DIC 1.4 mL, 9 mmol) in 35 mL DMF. The reaction mixtures were shaken for 2 h until the Kaiser test indicated the completion of the reaction. The beads were then thoroughly washed with 2×DMF (30 mL, 2 min each), 3×i-PrOH (30 mL, 2 min each) and 5×CH$_2$Cl$_2$(30 mL, 2 min each), and then dried to give the C$_3$—OProAA$_1$AA$_2$Ac, C$_7$—OH beads.

To the above beads were added DIPEA (2.1 mL, 12 mmol) and DMAP (220 mg, 1.8 mmol) in 20 mL DMF followed by the addition of FMOC-GlyF (2.7 g, 9 mmol) in 15 mL DMF. After shaking at room temperature for 1 h, reagents were filtered and the beads were washed with DMF (30 mL) once. The resulting beads were retreated with DIPEA, DMAP and FMOC-GlyF in DMF twice under the same conditions and then washed with 3×DMF, 3×i-PrOH and 5×CH$_2$Cl$_2$, and then dried to give C$_3$—OProAA$_1$AA$_2$Ac, C$_7$—OGlyFMOC beads.

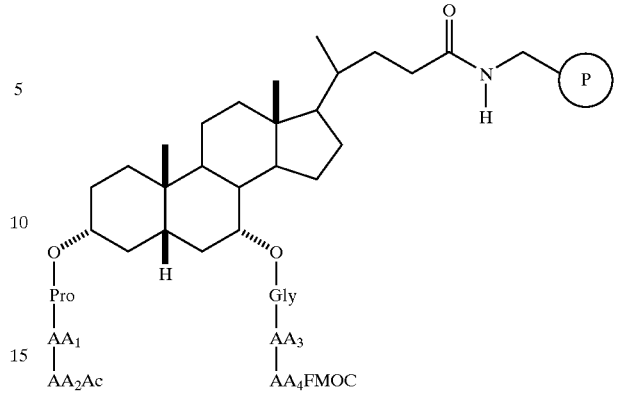

The labelling and coupling conditions of the fourth step AA$_4$ were exactly same as that of the second step. At the end of the synthesis, the C$_3$—OProAA$_1$AA$_2$Ac, C$_7$—OGlyAA$_3$FMOC beads were obtained.

The tag molecules used for this step are listed below:

| Tag molecules | Amount of Tags | Reaction vessel |
| --- | --- | --- |
| T$_{15}$, C$_4$, 2, 4, 5 Cl$_3$ | 1.0 mg | 1 |
| T$_{16}$, C$_5$, 2, 4, 6 Cl$_3$ | 1.0 mg | 2 |
| T$_{17}$, C$_6$, 2, 4, 5 Cl$_3$ | 1.0 mg | 3 |
| T$_{18}$, C$_6$, 2, 4, 6 Cl$_3$ | 1.0 mg | 4 |
| T$_{15}$, T$_{16}$ | T$_{15}$, 0.9 mg; T$_{16}$, 0.9 mg | 5 |
| T$_{15}$, T$_{17}$ | T$_{15}$, 0.9 mg; T$_{17}$, 0.9 mg | 6 |
| T$_{15}$, T$_{18}$ | T$_{15}$, 0.9 mg; T$_{18}$, 0.9 mg | 7 |
| T$_{16}$, T$_{17}$ | T$_{16}$, 0.9 mg; T$_{17}$, 0.9 mg | 8 |
| T$_{16}$, T$_{18}$ | T$_{16}$, 0.9 mg; T$_{18}$, 0.9 mg | 9 |
| T$_{17}$, T$_{18}$ | T$_{16}$, 0.9 mg; T$_{18}$, 0.9 mg | 10 |

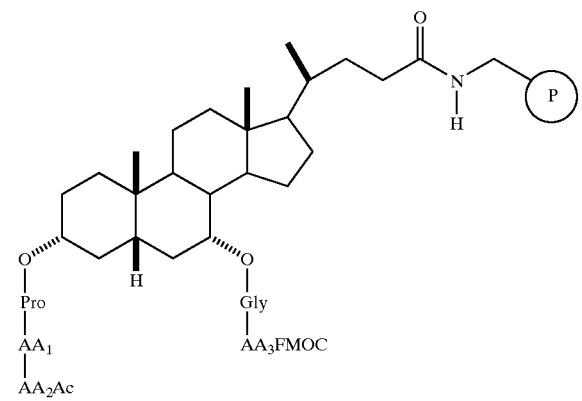

The third step AA$_3$ was also initiated by the division of the above C$_3$—OProAA$_1$AA$_2$Ac, C$_7$—OGlyFMOC beads into ten equal portions. The labelling and coupling conditions were exactly the same as the second steps. The tag molecules used to encode the third step synthesis are listed below:

| Tag molecules | Amount of Tags | Reaction vessel |
| --- | --- | --- |
| T$_{11}$, C$_7$, 2, 4, 5 Cl$_3$ | 1.0 mg | 1 |
| T$_{12}$, C$_7$, 2, 4, 6 Cl$_3$ | 1.0 mg | 2 |
| T$_{13}$, C$_8$, 2, 4, 5 Cl$_3$ | 1.0 mg | 3 |
| T$_{14}$, C$_8$, 2, 4, 6 Cl$_3$ | 1.0 mg | 4 |
| T$_{11}$, T$_{12}$ | T$_{11}$, 1.0 mg; T$_{12}$, 1.0 mg | 5 |
| T$_{11}$, T$_{13}$ | T$_{11}$, 1.0 mg; T$_{13}$, 1.0 mg | 6 |
| T$_{11}$, T$_{14}$ | T$_{11}$, 1.0 mg; T$_{14}$, 1.0 mg | 7 |
| T$_{12}$, T$_{13}$ | T$_{12}$, 1.0 mg; T$_{13}$, 1.0 mg | 8 |
| T$_{12}$, T$_{14}$ | T$_{12}$, 1.0 mg; T$_{14}$, 1.0 mg | 9 |
| T$_{13}$, T$_{14}$ | T$_{13}$, 1.0 mg; T$_{14}$, 1.0 mg | 10 |

After labelling, coupling and washing cycles, the C$_3$—OProAA$_1$AA$_2$Ac, C$_7$—OGlyAA$_3$FMOC beads were obtained.

To the above C$_3$—OProAA$_1$AA$_2$Ac, C$_7$—OGlyAA$_3$FMOC beads was added 1:1 N,N-Dimethylformamide/Piperdine (30 mL) to remove the 9-Fluorenylmethloxycarbonyl-group. The reaction mixtures were shaken at room temperature for 30 min. and then the beads were washed with 4×N,N-Dimethylformamide and treated with Acetic Acid (530 μL, 9 mmol), 1-hydroxybenzotriazole (1.35 g, 10 mmol) and DIC (1.4 mL, 9 mmol) in 35 mL N,N-Dimethylformamide. The reaction mixtures were shaken for 2 hours until the Kaiser test indicated the completion of the reaction. The beads were then thoroughly washed with 2×DMF (30 mL, 2 min each), 3×i-PrOH (30 mL, 2 min each) and 5×CH$_2$Cl$_2$, 3×i-PrOH and 5×CH$_2$Cl$_2$, and dried to afford the deprotected Pro-Library.

Figure 4:
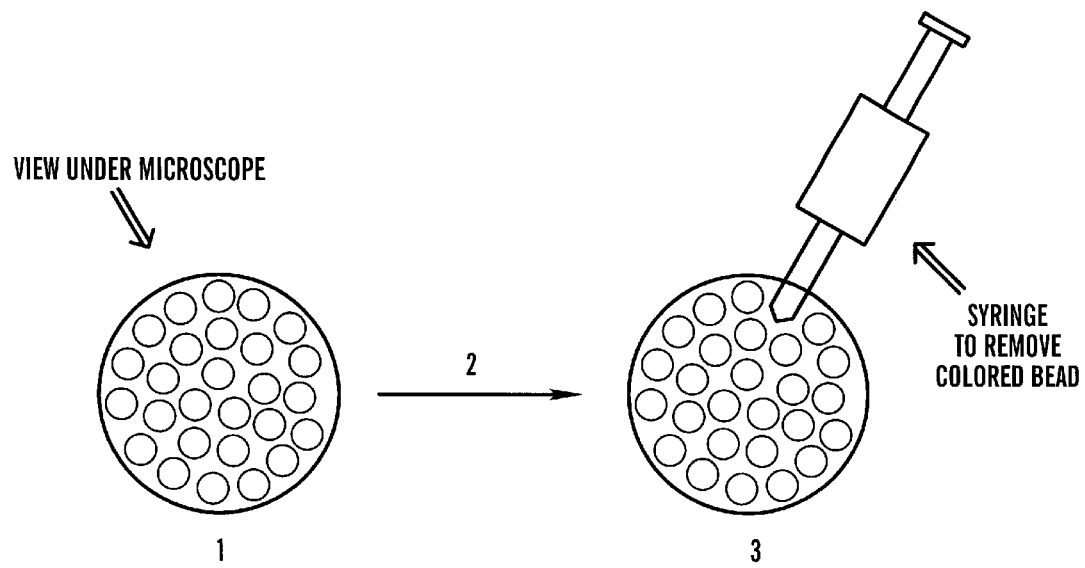
FIG. 4.

A color assay method was developed for screening receptor library beads. The color dye used is Disperse Red 1 (available from Aldrich Inc.), a neutral diazo dye whose λmax is at 502 nm. Red color in various organic solvents is visible at concentration as low as 100 μM. The method is shown in FIG. 4.

Figure 5:
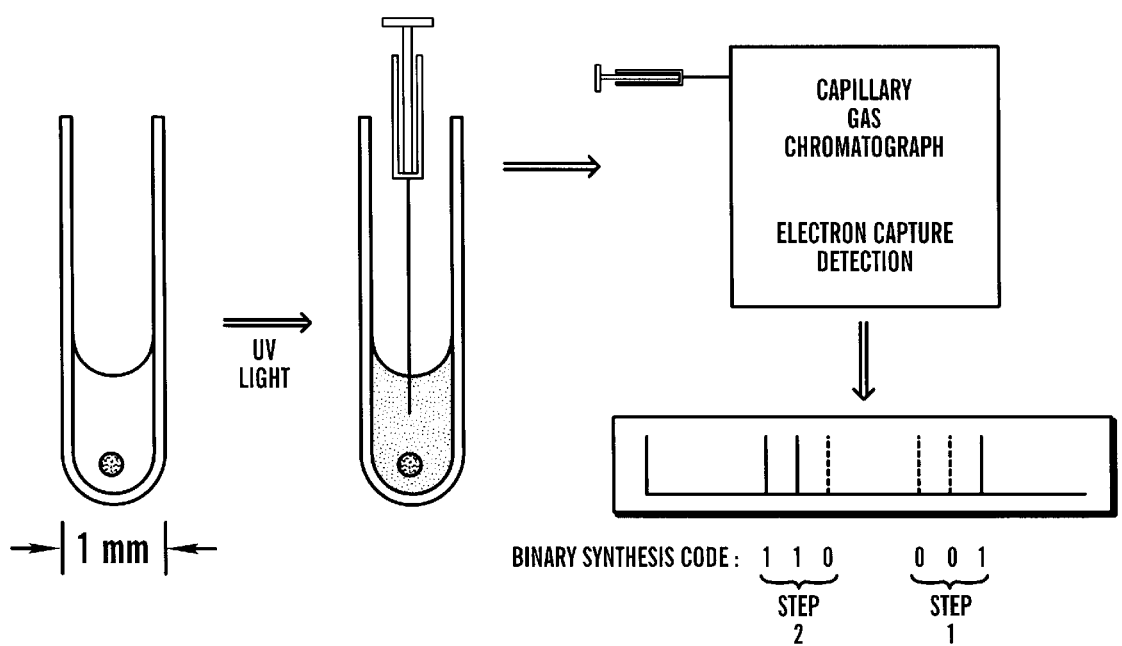
FIG. 5.
Figure 6:
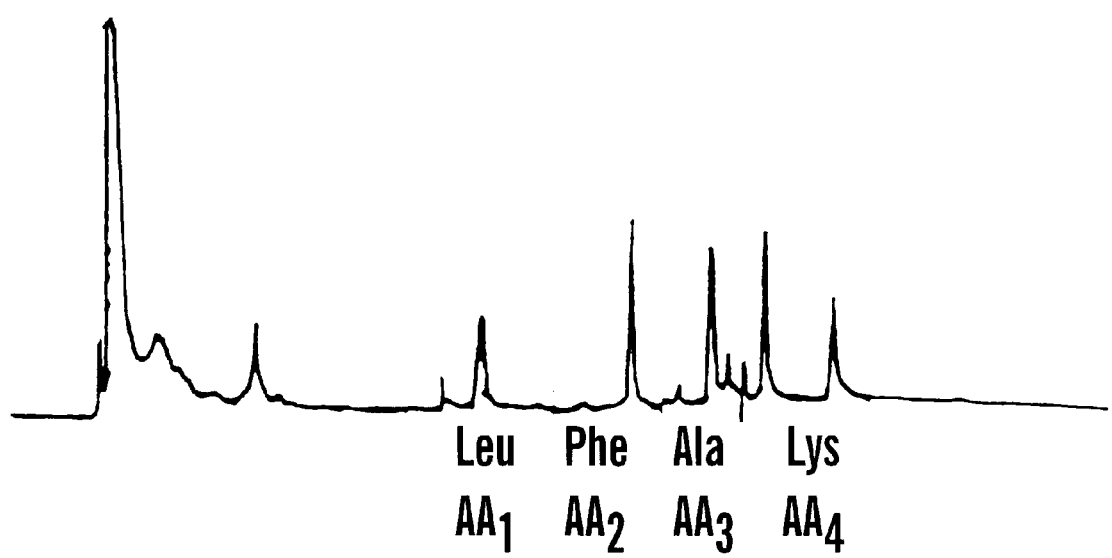
FIG. 6.

After receptor beads are treated with a substrate which has a color dye attached on it, the bead binding the substrate is stained and can be easily identified in a background of many colorless beads. The stained bead is the removed from the library by a microsyringe, and subjected to decode to identify its structure. The decoding process involves three operations: a) photolysis of the beads, b) silylation of liberated alcohols, c) injection into GC-EC machine. Once identified, the receptor is then resynthesized on large quantities of beads for confirmatory binding studies. FIG. 5 shows the process used to read the molecular bar code of typical a bead and in FIG. 6 the a typical gas chromatography for a bead is shown. From this spectrum, the structure of the receptor is identified as $C_3$—OGLY-leu-phe-Ac, $C_7$—OGLY-ala-Lys-Ac.

The Gly-receptor library was first treated with dye-derivatized serine 17 shown below, it was found that more than 50% beads stained as orange color. It is believed this nonspecific binding could be reduced either by screening the library with more functionalized and more conformationally defined substrates such as bio-interesting peptides or by synthesizing another library whose binding conformation is more rigid.

rigidity the $C_3$ chain. Therefore, the binding conformation for second receptor might be more defined than that of the first one.

The Gly-library was found to bind Leucine Enkephalin 18 and Met Enkephalin 19 very selectively.

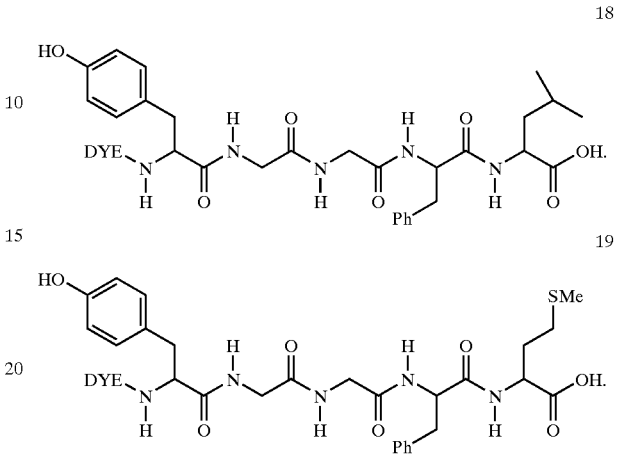

Enkephalin is an important neuropeptide (Leu Enkephalin and Met Enkephalin are both commercially available from Bachem, Inc; Fodor, S. P. A.; Read, J. L.; Pirrung, M. C.; Stryer, L.; Lu, A. T. and Solas, D. *Science* 1991, 251, 767; Hughes, J.; Smith, T. W.; Kosterlitz, H. W.; Fothergill, L. A.;

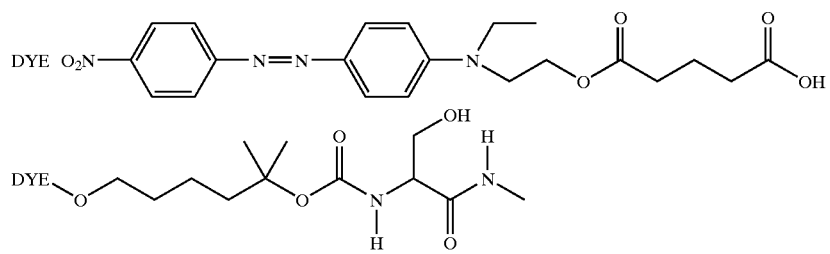

The second receptor library (Pro-library) is shown in shown below.

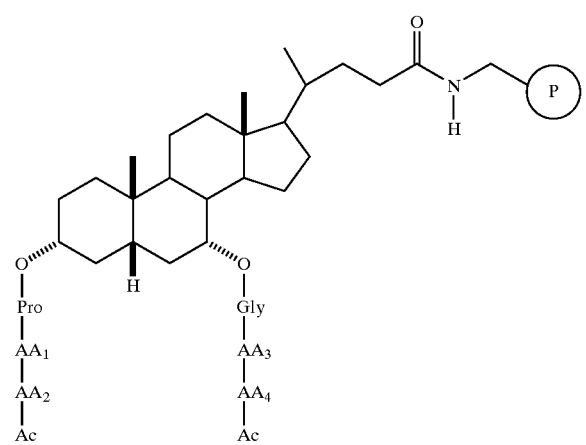

"Pro" Library Containing 20,000 Elements

It was expected that D or L proline at the first position of $C_3$-chain instead of glycine in the previous library would Morgan, B. A. and Morrio, H. R. *Nature*, 1975, 258, 577). It is a natural ligand for an opiate receptor composed of two pentapeptides Tyr-Gly-Gly-Phe-LeuOH and Tyr-Gly-Gly-Phe-MetOH. In contrast to the above case of "serine" binding, the percentage of stained beads is 0.65% for Leucine Enkephalin and 0.53% for Met Enkephalin. 17 active beads against Leu Enkephalin and 28 active beads against Met Enkephalin were retrieved from the Gly library and decoded. The sequences of two peptide chains are summarized in Table 1 and 2.

TABLE 1

Protected Gly-library Binding with Leucine Enkephalin

| C3 Chain | C7 Chain | |
|---|---|---|
| GLY-ASP-PRO | GLY-PRO-GLU | (FOUND 5X) |
| GLY-ASP-PRO | GLY-PRO-VAL | (FOUND 3X) |
| GLY-PHE-PRO | GLY-PRO-LEU | (FOUND 3X) |
| GLY-LEU-PRO | GLY-PRO-LYS | (FOUND 2X) |
| GLY-PHE-PRO | GLY-PRO-PHE | |
| GLY-LEU-ALA | GLY-PRO-VAL | |
| GLY-LEU-PRO | GLY-PRO-ALA | |
| GLY-PHE-LYS | GLY-PRO-GLU | |
| GLY-PHE-LYS | GLY-LYS-LEU | |

TABLE 1-continued

Protected Gly-library Binding with Leucine Enkephalin

| C3 Chain | C7 Chain | |
|---|---|---|
| GLY-PHE-PRO | GLY-PRO-GLU (BRIGHT) | (FOUND 2X) |
| GLY-ASP-VAL | GLY-PRO-GLU | |
| GLY-PHE-SER | GLY-PRO-PHE | |
| GLY-ASP-VAL | GLY-PRO-LEU | |
| GLY-VAL-VAL | GLY-PRO-VAL | |
| GLY-LEU-PRO | GLY-PRO-LEU | |
| GLY-VAL-VAL | GLY-PRO-LYS | |
| GLY-GLU-PRO | GLY-PRO-LEU | |
| GLY-ASP-VAL | GLY-PRO-ALA | |
| GLY-ASP-PRO | GLY-PRO-PHE | |
| GLY-PRO-PRO | GLY-PRO-PHE | |
| GLY-PRO-LYS | GLY-PRO-VAL | |
| GLY-VAL-SER | GLY-SER-GLU | |
| GLY-PHE-SER | GLY-PRO-PHE | |
| GLY-PRO-PRO | GLY-THR-PRO | |
| GLY-LEU-VAL | GLY-LEU-PRO | |
| GLY-SER-ALA | GLY-PRO-ALA | |
| GLY-ALA-PRO | GLY-PRO-PHE | |
| GLY-ASP-PRO | GLY-PRO-LEU | |
| GLY-ASP-VAL | GLY-PRO-THR | |
| GLY-LEU-PRO | GLY-PRO-VAL | |
| GLY-LEU-PHE | GLY-ALA-LYS | |
| GLY-LYS-VAL | GLY-LYS-THR | |
| GLY-PHE-PRO | GLY-PRO-PRO | |

STATISTICS

| | | | | |
|---|---|---|---|---|
| ALA | 2% | 5% | 2% | 7% |
| VAL | 7% | 18% | 0% | 21% |
| LEU | 23% | 0% | 2% | 21% |
| PHE | 27% | 2% | 0% | 16% |
| PRO | 7% | 61% | 86% | 7% |
| SER | 2% | 7% | 2% | 0% |
| THR | 0% | 0% | 2% | 5% |
| LYS | 5% | 7% | 5% | 12% |
| GLU | 2% | 0% | 0% | 14% |
| ASP | 27% | 0% | 0% | 0% |

TABLE 2

Protected Gly-library Binding With Met Enkephalin

| C3 CHAIN | C7 CHAIN | |
|---|---|---|
| GLY-LYS-PRO | GLY-PRO-VAL | |
| GLY-PHE-PRO | GLY-PRO-GLU | (FOUND 2X) |
| GLY-THR-PRO | GLY-ALA-PHE | |
| GLY-PRO-LEU | GLY-PRO-LEU | |
| GLY-ASP-VAL | GLY-PRO-LYS | |
| GLY-PHE-ALA | GLY-PRO-LYS | (FOUND 2X) |
| GLY-PHE-PRO | GLY-PRO-ALA | |
| GLY-PHE-PRO | GLY-PRO-LEU | (FOUND 2X) |
| GLY-LEU-PRO | GLY-PRO-LEU | (FOUND 2X) |
| GLY-PHE-PRO | GLY-PRO-LYS | |
| GLY-PHE-PRO | GLY-PRO-PHE | |
| GLY-LYS-SER | GLY-PRO-LEU | |
| GLY-PRO-GLU | GLY-PRO-PHE | |
| GLY-ASP-PRO | GLY-PRO-VAL | (FOUND 2X) |
| GLY-ASP-PRO | GLY-PRO-LEU | |
| GLY-ASP-PRO | GLY-PRO-PHE | |
| GLY-ASP-PRO | GLY-PRO-GLU | |
| GLY-LYS-SER | GLY-PRO-LYS | |
| GLY-PHE-SER | GLY-PRO-VAL | |
| GLY-THR-PRO | GLY-PRO-LEU | |
| GLY--LEU-ALA | GLY-PRO-PRO | |
| GLY-VAL-PRO | GLY-PRO-PRO | |
| GLY-PRO-PRO | GLY-PRO-PRO | |
| GLY-ALA-LYS | GLY-PRO-VAL | |

TABLE 2-continued

Protected Gly-library Binding With Met Enkephalin

| | | |
|---|---|---|
| GLY-PHE-PRO | GLY-PRO-VAL | |
| GLY-GLU-PRO | GLY-PRO-VAL | |
| GLY-ASP-VAL | GLY-PRO-VAL | (FOUND 2X) |
| GLY-ASP-LEU | GLY-PRO-VAL | (FOUND 2X) |
| GLY-VAL-LYS | GLY-PRO-LYS | |
| GLY--GLU-ALA | GLY-PRO-VAL | |
| GLY-ASP-ALA | GLY-PRO-ALA | |
| GLY-ASP-LEU | GLY-LEU-SER | |
| GLY-LEU-LYS | GLY-ALA-PRO | |
| GLY-ASP-LYS | GLY-ALA-PRO | |
| GLY-PRO-PRO | GLY-ALA-ASP | |
| GLY-VAL-PRO | GLY-ALA-LEU | |
| GLY-ALA-PRO | GLY-VAL-PRO | |
| GLY-PHE-PRO | GLY-VAL-PRO | |
| GLY-ALA-VAL | GLY-VAL-PRO | |
| GLY-ALA-PRO | GLY-GLU-ALA | |
| GLY-THR-PRO | GLY-LYS-VAL | |
| GLY-VAL-LYS | GLY-PHE-ALA | |

Statistics

| | | | | |
|---|---|---|---|---|
| ALA | 8% | 10% | 10% | 8% |
| VAL | 8% | 8% | 6% | 27% |
| LEU | 8% | 8% | 2% | 18% |
| PHE | 24% | 0% | 2% | 8% |
| PRO | 8% | 55% | 86% | 16% |
| SER | 0% | 6% | 0% | 2% |
| THR | 6% | 0% | 0% | 0% |
| LYS | 6% | 10% | 2% | 12% |
| GLU | 4% | 2% | 2% | 6% |
| ASP | 27% | 0% | 0% | 2% |

From Table 1 and 2, proline is the most common amino acid residue in both Leu and Met Enkephalin receptors. Proline, especially at the second position of $C_7$ chain, plays an important role in defining the binding conformation of receptors. However, the second most common amino acid residues are different in Leu and Met Enkephalin receptors. For Leu Enkephalin receptors, they are leucine on the $C_3$ chain and lysine on the $C_7$ chain, but they are aspartic acid on the $C_3$ chain and valine on the $C_7$ chain in Met Enkephalin receptors. Another striking finding is that not one of the receptors against Leu Enkephalin overlaps with those found to recognize Met Enkephalin. This observation implies that the receptors selected by screening may have selectivity to their own ligand.

When treated with Leu Enkephalin 18, the bead containing either protected to deprotected $C_3$—OGLY-Lys-Pro-Lys-Ac, receptor was stained intensively. Thus this receptor was resynthesized on 200 mg of beads to confirm the binding results. After treating 5 mg of the resulting beads with 500 μL, 620 μM solution of Leu Enkephalin 18 at room temperature for 1 hour, the beads collected all the color substrates from the solution and the solution became colorless. Another 5 mg of the above beads was treated with 500 μL, 620 μM solution of Met Enkephalin, after 2 hours at room temperature, the beads became red color and the solution was slightly orange. Although no quantitative measurement of the selective binding of $C_3$—OGLY-Lys-Pro-Ac, $C_7$—OGLY-Pro-Lys-Ac receptor to Leu and Met Enkephalin were performed. It appears that the receptor bound Leu Enkephalin will be further increased by making a more diverse library. This can be easily achieved by using more chemical steps to extend the peptide chains and more monomers in each step.

The Pro-library was screened by Leu Enkephalin 18 and Met Enkephalin 19. There were about 0.75% beads stained by Leu Enkephalin and 0.4% by Met Enkephalin.

The results are listed in Table 3 and 4. The sequences of receptors are listed in the experimental section.

TABLE 3

Protected Pro-library Binding With Leu Enkephalin (32 retrieved beads).

L-Proline, 15 beads

| C₃ Chain | C₇ Chain |
|---|---|
| L-PRO-VAL-VAL | GLY-ALA-ALA |
| L-PRO-VAL-LYS | GLY-ALA-ALA |
| L-PRO-PHE-LYS | GLY-ALA-ALA |
| L-PRO-GLU-LYS | GLY-SER-ALA |
| L-PRO-ALA-PHE | GLY-SER-ALA |
| L-PRO-THR-ALA | GLY-SER-ALA |
| L-PRO-THR-ALA | GLY-PHE-ALA (X2) |
| L-PRO-THR-PHE | GLY-PHE-ALA |
| L-PRO-PHE-PHE | GLY-PHE-ALA |
| L-PRO-SER-ALA | GLY-LYS-ALA |
| L-PRO-VAL-ALA | GLY-LYS-ALA |
| L-PRO-SER-LYS | GLY-VAL-VAL |
| L-PRO-VAL-PHE | GLY-VAL-LYS |
| L-PRO-VAL-VAL | GLY-LYS-LYS |

Statistics

| | | | | |
|---|---|---|---|---|
| ALANINE | 7% | 33% | 20% | 87% |
| VALINE | 20% | 13% | 13% | 0% |
| LEUCINE | 0% | 0% | 0% | 0% |
| PHENYLALANINE | 13% | 27% | 27% | 0% |
| PROLINE | 0% | 0% | 0% | 0% |
| SERINE | 13% | 0% | 20% | 0% |
| THREONINE | 27% | 0% | 0% | 0% |
| LYSINE | 0% | 27% | 13% | 13% |
| GLUTAMIC ACID | 7% | 0% | 0% | 0% |
| ASPARTIC ACID | 0% | 0% | 0% | 0% |

D-Proline, 17 beads

| C₃ Chain | C₇ Chain |
|---|---|
| D-PRO-SER-LYS | GLY-ALA-ALA (X2) |
| D-PRO-ALA-ALA | GLY-ALA-ALA |
| D-PRO-SER-PHE | GLY-GLU-ALA |
| D-PRO-SER-ALA | GLY-GLU-ALA |
| D-PRO-SER-GLU | GLY-SER-ALA |
| D-PRO-SER-ALA | GLY-SER-ALA |
| D-PRO-PHE-PHE | GLY-SER-ALA |
| D-PRO-PHE-LYS | GLY-PHE-ALA (X2) |
| D-PRO-SER-LYS | GLY-PHE-ALA |
| D-PRO-SER-GLU | GLY-PHE-ALA |
| D-PRO-VAL-VAL | GLY-LYS-ALA |
| D-PRO-THR-LYS | GLY-GLU-ALA |
| D-PRO-ALA-LYS | GLY-GLU-GLU |
| D-PRO-VAL-ALA | GLY-PHE-GLU |

Statistics

| | C₃ Chain | | C₇ Chain | |
|---|---|---|---|---|
| Ala | 12% | 35% | 18% | 88% |
| Val | 12% | 0% | 0% | 0% |
| Leu | 0% | 0% | 0% | 0% |
| Phe | 24% | 12% | 35% | 0% |
| Pro | 0% | 0% | 0% | 0% |
| Ser | 47% | 0% | 18% | 0% |
| Thr | 6% | 0% | 0% | 0% |
| Lys | 0% | 41% | 6% | 0% |
| Glu | 0% | 12% | 24% | 12% |
| Asp | 0% | 0% | 0% | 0% |

TABLE 4

The selected receptors from Pro-library for Met Enkephalin are shown below:

L-Proline (6 beads)

| C3 Chain | C7 Chain |
|---|---|
| L-PRO-ASP-PRO | GLY-PRO-PRO |
| L-PRO-VAL-PHE | GLY-ALA-ALA |
| L-PRO-GLU-THR | GLY-ALA-ALA |
| L-PRO-LEU-PRO | GLY-LEU-ALA |
| L-PRO-ALA-PRO | GLY-PRO-ALA |
| L-PRO-GLU-ALA | GLY-LYS-PRO |

Statistics

| | C₃ Chain | | C₇ Chain | |
|---|---|---|---|---|
| Ala | 16% | 16% | 32% | 66% |
| Val | 16% | 0% | 0% | 0% |
| Leu | 16% | 0% | 16% | 0% |
| Phe | 0% | 16% | 0% | 0% |
| Pro | 0% | 48% | 32% | 33% |
| Ser | 0% | 16% | 0% | 0% |
| Thr | 0% | 0% | 0% | 0% |
| Lys | 0% | 0% | 16% | 0% |
| Glu | 32% | 0% | 0% | 0% |
| Asp | 16% | 0% | 0% | 0% |

D-Proline (10 beads)

| C3 Chain | C7 Chain |
|---|---|
| D-PRO-ALA-ALA | GLY-PHE-ALA |
| D-PRO-THR-LYS | GLY-PHE-ALA |
| D-PRO-LEU-PRO | GLY-PRO-PRO |
| D-PRO-ALA-PRO | GLY-ALA-ALA |
| D-PRO-PRO-PRO | GLY-PHE-ALA |
| D-PRO-SER-ALA | GLY-ALA-ALA |
| D-PRO-PRO-PRO | GLY-LYS-GLU |
| D-PRO-ALA-ALA | GLY-ALA-ALA |
| D-PRO-THR-ALA | GLY-ALA-PRO |

Statistics

| | C₃ Chain | | C₇ Chain | |
|---|---|---|---|---|
| Alanine | 40% | 50% | 50% | 60% |
| Valine | 0% | 0% | 0% | 0% |
| Leucine | 10% | 0% | 30% | 0% |
| Phenylalanine | 0% | 0% | 0% | 0% |
| Proline | 20% | 40% | 10% | 30% |
| Serine | 10% | 0% | 0% | 0% |
| Threonine | 20% | 0% | 0% | 0% |
| Lysine | 0% | 10% | 10% | 0% |
| Glutamic acid | 0% | 0% | 0% | 10% |
| Aspartic acid | 0% | 0% | 0% | 0% |

In contrast to the Gly-library, the most common residue in Proline-library is alanine at the third position on $C_7$ chain. Proline becomes one of the least common residues in Leu Enkephalin receptors. Again Leu and Met Enkephalin receptors do not have a common sequence.

The actual binding mode for our receptors binding Enkephalin is still unknown and very difficult to ascertain. However, our "artificial antibody" has been shown to be very promising in recognition of Leu and Met Enkephalin. It may provide an efficient chemical method to distinguish very subtle differences between molecules.

The subtle difference between Leu and Met make them very difficult to be recognized even by a natural receptor, and is almost impossible for rational design to develop receptors for then. Therefore, the methods described above may allow the development of receptors for almost any substrates even without knowing the exact shape, size and arrangement of functionalities involved.

Some additional binding studies for Peptidosteroidal receptors with beta-Casomorphinamide and Des-Tyr Leu Enkahphalin, are shown in the following table 5 and are compared to the Leu Enkaphalin and Met Enkaphalin.

EXAMPLE 2

Preparation of a Gly-Deoxycholic Acid Library

A Gly-deoxycholic acid library was prepared by essentially the same procedure as described for the chenodeoxycholic acid library except deoxycholic acid was used in place of chenodeoxycholic acid (Scheme 4).

In the first step deoxycholic acid was attached to the aminomethyl resin after activation with DIC. The 3-hydroxyl group was then reacted with Fmoc-Gly F. After Fmoc deprotection two amino acids were added in two split synthesis steps using ten amino acids with each step performed in ten separate reaction vessels. Each step was encoded as described for the chenodeoxycholic acid example. The amino acids used were Ala, Val, Leu, Phe, Pro, Ser, Thr, Lys, Glu, Asp.

Fmoc-GlyF was then allowed to react with the C-ring hydroxyl group as described for the C.,hydroxy in the chenodeoxycholic acid example. After Fmoc deprotection the same ten amino acids were introduced in two encoded split synthesis steps. The resulting $C_3$—OGlyAA$_1$AA$_2$AC, $C_{11}$—OGlyAA$_3$AA$_1$Ac deoxycholic acid was deprotected as described for the chenodeoxycholic acid library.

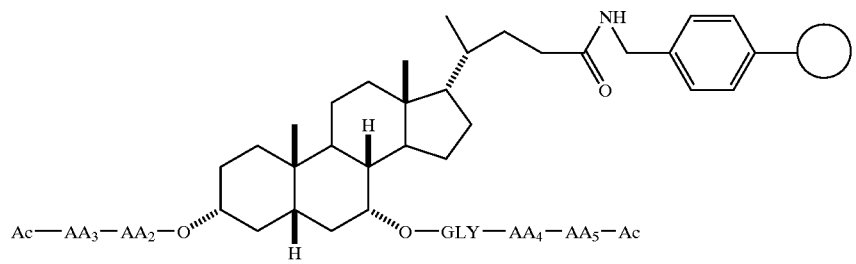

TABLE 5

| PEPTIDOSTEROIDAL RECEPTORS WHICH SELECTIVELY BIND OPIOID PEPTIDES | | | | | | | |
|---|---|---|---|---|---|---|---|
| SUBSTRATE | BOUND | AA1 | AA2 | AA3 | AA4 | AA5 | $K_{D\text{-}MAX}$ |
| β-Casomorphinamide (Dye-TYR-PRO-PHE-NH$_2$) | 0.3% | GLY | PHE | PHE | ALA | ALA | 407 μM |
| Dee-TyR Leu Enkephalin (Dye-GLY-GLY-PHE-LEU) | 0.1% | GLY | LYS | ALA | ALA | LYS | 141 μM |
| Leu Enkephalin (Dye-TYR-GLY-GLY-PHE-LEU) | 0.7% | GLY | ASP | PRO | PRO | LEU | 81 μM |
| Met Enkephalin (Dye-TYR-GLY-GLY-PHE-MET) | 0.5% | GLY | PHE | PRO 95% | PRO | LEU | 85 μM |
|  | 0.8% | PRO | THR | LYS | PHE | ALA 90% | 75 μM |

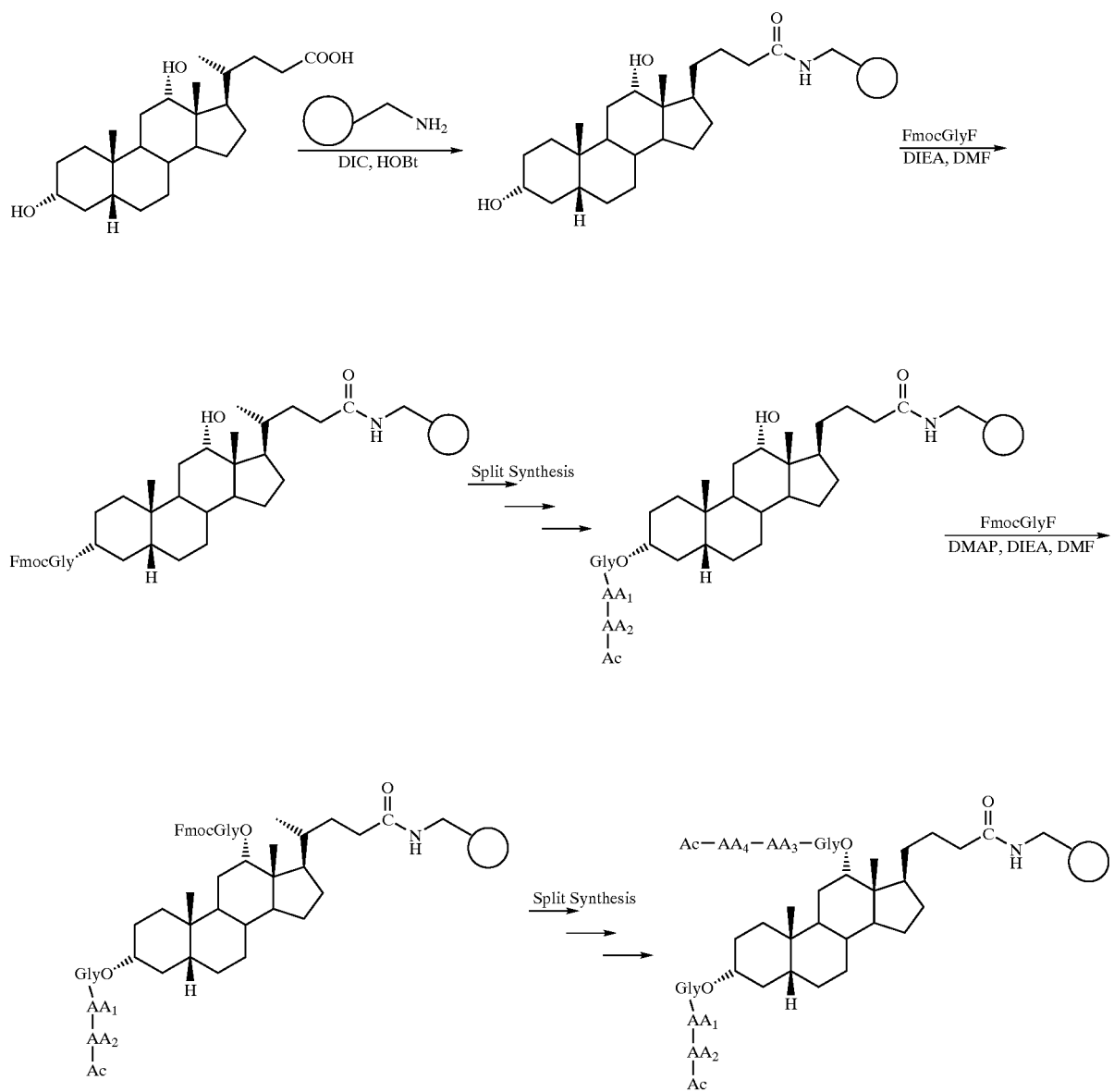
EXAMPLE 3
Preparation of a Macrocyclic Synthetic Receptor
Preparation of a Macrocyclic Synthetic Receptor
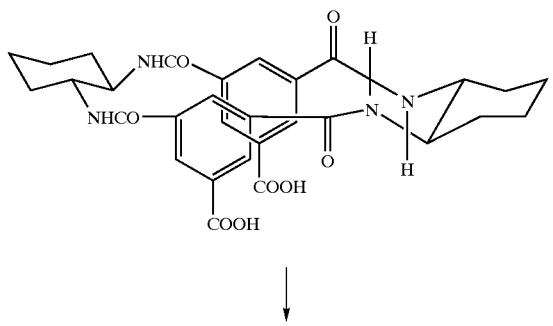

-continued
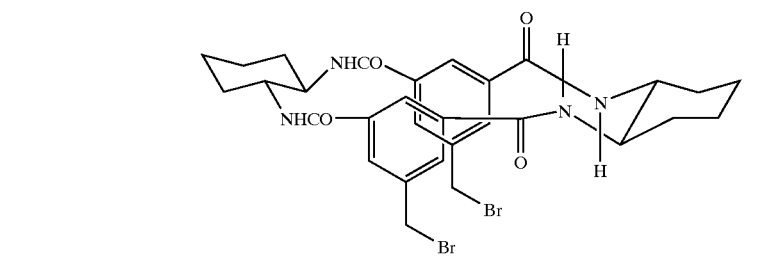
1) Cyclize to symetrical diam:
2) Monoprotect
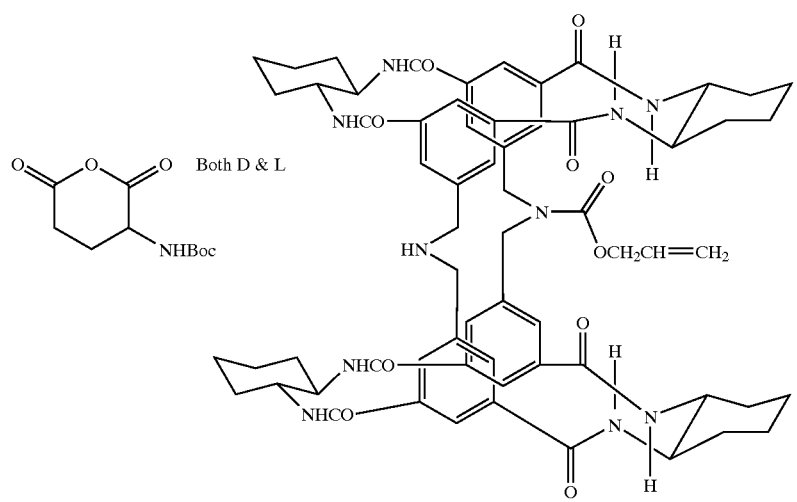
1) Couple anhydride
2) ◯—NH₂
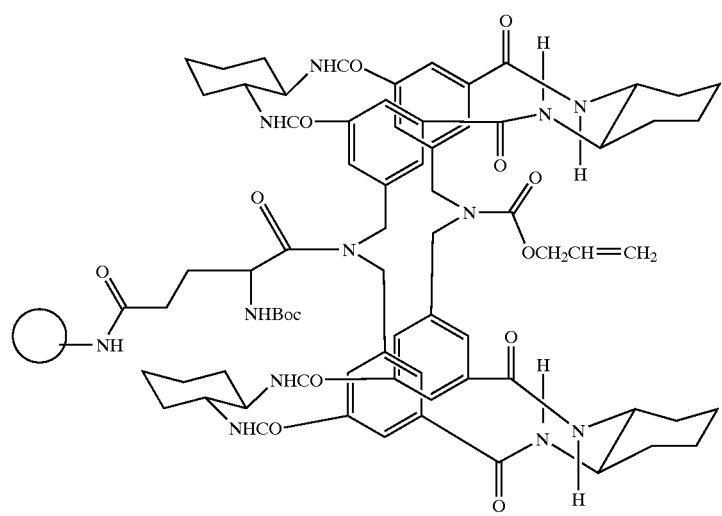
1) Attach to resin
2) Remove Boc and grow VaVbVc
   (Fmoc chemistry, BOC sidechain protect:
3) Remove Alloc and grow VxVyVz

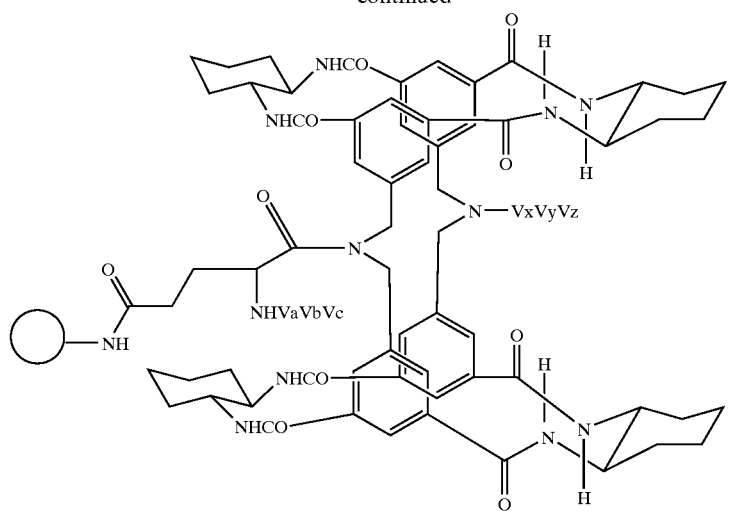

EXAMPLE 4

Cyclooligomeric Receptors Based on Trimesic Acid and 1,2-Diamines. Minimal Structure for Sequence-Selective Peptide Binding The receptor libraries described below have macrocyclic 'ligomer arms'—this makes them conformationally less flexible and results in more selective receptors. Note however, that it is not a requirement that the receptor oligomer arms are macrocyclic.

Macrotricyclic receptors 1 having stoichiometry $A_4B_6$ and prepared from trimesic acid ($A(OH)_3$) and certain chiral 1,2-diamines (e.g. $BH_2$) have been previously shown to bind various peptides with remarkable selectivity. The simplified analogs 1, the macromonocycles 2 & 3 and macrobicycles 4–6, and the minimal structure required for selective peptide binding is described.

In recent reports a number of $D_2$-symmetric, macrotricyclic receptors (1) that are simple $A_4B_6$ cyclooligomers of trimesic acid ($A(OH)_3$) and 1,2-diamines (e.g. $BH_2$, $B'H_2$) have been described. (Yoon, S. S. and Still, W. C., *J. Am. Chem. Soc.* 1993, 115, 823; Yoon, S. S. and Still, W. C., *Tetrahedron Lett.* 1994, 35, 2117; Yoon, S. S. and Still, W. C., *Tetrahedron*, in press.) Such receptors are easy to prepare and have been found to bind certain peptides in organic solvents with high enantio- and sequence-selectivity. For example, 1 binds certain amino acid derivatives containing L-valine or L-phenylglycine residues with enantioselection exceeding 2 kcal/mol and displays a particular affinity for the sidechain-protected tripeptide sequence (D)Asn(N-Tr)-(L)Val-(L)Ser(O-tBu) in $CHCl_3$. Because 1 is among the most sequence-selective peptide receptors yet prepared by synthesis, a study was carried out to determine the smallest, readily preparable substructure of 1 that retains selective peptide binding properties.

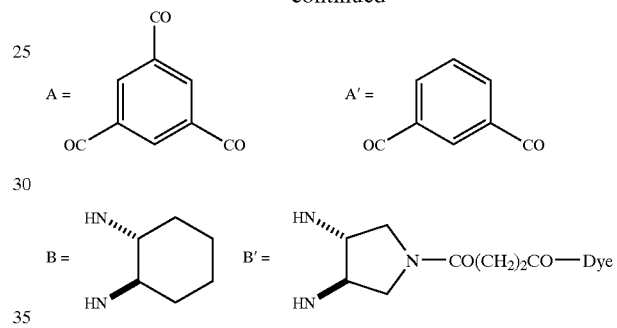

Thus, the peptide binding properties of the related macromonocycles 2 and 3 and macrobicycles 4 and 5 were prepared and surveyed. It was found that highly selective peptide binding properties are not limited to macrotricycles like 1.

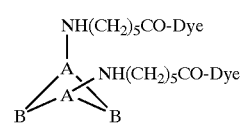

2

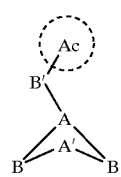

3

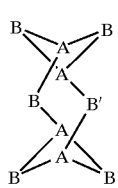

1

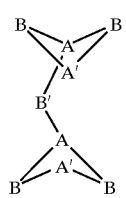

4

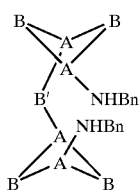

Dye-labeled receptor substructures 2–5 were prepared using the following methodology developed for the synthesis of 1 (Yoon, S. S. and Still, W. C., *Tetrahedron*, in press.).

To test each of these compounds for their general ability to bind peptidic substrates, the previously described solid phase color assay employing a library of ~50,000 (maximally $15^4$=50,625) acylated tripeptides prepared on polystyrene beads by encoded split synthesis was used. (A. Borchardt and W. C. Still, *J. Am. Chem. Soc.*, 1994, 116, 373; see A. Borchardt and W. C. Still, *J. Am. Chem. Soc.*, 1994, 116, 7467; all possible combinations of R=methyl (Me), ethyl (Et), isopropyl (iPr), t-butyl (tBu), neopentyl (neoPe), trifluoromethyl ($CF_3$), isobutyl (iBu), methoxymethyl (MOM), acetoxymethyl (AcOM), cyclopropyl (cPr), cyclobutyl (cBu), cyclopentyl (cPe), phenyl (Ph), morpholino (Morph), dimethylamino ($Me_2N$) and AA1-AA$_3$= Gly, D-Ala, L-Ala, D-Ser(OtBu), L-Ser(OtBu), D-Val, L-Val, D-Pro, L-Pro, D-Asn(N-trityl), L-Asn(N-trityl), D-Gln(N-trityl), L-Gln(N-trityl), D-Lys(N-Boc), and L-Lys (N-Boc); Ohlmeyer, M. H. J., Swanson, R. N., Dillard, L. W., Reader, J. C., Asouline, G., Kobayashi, R., Wigler, M. and Still, W. C., *Proc. Natl. Acad. Sci. USA* 1993, 90, 10922.) Each member of the library was attached to a different bead and had the general structure:

R(C=O)-AA$_3$-AA$_2$-AA1-NH(CH$_2$)$_5$CONH-polystyrene

Peptide binding surveys were performed by equilibrating 10–500 μM 2–5 in CHC$_3$ with the substrate library for 48 hours. Binding for a given substrate library bead was indicated when a bead concentrated the color of the receptor and its tethered dye. The structures of the acylated tripeptides on the most deeply colored beads were then determined by ECGC decoding. (Ohlmeyer, M. H. J., Swanson, R. N., Dillard, L. W., Reader, J. C., Asouline, G., Kobayashi, R., Wigler, M. and Still, W. C., *Proc. Natl. Acad. Sci. USA* 1993, 90, 10922.)

The results from these binding studies were very clear. The macromonocyclic receptor fragments 2 and 3 showed no evidence of binding to the peptide library even at receptor concentrations as high as 500 μM. This result indicates that no member of the library bound either of these single-armed receptor fragments with $K_a$'s exceeding ~200 in CHCl$_3$. (Previous studies have shown that beads binding a dyed receptor can be readily detected when as little as 5–10% of the available substrates on the bead are bound.) In contrast, the double-armed, macrobicyclic receptors 4 and 5 did bind peptides in the substrate library. Indeed, both showed highly selective binding of certain peptides at receptor concentrations of 38 and 4 μM respectively. The substrate selectivity with 4 was particularly high—there was a very large color contrast between receptor bound and unbound beads, and only one bead per ~2500 beads was stained by the dye-linked receptor. This level of selection indicates that only ~23 members of the entire 50,000-member peptide library are bound by 4 at ~40 μM concentration in CHCl$_3$. With 5, there was a greater gradation of color intensities among the stained beads and one bead per ~500 was stained. In comparison, macrotricycle 1 has been reported to bind one bead per ~1000 at a receptor concentration of 20 μM. (Yoon, S. S. and Still, W. C., *Tetrahedron*, in press.) Thus not only do these simplified receptors bind peptides effectively, but one of them (4) binds peptides with substantially more selectivity than does 1.

Further simplifications of the structural motif found in 4 and 5 can be made. In particular, it is possible to eliminate the conformation-restraining ring of the central linker B' and still retain selective binding properties. Thus the pyrrolidine linker of 4 was replaced with a more flexible acyclic diamine derived from tartaric acid to create 6. (Yoon, S. S. and Still, W. C., *Tetrahedron Lett.* 1994, 35, 2117.) Like 4 and 5, receptor 6 also showed highly selective binding. This selectivity corresponded to peptide binding at a level of one bead per ~900 (at [6]=40 μM). These binding properties make 6 somewhat less selective than 4, but they are still comparable to those of the structurally more complex 1.

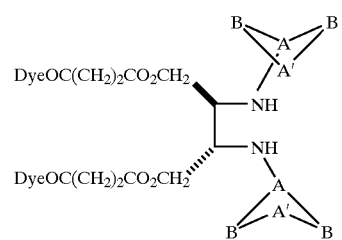

The structures were determined for the peptide substrates preferentially bound by 4–6 by picking ~50 of the most deeply stained beads from the assay of each receptor and decoding by ECGC. The results are listed in Table 6 in terms of the frequencies of the most commonly occurring peptide sequences along with comparison data for the parent receptor 1. Because the peptide library consists of all possible tripeptides having 15 different residues at each site, the expected occurrence frequencies of any di- or tripeptide for unselective binding can be computed, and that data is also listed in the table. As indicated, little selectivity for the terminal acyl group (R) is apparent but the receptors do bind the peptidic domains of the substrate library with very high sequence selectivity. The peptide binding properties of 4 are particularly noteworthy in that 78% of the selected beads carried only two tripeptide sequences.

TABLE 6

Sidechain-protected Peptides Selectively Bound by Receptors 4, 5, 6 and 1.[a]

| R | AA3 | AA2 | AA1 | Frequency Found[b] | Frequency Expected[c] |
|---|---|---|---|---|---|
| Macrobicyclic Receptor 4 | | | | | |
| X | (D)Pro | (L)Val | (D)Gln | 39% | 0.03% |
| X | (L)Lys | (L)Val | (D)Pro | 39% | 0.03% |
| Macrobicyclic Receptor 5 | | | | | |
| X | Gly | (L)Ala | (L)Ser | 16% | 0.03% |
| X | X | (L)Ala, (L)Lys, (L)Val | (D)Gln | 53% | 1.3% |

TABLE 6-continued

Sidechain-protected Peptides
Selectively Bound by Receptors 4, 5, 6 and 1.[a]

| R | AA3 | AA2 | AA1 | Frequency Found[b] | Frequency Expected[c] |
|---|---|---|---|---|---|
| | | Macrobicyclic Receptor 6 | | | |
| X | (L)Asn | (L)Pro | (D)Gln | 25% | 0.03% |
| X | (L)Pro | (L)Asn | (D)Gln | 13% | 0.03% |
| X | (D)Pro, (D)Val, (D)Gln | (L)Val | (D)Gln | 47% | 0.09% |
| | | Macrotricyclic Receptor 1[c] | | | |
| X | (D)Asn, (D)Gln | (L)Val | (L)Ser, Gly | 34% | 0.12% |
| X | (L)Val | (D)Asn | X | 10% | 0.44% | a. X indicates all possible residues (i.e. little or no selectivity); b. percentage of beads selected by receptor binding assay with indicated peptide sequence; c. percentage of beads having indicated peptide sequence in library (expectation frequency for random bead picking).

It is significant that the minimal structure having significant peptide binding properties is quite simple. In particular, each of the two-armed receptors 4–6 can be considered to be constructed from three distinct modules (a template and two oligomer arms) that are held together by simple, acyclic amide bonds. As such, receptors of this type should be readily preparable as combinatorial libraries using split synthesis starting from a variety of templates and oligomer arms. (For a more conformationally flexible, double-armed receptor library see: Boyce, R., Li, G., Nestler, H. P., Suenaga, T. and Still, W. C., *J. Am. Chem. Soc.* 1994, 116, 7955.) It is also significant that each of these receptors had its own distinct peptide binding selectivity.

These experiments have established the minimal, two-armed structure that is necessary to bind peptides with 1-like receptors (also see Scheme 1). Libraries of these receptors include members having substantial selectivities for given peptidic substrates. These experiments demonstrate the first step of a protocol for finding receptors that bind desired substrates tightly and selectively. The method comprises the steps of: 1) synthesizing of examples of a new receptor family and screening against a library of the desired substrate type, 2) synthesizing of a receptor library based on structures showing selective binding in step 1 and screening with the substrate for which selective binding is desired, and 3) resynthesizing of individual receptors found in step 2 and screening against the substrate library of step 1 to establish selectivity.

Synthesis of Combinatorial Library of 2-Armed Receptors with Macrocyclic Oligomer Arms.

The libraries are prepared by solid phase split synthesis using the techniques described in the preparation of the above-described peptidosteroidal library but with different starting materials. The preparation consists of the following steps:

Step 1. A set of diverse, different templates having the following general structure is prepared (also see Scheme 1).

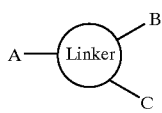

where A is a functional group that allows attachment of the template to a support for solid phase synthesis (e.g. Merrifield polystyrene beads), B and C are functional groups that allow attachment of the two oligomer arms of the receptors. B and C may be the same functional group in which case the two receptor oligomer arms are the same. Alternatively, B and C may be different (or may be differentially protected) in which case the two receptor oligomer arms are different and this is a preferred embodiment.

Step 2. A set of diverse, different oligomer arms having the following general structure is prepared

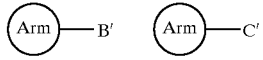

Where B' and C' are functional groups that allow attachment of the oligomer arms to template functional groups B and C respectively. The oligomer arms may be acyclic, cyclic or macrocyclic but oligomer arms with the least conformational flexibility are preferred. Oligomer arms with one or more functional groups (other than B' and C') are also preferred (because the functional group may become involved in specific interactions with the substrates ultimately bound by the receptor).

Step 3. Attach each template from step 1 using functional group A to a different portion of solid phase synthesis support particles (here designated P) (e.g.

Merrifield polystyrene beads, poly(ethylene glycol) polystyrene copolymer beads, polydimethylacrylamide beads) to give:

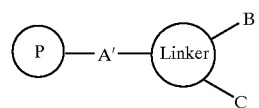

where A' is the chemical moiety that results from attaching A to P.

Step 4. All of the different portions of the synthesis support particles (P) from Step 3 are mixed and then distributed equally into N different reaction vessels where N is the number of different, first arm units (arm-B') to be added to the P-bound template. The template B functional groups are deprotected or activated as necessary to allow reaction with B' and coupled to a different arm-B' in each different reaction vessel to give:

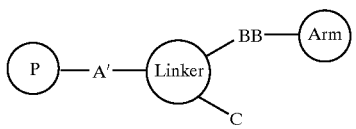

where BB is the chemical moiety that results from coupling B and B' and chemically binds template units to the first arm units. (This is the first step of combinatorial, split synthesis). Optionally, the first arm unit may be further modified by chemical reactions after coupling to the template. Such chemical reactions may be by standard synthesis or by combinatorial synthesis (in which case the number of different compounds made will be increased).

Step 5. All the different portions of the synthesis support particles (P) from Step 4 are mixed and then distributed equally into N' different reaction vessels where N' is the number of different, second arm units (Arm-C') to be added to the template. The template C functional groups are deprotected or activated as necessary to allow reaction with C' and coupled to a different arm-C' in each different reaction vessel to give:

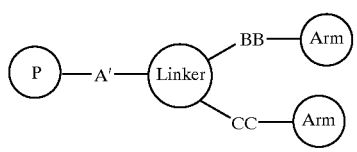

where CC is the chemical moiety that results from coupling C and C' and chemically binds template units to the second arm units. (This is the second step of combinatorial, split synthesis)

Optionally, the second arm unit can be further modified by chemical reactions after coupling to the template. Such chemical reactions may be by standard synthesis or by combinatorial synthesis (in which case the number of different compounds made will be increased).

Optionally, if the original template had been equipped with three or more functional groups for attaching oligomer arms, then one or more additional steps analogous to Step 5 could be carried out to attach three or more oligomer arms to the template.

The above steps create a library of synthetic receptors on particles that may be screened for valuable properties (selective ligand or substrate binding, catalysis of certain chemical reactions, selective binding to biological molecules, selective binding to supramolecular structures (e.g. cells), etc.). Once a particle has been found that carries a synthetic receptor having the valuable property, the structure of that receptor can be determined and the receptor resynthesized on large scale. The receptor structure determination can be accomplished by direct analysis of the receptor (e.g. mass spectroscopy) or by molecular tag analysis in the case of an encoded library preparation.

Specific Example of Receptor Library Synthesis as Generally Described Above.

In the following steps, a molecular encoding scheme is employed as used in the peptidosteroidal library synthesis to allow for structure elucidation of the final receptor library members.

Step 1. The following templates as outlined below are prepared.

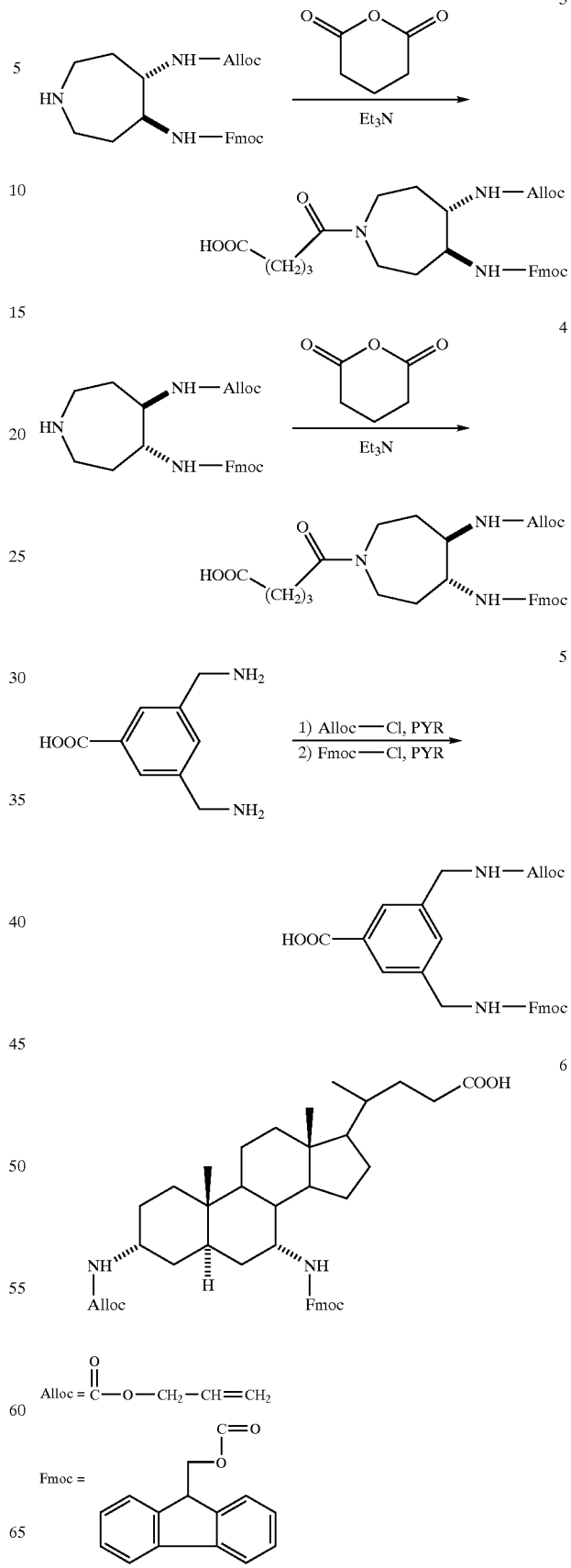

Step 2. The following arm structures have been prepared.

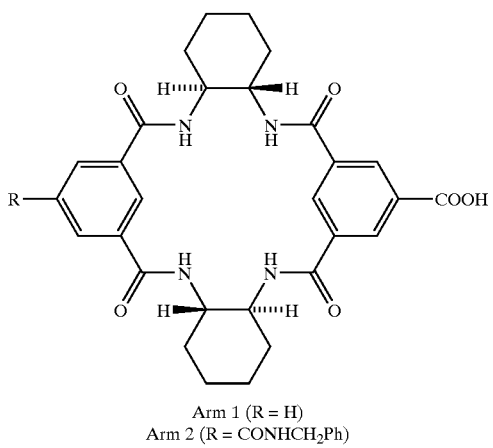

Arm 1 (R = H)
Arm 2 (R = CONHCH$_2$Ph)

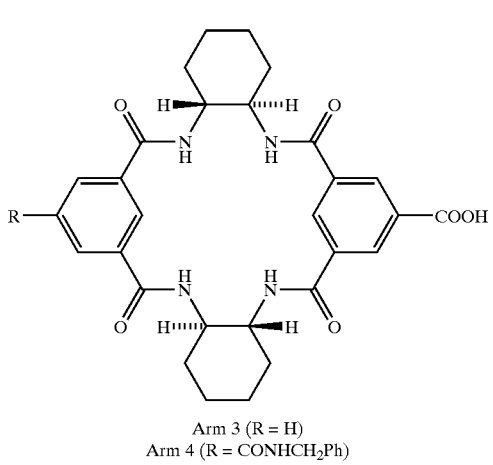

Arm 3 (R = H)
Arm 4 (R = CONHCH$_2$Ph)

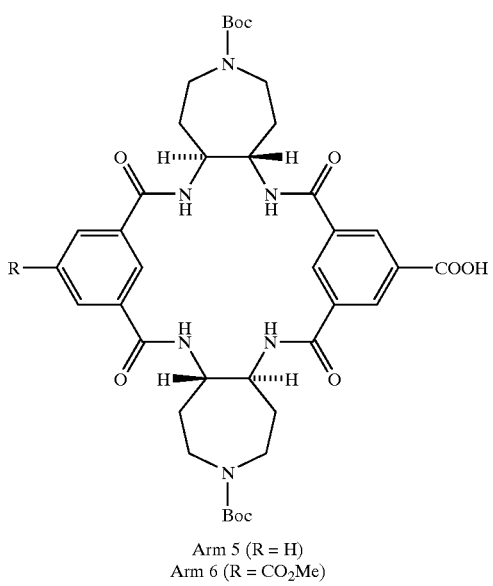

Arm 5 (R = H)
Arm 6 (R = CO$_2$Me)

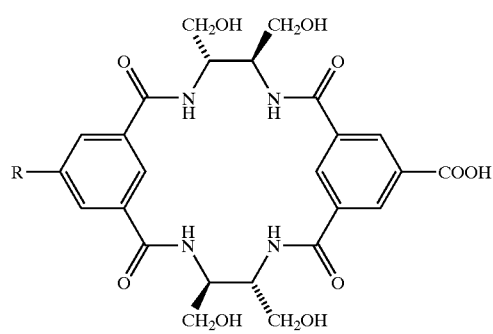

Arm 7 (R = H)
Arm 8 (R = CONHCH$_2$Ph)

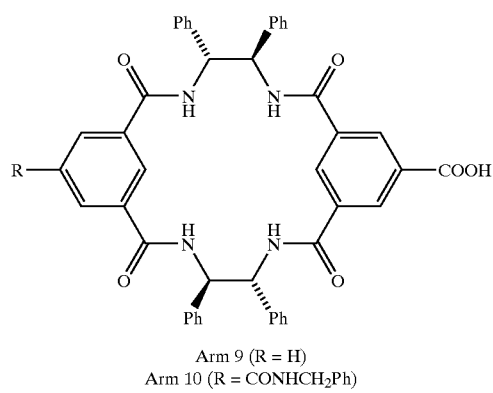

Arm 9 (R = H)
Arm 10 (R = CONHCH$_2$Ph)

Step 3. The templates from step 1 will be chemically attached using diisopropylcarbodiimide (DIC) to NH$_2$-functionalized TENTAGEL™ (Poly(ethylene glycol)-polystyrene copolymer) beads (P in the general scheme above).

For example yielding:

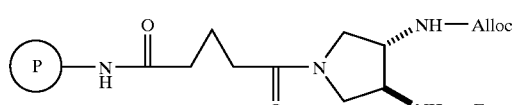

Step 4. The first functional group (Fmoc-protected amine, B in the general scheme above) on the template is deprotected using piperidine and DIC is used to couple each of the oligomer arms (COOH=B') to the template. This results in synthesis of all possible combinations of the templates of step 1 and the oligomer arms of step 2. For example, coupling of the first template and the first arm results in the synthesis of the following receptor intermediate:

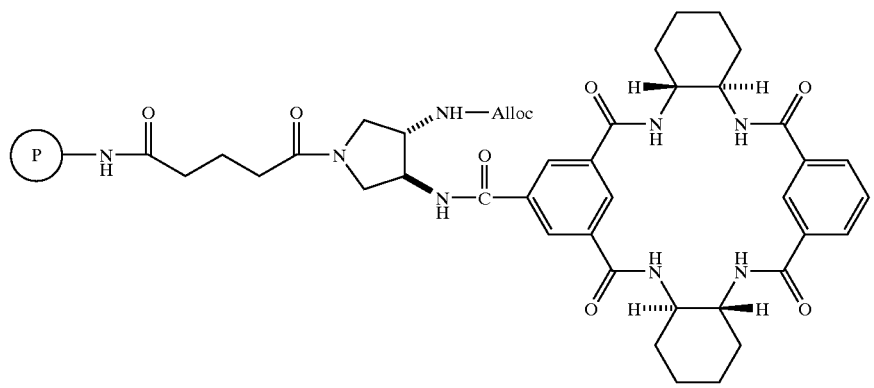

Step 5. The second functional group is deprotected (Alloc-protected amine, C in the general scheme above) using Pd(PPh₃)₄ and DIC is used to couple each of the oligomer arms (COOH=C') to the template. This results in the synthesis of all possible combinations of the templates of step 1 and all pairs of the oligomer arms of step 2. For example, coupling the first template and the first arm in both steps 4 and 5 results in the synthesis of the following receptor:

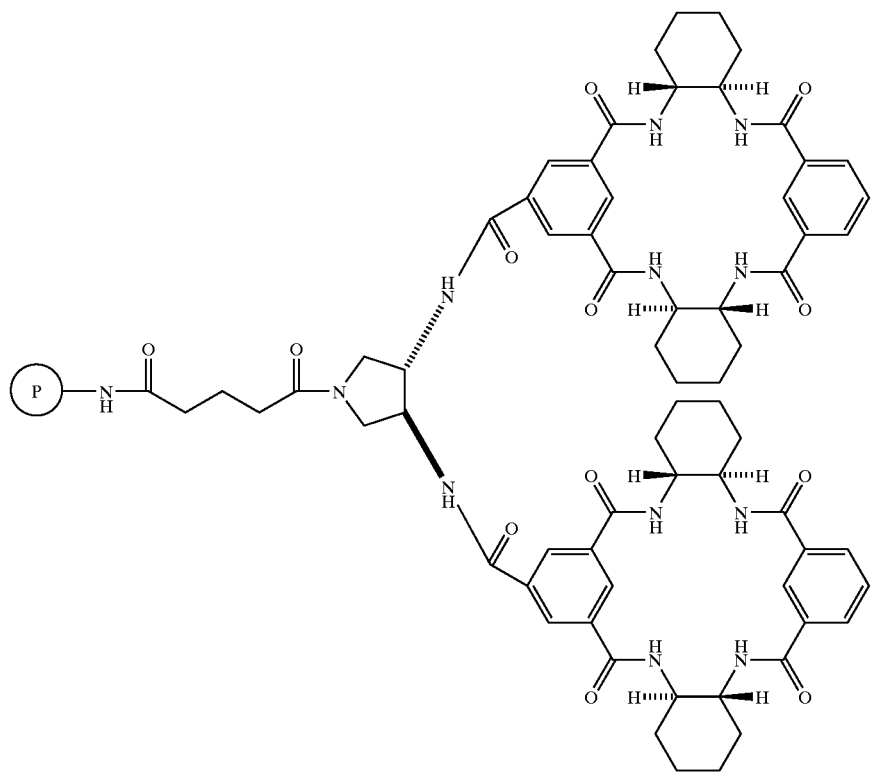

Using the 6 different templates and the 10 different oligomer arms shown above in the combinatorial split synthesis described above, the total number of different receptor in the resulting synthetic receptor library is 600 (6×10×10).

Different and/or Larger Receptor Libraries.

By using a larger number of templates and/or oligomer arms, much larger libraries can be prepared using the split synthesis method described above. While an almost a very large number of template and arm structures may be imagined, structures will generally have the following properties are favored:

Templates—are conformationally restrained (as the cyclic templates shown below). The templates have short chains of atoms (no more than 10) between functional groups used to attach oligomer arms (as the cyclic and acyclic templates shown below). In addition, the templates have functional groups that allow attachment of more than one arm. The receptors having more than two oligomer arms will be at least as selective as the two-armed receptors (see examples of templates suitable for preparation of 3-armed receptors see the following).

Oligomer arms—are conformationally restrained: and include macrocyclic molecules, polycyclic molecules, branched cyclic molecules, and branched acyclic molecules. The oligomer arms have a range of functional groups for specific interaction with bound substrates—substrates, e.g. functional groups that are ionic (e.g. organic ammonium, carboxylate, phosphate, sulfonate, sulfonamide ions) or are hydrogen bond donors or acceptors (e.g. ketones, esters, amides, alcohols, ethers, phosphonamides, sulfonamides, sulfoxides, sulfones, imines, amines, amine oxides, heterocycles, halogens) may be particularly valuable for promoting specific receptor-substrate binding.

The following is a non-exhaustive list of templates and oligomer arms that should be useful for preparing receptor libraries.

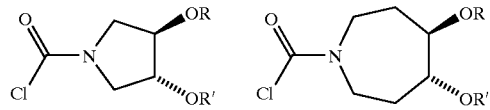

R, R' and R" are suitable protecting groups.

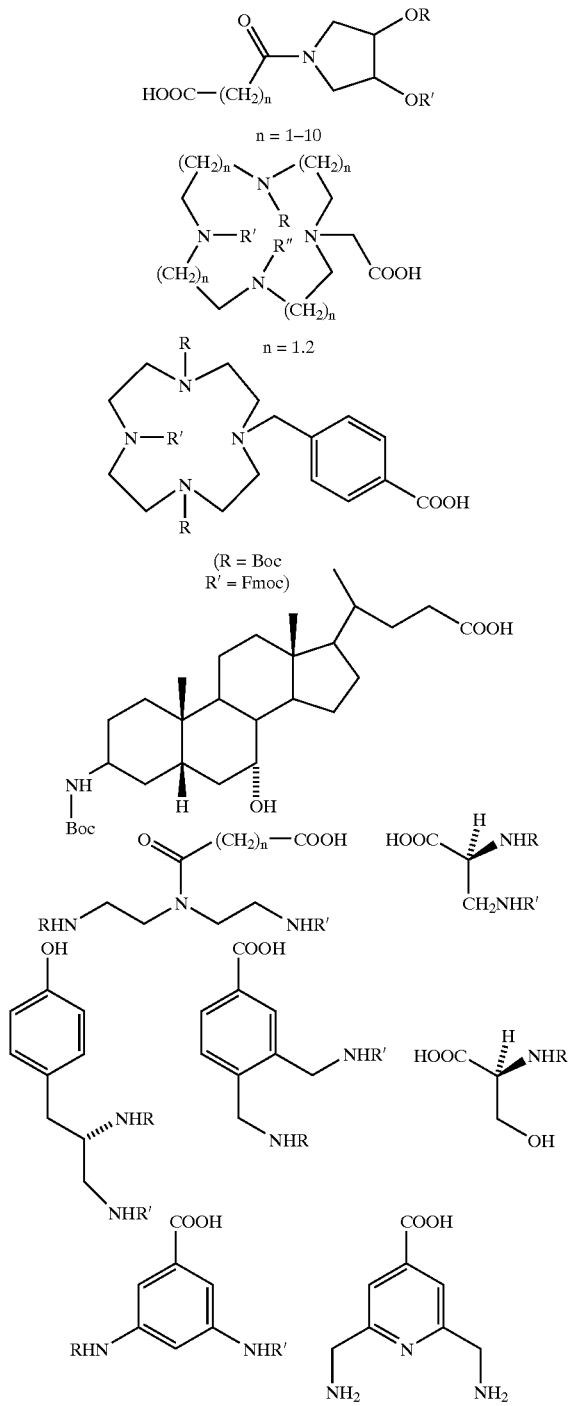

Oligomer arms:

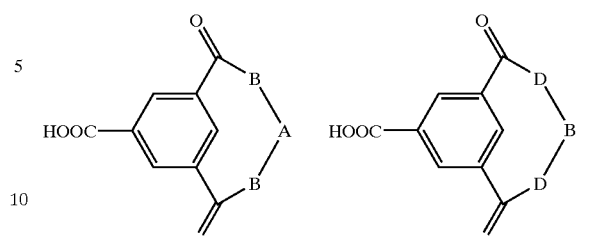

Generally

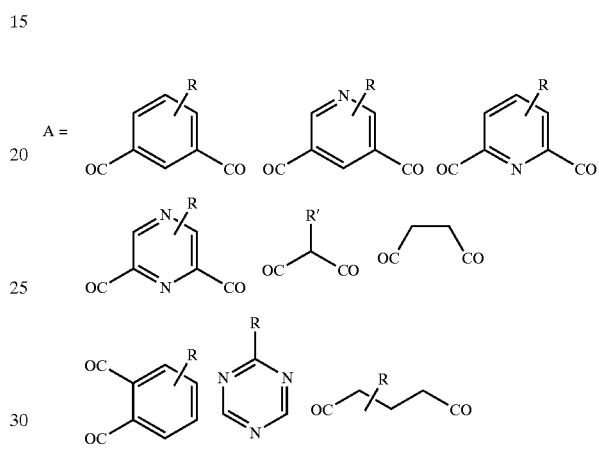

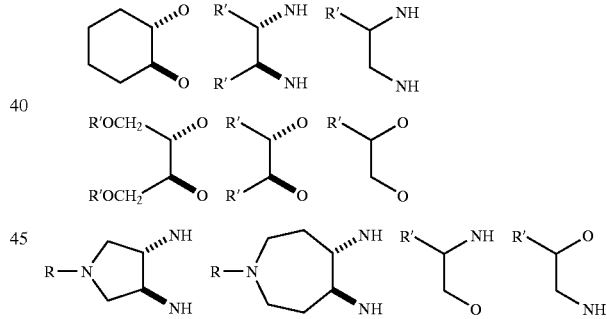

R = H, Alk, Ar, OH, OR.
NH₂, NHR', COOR'.
CONHR', Halogen, NO₂

R' = H, Alkyl, Aryl

R* = OH, SH, Pb, P—OH—Pb.
COOH, CH₂COOH, CONH₂,
CH₂CONH₂, Indole,
Imidazole, Aryl, Alkyl

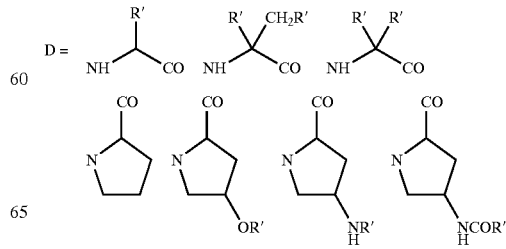

EXAMPLE 5

Preparation of a Double-Armed Receptor

Diamide A 500 mg (0.90 mmol) of bis-pentafluorophenyl monomethyl trimesate and 400 mg (1.98 mmol, 2.2 eq) of mono-Boc-(R,R)-cyclohexanediamine were dissolved in 20 ml $CH_2Cl_2$ and 607 ml (3.60 mmol, 4 eq) $^iPr_2NEt$ were added. After stirring for 16 hours at r.t., the solvent was removed at reduced pressure. Flash chromatography (silica gel, $CHCl_3$/acetone 10:2) afforded 540 mg (97%) of A as an amorphous white solid. $^1$H-NMR (400 MHz, $CDCl_3$): 1.27 (s, 18H), 1.34 (m, 4H), 1.78 (m, 4H), 2.03 (m, 2H), 2.23 (m, 2H), 3.54 (m, 2H), 3.81 (m, 2H), 3.96 (s, 3H), 4.67 (d, J=8.4, 2H), 7.33 (d, J=7.6, 2H), 8.47 (t, J=1.7, 1H), 8.64 (d, J=1.6, 2H). $^{13}$C-NMR (75 MHz, $CDCl_3$): 24.45, 25.01, 28.13, 32.32, 32.46, 52.30, 53.61, 56.14, 79.71, 129.47, 130.90, 134.87, 156.98, 165.26, 165.66. FT-IR (KBr): 3336, 2978, 2935, 2859, 1682, 1654, 1531 cm$^{-1}$. HRMS (M+1): calcd. for $C_{32}H_{49}N_4O_8$ 617.3550, found 617.3533.

Macrocyclic Tetralactam B

To a stirred suspension of 300 mg (1.81 mmol) isophthalic acid in 30 ml $CH_2Cl_2$, 700 mg (3.79 mmol, 2.1 eq) pentafluorophenol and 727 mg (3.79 mmol, 2.1 eq) of EDC were added. After four hours, the reaction mixture became clear indicating completion of the reaction. Removal of the solvent at reduced pressure followed by flash chromatography (silica gel, $CH_2Cl_2$/acetone 20:1) afforded 825 mg (91%) isophthalic bis-pentafluorophenylester as a white solid.

Trifluoroacetic acid (0.5 ml) was added via syringe to a solution of 200 mg (0.32 mmol) A in 4 ml $CH_2Cl_2$. After 2 hr, all volatile materials were removed at reduced pressure. The oily residue was triturated with diethyl ether to yield a white solid that was isolated by decantation and drying in vacuo. A solution of the resulting bis-TFA amine salt and 162 mg (0.32 mmol) of isophthalic bis-pentafluorophenylester in 10 ml dry THF was added dropwise over a 24 hr period to a stirred solution of 220 ml (1.30 mmol, 4 eq) $^iPr_2NEt$ in 300 ml of dry THF. After stirring for an additional 24 hr. the reaction mixture was evaporated at reduced pressure and flash chromatographed (silica gel, $CHC_3$/MeOH first 100:2 then 100:4) to afford 165 mg (93%) of macrocycle B as an amorphous white solid. $^1$H-NMR (400 MHz, $CD_3OD$): 1.47 and 1.58 (m, 8H), 1.87 (m, 4H), 2.12 (m, 4H), 3.92 (s, 3H), 4.02 (m, 4H), 7.45 (t, J=7.7, 1H), 7.87 (dd, J=7.7 and J=1.6, 2H), 8.33 (d, J=1.6, 1H), 8.49 (d, J=1.7, 2H), 8.56 (t, J=1.7, 1H). $^{13}$C-NMR (75 MHz, $CD_3OD$): 26.01, 32.95, 52.99, 55.68, 55.87, 128.23, 129.96, 131.23, 131.86, 132.38, 132.45, 136.01, 136.66, 166.89, 168.79, 169.84. FT-IR (KBr): 3324, 2936, 2859, 1728, 1666, 1648, 1534 cm$^{-1}$. HRMS (M+1): calcd. for $C_{30}H_{35}N_4O_6$ 547.2557, found 547.2578.

Pentafluorophenylester C 127 mg (0.23 mmol) of B were dissolved in 2 ml THF. 2 ml MeOH and 19 mg (0.47 mmol, 2 eq) NaOH dissolved in 1 ml $H_2O$ were added. After 16 hr, the reaction mixture was acidified with 1M HCl and extracted with EtOAc (3×20 ml), the combined organic layers were dried over $MgSO_4$. Filtration and removal of the solvent at reduced pressure yielded the crude acid as a white solid that was suspended in 10 ml $CH_2Cl_2$. 86 mg (0.47 mmol, 2 eq) pentafluorophenol and 89 mg (0.47 mmol, 2 eq) EDC were added. After stirring for 5 hr, most of the solid was dissolved. The solvent was removed at reduced pressure and the residue purified by flash chromatography (silica gel, $CH_2Cl_2$/acetone 10:1) to yield 132 mg (81) of pentafluorophenylester C as a white solid. $^1$H-NMR (400 MHz, $CD_3OD$): 1.46 and 1.57 (m, 8H), 1.86 (m, 4H), 2.13 (m, 4H), 4.02 (m, 4H), 7.50 (t, J=7.7, 1H), 7.88 (dd, J=7.7 and J=1.7, 2H), 8.35 (s, 1H), 8.56 (d, J=7.8, 2H), 8.67 (s, 2H), 8.72 (s, 1H). $^{13}$C-NMR (75 MHz, $CD_3OD$): 25.94, 32.86, 55.74, 56.00, 128.23, 129.01, 129.96, 131.28, 132.79, 134.26, 135.93, 137.25, 137.6, 139.3, 140.9, 142.7, 144.2, 162.65, 168.10, 169.73, 169.81.

FT-IR (KBr): 3323, 2937, 2860, 1768, 1652, 1522 cm$^{-1}$.

HRMS (M+1): calcd. for $C_{35}H_{32}N_4O_6F_5$ 699.2242, found 699.2272.

Receptor 4 (Scheme 5)

To a solution of 8 mg (1.36 mmol) disperse red-labeled R,R-pyrrolidine diamine (S. S. Yoon and W. C. Still, Tetrahedron, in press (1994)) and 20 mg (2.86 mmol, 2.1 eq) pentafluorophenylester C in 0.5 ml $CH_2Cl_2$, 9 ml (5.44 mmol, 4 eq) $^iPr_2NEt$ were added and the reaction mixture was allowed to stir for 24 hr. The entire reaction mixture was subjected to flash chromatography (silica gel, $CHCl_3$/MeOH 100:4) and the product was further purified by gel filtration (LH20, $CHCl_3$/M eOH 95:5) to afford 20 mg (95%) of the receptor 4 as a dark red solid.

$^1$H-NMR (400 MHz, $CDCl_3$/$CD_3OD$): 1.21 (t, J=7.0, 3H), 1.37 and 1.45 (m, 16H), 1.78 (m, 8H), 2.11 (m, 8H), 2.51 (m, 2H), 2.57 (m, 2H), 3.24 (m, 2H), 3.49 (m, 2H), 3.51 (m, 2H), 3.69 (m, 2H), 3.89 (m, 8H), 4.28 (m, 2H), 4.55 (m, 2H), 6.83 (d, J=9.2, 2H), 7.43 (t, J=7.7, 2H), 7.85 (m, 8H), 8.28 (m, 8H), 8.48 (s, 2H). $^{13}$C-NMR (75 MHz, $CDCl_3$/$CD_3OD$): 12.54, 25.60, 29.33, 29.63, 32.61, 46.21, several signals buried under $CD_3OD$, 53.40, 55.45, 55.65, 62.64, 112.44, 123.29, 125.34, 126.98, 127.82, 129.57, 129.82, 129.96, 130.83, 130.97, 135.31, 135.47, 135.98, 144.63, 148.31, 152.60, 157.70, 168.30, 168.36, 168.59, 169.41, 171.94, 174.03. FT-IR (KBr): 3468, 2933, 2859, 1730, 1645, 1598, 1518 cm$^{-1}$. HRMS (M+1): calcd. for $C_{82}H_{92}N_{15}O_{15}$ 1526.6900, found 1526.6843

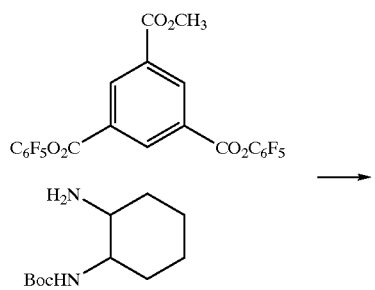

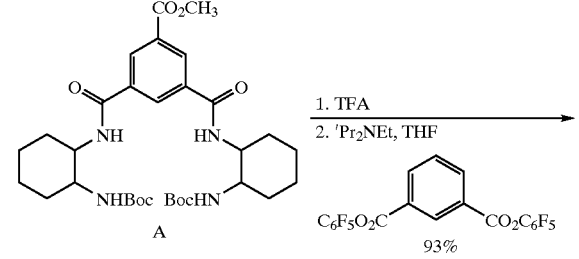

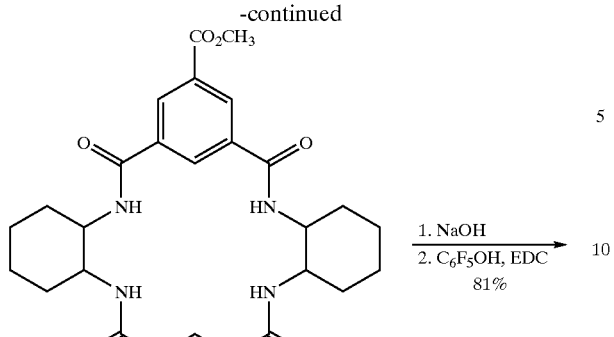

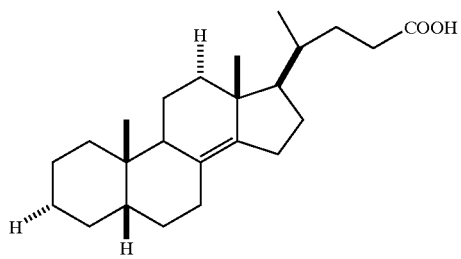

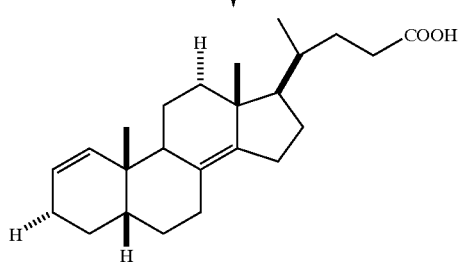

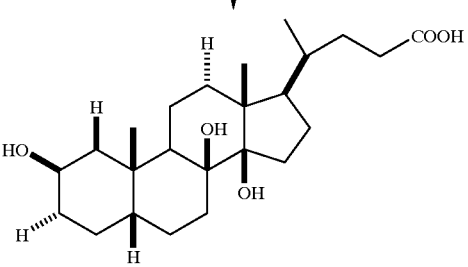

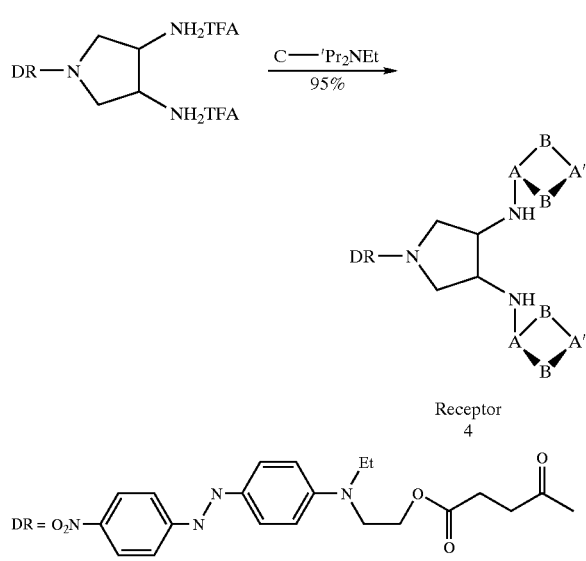

EXAMPLE 6

Preparation of a polyfunctional organic template that is water-soluble. The alpha hydroxyls at positions 3 and 12 are attached to the oligomer chains and the carboxyl group may be use in linking the synthetic receptor to a solid support.

What is claimed:

1. A synthetic receptor comprising a polyfunctional organic template covalently linked to two or more oligomers; said template being a monocyclic nitrogen heterocycle substituted with two or more —O—, —NH— or —C=O to which oligomers are attached; said oligomers chosen independently from the group consisting of straight chained, cyclic and branched oligoamide, oligourea, oligourethane, oligosulfonamide and peftide oligomers; said oligomers comprising three or more monomers; and said —O—, —NH— or —C=O to which an oligomer is attached forming an amide, urea, urethane, sulfonamide or ester bond with said oligomer.

2. A synthetic receptor according to claim 1 wherein said template is chosen from diaminoazepine, diaminopiperidine and diaminopyrrolidine.

3. A synthetic receptor according to claim 2 wherein said template is a diaminoazepine.

4. A synthetic receptor according to claim 3 wherein said oligomers are cyclic oligoamides and a diamine component of said oligoamide is a diaminoazepine.

5. A synthetic receptor according to claim 2 wherein said template is a diaminopyrrolidine.

6. A synthetic receptor comprising a polyfunctional organic template covalently linked to two or more oligomers and to a solid support; said template being a monocyclic nitrogen heterocycle substituted with two or more —O—, —NH— or —C=O to which oligomers are attached; said oligomers chosen independently from the group consisting of straight chained, cyclic and branched oligoamide, oligourea, oligourethane, oligosulfonamide and peptide oligomers; said oligomers comprising three or more monomers; and said —O—, —NH— or —C=O to which an oligomer is attached forming an amide, urea, urethane, sulfonamide or ester bond with said oligomer.

7. A synthetic receptor according to claim 6 wherein said template is chosen from diaminoazepine, diaminopiperidine and diaminopyrrolidine.

8. A synthetic receptor according to claim 7 wherein said template is a diaminoazepine.

9. A synthetic receptor according to claim 8 wherein said oligomers are cyclic oligoamides and a diamine component of said oligoamide is a diaminoazepine.

10. A synthetic receptor according to claim 7 wherein said template is a diaminopyrrolidine.

11. A synthetic receptor according to claim 10 wherein said polyfunctional organic template covalently linked to a solid support is

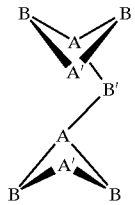

n is 2 or 3;

and Q is a solid support or a solid support linked to an identifier.

12. A synthetic receptor according to claim 10 wherein said synthetic receptor has the structure

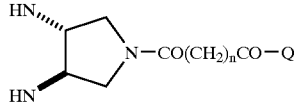

wherein

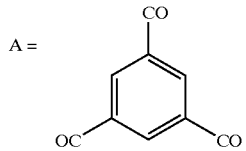 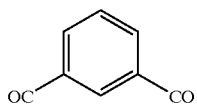

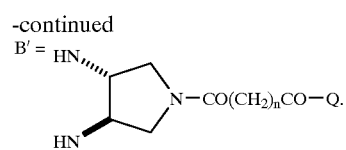

n is 2 or 3;

and Q is a solid support or a solid support linked to an identifier.

13. A synthetic receptor according to claim 10 wherein said synthetic receptor has the structure

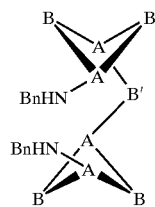

wherein

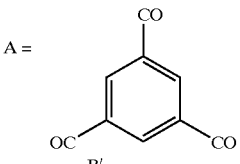 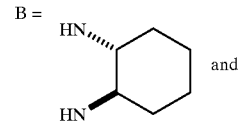

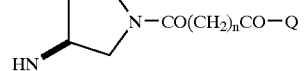

n is 2 or 3;

and Q is a solid support or a solid support linked to an identifier.

14. A synthetic receptor according to claim 6, wherein the solid support is a particle composed of cellulose, controlled-pore glass, silica gel, polystyrene, PEG-polystyrene, polystyrene optionally cross-linked with divinylbenzene, polyacrylamide, latex, polydimethylacrylamide optionally cross-linked with N,N'-bis-acryloyl ethylene diamine, glass coated with a polymer, or low molecular weight non-cross-linked polystyrene and wherein the particle is a spheroid, a capillary, a hollow fiber, a needle, or a solid fiber.

* * * * *

UNITED STATES PATENT AND TRADEMARK OFFICE
CERTIFICATE OF CORRECTION

PATENT NO. : 6,797,522 B1
DATED : September 28, 2004
INVENTOR(S) : Still et al.

It is certified that error appears in the above-identified patent and that said Letters Patent is hereby corrected as shown below:

Column 76,
Line 47, delete the word "peftide" and insert -- peptide --

Signed and Sealed this

Twenty-ninth Day of March, 2005

JON W. DUDAS
*Director of the United States Patent and Trademark Office*